(12) United States Patent
Carlsson et al.

(10) Patent No.: US 7,993,650 B2
(45) Date of Patent: Aug. 9, 2011

(54) POLYPEPTIDES HAVING BINDING AFFINITY FOR HER2

(75) Inventors: Jörgen Carlsson, Uppsala (SE); Stefan Ståhl, Stockholm (SE); Tove Eriksson, Stockholm (SE); Elin Gunneriusson, Lidingö (SE); Fredrik Nilsson, Stockholm (DE)

(73) Assignee: Affibody AB, Bromma (SE)

( * ) Notice: Subject to any disclaimer, the term of this patent is extended or adjusted under 35 U.S.C. 154(b) by 1439 days.

(21) Appl. No.: 10/563,310

(22) PCT Filed: Jun. 30, 2004

(86) PCT No.: PCT/SE2004/001049
§ 371 (c)(1),
(2), (4) Date: May 12, 2006

(87) PCT Pub. No.: WO2005/003156
PCT Pub. Date: Jan. 13, 2005

(65) Prior Publication Data
US 2010/0048868 A1 Feb. 25, 2010

(30) Foreign Application Priority Data

Jul. 4, 2003 (SE) .................................... 0301987
Feb. 9, 2004 (SE) .................................... 0400275

(51) Int. Cl.
*A61K 39/00* (2006.01)
*A61K 39/38* (2006.01)
*G01N 33/53* (2006.01)

(52) U.S. Cl. .... 424/185.1; 424/9.1; 424/9.2; 424/184.1; 424/234.1; 435/4; 435/7.1; 435/7.2; 530/300; 530/350

(58) Field of Classification Search ............... 424/9.1, 424/9.2, 184.1, 185.1, 234.1, 243.1, 4, 7.1, 424/7.2; 435/4, 7.1, 7.2; 350/300, 350
See application file for complete search history.

(56) References Cited

U.S. PATENT DOCUMENTS
2006/0210579 A1 9/2006 Telford et al.

FOREIGN PATENT DOCUMENTS
| WO | WO 89/06692 A1 | 7/1989 |
|---|---|---|
| WO | WO 95/19374 A1 | 7/1995 |
| WO | WO 00/23580 A1 | 4/2000 |
| WO | WO 00/63243 A1 | 10/2000 |
| WO | WO 01/01748 A2 | 1/2001 |
| WO | WO 01/77342 A1 | 10/2001 |
| WO | WO 02/08263 A2 | 1/2002 |

OTHER PUBLICATIONS

Uhlen, M. et al. Journal of Biological Chemistry, vol. 259, No. 3, pp. 1695-1702, 1984.*
Cedergren, L., et al., "Mutational analysis of the interaction between staphylococcal protein A and human IgG," 6123 Protein Engineering, vol. 6, No. 4., 1993, pp. 441-448.
Nord, K., et al., "A combinatorial library of an α-helical bacterial receptor domain," Protein Engineering, vol. 8, No. 6, 1995, pp. 601-608.
Wikman, M. et al., "*Selection and characterization of HER2/neu-binding affibody ligands*", Protein Engineering, Design & Selection, vol. 17, No. 5, pp. 455-462 (Jun. 2004).
Nord, Karin et al., "*Binding proteins selected from combinatorial libraries of an α-helical bacterial recptor domain*", Nature Biotechnology, vol. 15, pp. 772-777 (Aug. 1997).
Gunneriusson, E. et al., "*Affinity maturation of a Taq DNA polymerase specific affibody by helix shuffling*", Protein Engineering, vol. 12, No. 10, pp. 873-878 (1999).
Slamon, M.D., Ph.D., Dennis J. et al., "*Use of Chemotherapy Plus a Monoclonal Antibody Against HER2 for Metastatic Breast Cancer that Overexpresses HER2*", The New England Journal of Medicine, vol. 344, No. 11, pp. 783-792 (Mar. 15, 2001).

* cited by examiner

*Primary Examiner* — Rodney P. Swartz
(74) *Attorney, Agent, or Firm* — Todd E. Garabedian; Wiggin and Dana LLP

(57) ABSTRACT

A polypeptide is provided, which has a binding affinity for HER2 and which is related to a domain of staphylococcal protein A (SPA) in that the sequence of the polypeptide corresponds to the sequence of the SPA domain having from 1 to about 20 substitution mutations. Nucleic acid encoding the polypeptide, as well as expression vector and host cell for expressing the nucleic acid, are also provided. Also provided is the use of such a polypeptide as a medicament, and as a targeting agent for directing substances conjugated thereto to cells overexpressing HER2. Methods, and kits for performing the methods, are also provided, which methods and kits rely on the binding of the polypeptide to HER2.

42 Claims, 35 Drawing Sheets

| Polypeptide | Amino acid sequence | | | | | | SEQ ID NO: |
|---|---|---|---|---|---|---|---|
| Z_wt | VDNKFNKEQQ | NAFYEILHLP | NLNEEQRNAF | IQSLKDDPSQ | SANLLAEAKK | LNDAQAPK | 1 |
| ZHER2 A | VDNKFNKELR | QAYWEIQALP | NLNWTQSRAF | IRSLYDDPSQ | SANLLAEAKK | LNDAQAPK | 2 |
| ZHER2 B | VDNKFNKEPK | TAYWEIVKLP | NLNPEQRRAF | IRSLYDDPSQ | SANLLAEAKK | LNDAQAPK | 3 |
| ZHER2 C | VDNKFNKEPR | EAYWEIQRLP | NLNNKQKAAF | IRSLYDDPSQ | SANLLAEAKK | LNDAQAPK | 4 |
| ZHER2 D | VDNKFNKEWV | QAGSEIYNLP | NLNRAQMRAF | IRSLSDDPSQ | SANLLAEAKK | LNDAQAPK | 5 |
| ZHER2:101 | VDNKFNKEMR | HAYWEIVKLP | NLNPRQKRAF | IRSLYDDPSQ | SANLLAEAKK | LNDAQAPK | 6 |
| ZHER2:102 | VDNKFNKEMR | KAYWEIVLLP | NLNRRQSRAF | IRSLYDDPSQ | SANLLAEAKK | LNDAQAPK | 7 |
| ZHER2:103 | VDNKFNKEMR | HAYWEIATLP | NLNNVQKRAF | IRSLYDDPSQ | SANLLAEAKK | LNDAQAPK | 8 |
| ZHER2:104 | VDNKFNKEFR | TAYWEIVLLP | NLNPGQIRAF | IRSLYDDPSQ | SANLLAEAKK | LNDAQAPK | 9 |
| ZHER2:105 | VDNKFNKELR | TAYWEIVLLP | NLNTWQIRAF | IRSLYDDPSQ | SANLLAEAKK | LNDAQAPK | 10 |
| ZHER2:106 | VDNKFNKEPR | KAYWEIAVLP | NLNPAQKRAF | IRSLYDDPSQ | SANLLAEAKK | LNDAQAPK | 11 |
| ZHER2:107 | VDNKFNKEMR | NAYWEIALLP | NLNNGQKRAF | IRSLYDDPSQ | SANLLAEAKK | LNDAQAPK | 12 |
| ZHER2:108 | VDNKFNKELR | TAYWEIVGLP | NLNHFQVRAF | IRSLYDDPSQ | SANLLAEAKK | LNDAQAPK | 13 |
| ZHER2:109 | VDNKFNKEIR | TAYWEIVLLP | NLNRWQIRAF | IRSLYDDPSQ | SANLLAEAKK | LNDAQAPK | 14 |
| ZHER2:110 | VDNKFNKEIR | NAYWEIALLP | NLNNMQKRAF | IRSLYDDPSQ | SANLLAEAKK | LNDAQAPK | 15 |
| ZHER2:112 | VDNKFNKEFR | KAYWEIVVLP | NLNRMQIRAF | IRSLYDDPSQ | SANLLAEAKK | LNDAQAPK | 16 |
| ZHER2:113 | VDNKFNKEFR | TAYWEIATLP | NLNREQGRAF | IRSLYDDPSQ | SANLLAEAKK | LNDAQAPK | 17 |
| ZHER2:114 | VDNKFNKEMR | TAYWEIVVLP | NLNNKQIRAF | IRSLYDDPSQ | SANLLAEAKK | LNDAQAPK | 18 |
| ZHER2:115 | VDNKFNKEFR | NAYWEIVVLP | NLNRQKRAF | IRSLYDDPSQ | SANLLAEAKK | LNDAQAPK | 19 |
| ZHER2:116 | VDNKFNKEMR | NAYWEIAKLP | NLNNGQKRAF | IRSLYDDPSQ | SANLLAEAKK | LNDAQAPK | 20 |
| ZHER2:118 | VDNKFNKEFR | QAYWEIALLP | NLNHSQTRAF | IRSLYDDPSQ | SANLLAEAKK | LNDAQAPK | 21 |
| ZHER2:120 | VDNKFNKEPR | HAYWEIVKLP | NLNSLQKRAF | IRSLYDDPSQ | SANLLAEAKK | LNDAQAPK | 22 |
| ZHER2:121 | VDNKFNKELR | TAYWEIVGLP | NLNSRQSRAF | IRSLYDDPSQ | SANLLAEAKK | LNDAQAPK | 23 |
| ZHER2:122 | VDNKFNKEMR | TAYWEIAGLP | NLNPKQKRAF | IRSLYDDPSQ | SANLLAEAKK | LNDAQAPK | 24 |
| ZHER2:123 | VDNKFNKELR | TAYWEIQLP | NLNTRQTRAF | IRSLYDDPSQ | SANLLAEAKK | LNDAQAPK | 25 |
| ZHER2:124 | VDNKFNKEFR | KAYWEIVLLP | NLNWEQNRAF | IRSLYDDPSQ | SANLLAEAKK | LNDAQAPK | 26 |
| ZHER2:125 | VDNKFNKEFR | KAYWEITQLP | NLNREQNRAF | IRSLYDDPSQ | SANLLAEAKK | LNDAQAPK | 27 |
| ZHER2:126 | VDNKFNKEMR | HAYWEIATLP | NLNTNQSRAF | IRSLYDDPSQ | SANLLAEAKK | LNDAQAPK | 28 |
| ZHER2:127 | VDNKFNKEMR | NAYWEIVGLP | NLNRWQSRAF | IRSLYDDPSQ | SANLLAEAKK | LNDAQAPK | 29 |

FIG. 1A

| Polypeptide | Amino acid sequence | | | | | SEQ ID NO: |
|---|---|---|---|---|---|---|
| ZHER2:129 | VDNKFNKELR | NAYWEIVKLP | NLNFWQHRAF | IRSLYDDPSQ | SANLLAEAKK | LNDAQAPK | 30 |
| ZHER2:130 | VDNKFNKEFR | TAYWEIVKLP | NLNVRQSRAF | IRSLYDDPSQ | SANLLAEAKK | LNDAQAPK | 31 |
| ZHER2:133 | VDNKFNKEMR | TAYWEIVKLP | NLNDYQKRAF | IRSLYDDPSQ | SANLLAEAKK | LNDAQAPK | 32 |
| ZHER2:135 | VDNKFNKEFR | TAYWEITQLP | NLNRLQSRAF | IRSLYDDPSQ | SANLLAEAKK | LNDAQAPK | 33 |
| ZHER2:137 | VDNKFNKEIR | TAYWEIAGLP | NLNAQQKRAF | IRSLYDDPSQ | SANLLAEAKK | LNDAQAPK | 34 |
| ZHER2:138 | VDNKFNKEMR | QAYWEIVRLP | NLNADQKRAF | IRSLYDDPSQ | SANLLAEAKK | LNDAQAPK | 35 |
| ZHER2:139 | VDNKFNKEMR | NAYWEIVTLP | NLNKTQSRAF | IRSLYDDPSQ | SANLLAEAKK | LNDAQAPK | 36 |
| ZHER2:140 | VDNKFNKEMR | QAYWEIVKLP | NLNPGQSRAF | IRSLYDDPSQ | SANLLAEAKK | LNDAQAPK | 37 |
| ZHER2:148 | VDNKFNKEMR | TAYWEIALLP | NLNNMQKRAF | IRSLYDDPSQ | SANLLAEAKK | LNDAQAPK | 38 |
| ZHER2:153 | VDNKFNKEFR | KAYWEIALLP | NLNKWQIRAF | IRSLYDDPSQ | SANLLAEAKK | LNDAQAPK | 39 |
| ZHER2:158 | VDNKFNKEMR | KAYWEIALLP | NLNRWQIRAF | IRSLYDDPSQ | SANLLAEAKK | LNDAQAPK | 40 |
| ZHER2:159 | VDNKFNKEMR | QAYWEIVLLP | NLNREQNRAF | IRSLYDDPSQ | SANLLAEAKK | LNDAQAPK | 41 |
| ZHER2:162 | VDNKFNKEMR | KAYWEIVGLP | NLNRWQTRAF | IRSLYDDPSQ | SANLLAEAKK | LNDAQAPK | 42 |
| ZHER2:165 | VDNKFNKEMR | TAYWEIVGLP | NLNNQQKRAF | IRSLYDDPSQ | SANLLAEAKK | LNDAQAPK | 43 |
| ZHER2:167 | VDNKFNKELR | TAYWEIVRLP | NLNVNQTRAF | IRSLYDDPSQ | SANLLAEAKK | LNDAQAPK | 44 |
| ZHER2:168 | VDNKFNKEFR | HAYWEIVRLP | NLNAGQHRAF | IRSLYDDPSQ | SANLLAEAKK | LNDAQAPK | 45 |
| ZHER2:169 | VDNKFNKEMR | KAYWEIVTLP | NLNPSQHRAF | IRSLYDDPSQ | SANLLAEAKK | LNDAQAPK | 46 |
| ZHER2:170 | VDNKFNKEMR | TAYWEIAKLP | NLNPPQRRAF | IRSLYDDPSQ | SANLLAEAKK | LNDAQAPK | 47 |
| ZHER2:171 | VDNKFNKELR | TAYWEIVTLP | NLNTSQTRAF | IRSLYDDPSQ | SANLLAEAKK | LNDAQAPK | 48 |
| ZHER2:172 | VDNKFNKEMR | KAYWEIQVLP | NLNVRQKRAF | IRSLYDDPSQ | SANLLAEAKK | LNDAQAPK | 49 |
| ZHER2:177 | VDNKFNKEPR | QAYWEIVLLP | NLNRFQKRAF | IRSLYDDPSQ | SANLLAEAKK | LNDAQAPK | 50 |
| ZHER2:178 | VDNKFNKEMR | NAYWEIVGLP | NLNQGQRRAF | IRSLYDDPSQ | SANLLAEAKK | LNDAQAPK | 51 |
| ZHER2:179 | VDNKFNKEPR | QAYWEIVKLP | NLNSAQKRAF | IRSLYDDPSQ | SANLLAEAKK | LNDAQAPK | 52 |
| ZHER2:180 | VDNKFNKENR | TAYWEIVRLP | NLNRWQSRAF | IRSLYDDPSQ | SANLLAEAKK | LNDAQAPK | 53 |
| ZHER2:205 | VDNKFNKEMR | NAYWEIVLLP | NLNKWQIRAF | IRSLYDDPSQ | SANLLAEAKK | LNDAQAPK | 54 |
| ZHER2:207 | VDNKFNKEMR | TAYWEIALLP | NLNVAQKRAF | IRSLYDDPSQ | SANLLAEAKK | LNDAQAPK | 55 |
| ZHER2:209 | VDNKFNKEFR | NAYWEIVKLP | NLNSGQHRAF | IRSLYDDPSQ | SANLLAEAKK | LNDAQAPK | 56 |
| ZHER2:222 | VDNKFNKEMR | QAYWEIVKLP | NLNIAQNRAF | IRSLYDDPSQ | SANLLAEAKK | LNDAQAPK | 57 |
| ZHER2:223 | VDNKFNKEMR | TAYWEIVKLP | NLNRNQSRAF | IRSLYDDPSQ | SANLLAEAKK | LNDAQAPK | 58 |
| ZHER2:225 | VDNKFNKELR | TAYWEIVSLP | NLNRNQSRAF | IRSLYDDPSQ | SANLLAEAKK | LNDAQAPK | 59 |
| ZHER2:226 | VDNKFNKEMR | NAYWEIVKLP | NLNPGQSRAF | IRSLYDDPSQ | SANLLAEAKK | LNDAQAPK | 60 |

FIG. 1B

| Polypeptide | Amino acid sequence | | | | SEQ ID NO: |
|---|---|---|---|---|---|
| ZHER2:227 | VDNKFNKEMR | QAYWEIALLP | NLNRWQIRAF | IRSLYDDPSQ SANLLAEAKK LNDAQAPK | 61 |
| ZHER2:229 | VDNKFNKEFR | TAYWEIAVLP | NLNNQQKRAF | IRSLYDDPSQ SANLLAEAKK LNDAQAPK | 62 |
| ZHER2:230 | VDNKFNKECR | TAYWEIVKLP | NLNNAQKRAF | IRSLYDDPSQ SANLLAEAKK LNDAQAPK | 63 |
| ZHER2:232 | VDNKFNKEPK | TAYWEIVVLP | NLNSKQKRAF | IRSLYDDPSQ SANLLAEAKK LNDAQAPK | 64 |
| ZHER2:233 | VDNKFNKEMR | NAYWEIVTLP | NLNKWQIRAF | IRSLYDDPSQ SANLLAEAKK LNDAQAPK | 65 |
| ZHER2:234 | VDNKFNKEMR | KAYWEIATLP | NLNKSQSRAF | IRSLYDDPSQ SANLLAEAKK LNDAQAPK | 66 |
| ZHER2:235 | VDNKFNKEFR | TAYWEIVTLP | NLNVGQTRAF | IRSLYDDPSQ SANLLAEAKK LNDAQAPK | 67 |
| ZHER2:236 | VDNKFNKELR | TAYWEIVGLP | NLNTRQSRAF | IRSLYDDPSQ SANLLAEAKK LNDAQAPK | 68 |
| ZHER2:237 | VDNKFNKELR | HAYWEIVQLP | NLNREQGRAF | IRSLYDDPSQ SANLLAEAKK LNDAQAPK | 69 |
| ZHER2:239 | VDNKFNKEFR | HAYWEIIKLP | NLNGKQHRAF | IRSLYDDPSQ SANLLAEAKK LNDAQAPK | 70 |
| ZHER2:240 | VDNKFNKEMR | TAYWEIVSLP | NLNTLQSRAF | IRSLYDDPSQ SANLLAEAKK LNDAQAPK | 71 |
| ZHER2:261 | VDNKFNKEMR | KAYWEIQGLP | NLNNRQKRAF | IRSLYDDPSQ SANLLAEAKK LNDAQAPK | 72 |
| ZHER2:264 | VDNKFNKEMR | NAYWEIAKLP | NLNREQKRAF | IRSLYDDPSQ SANLLAEAKK LNDAQAPK | 73 |
| ZHER2:265 | VDNKFNKEMR | HAYWEIVGLP | NLNMIQQRAF | IRSLYDDPSQ SANLLAEAKK LNDAQAPK | 74 |
| ZHER2:271 | VDNKFNKELR | NAYWEIVKLP | NLNRAQNRAF | IRSLYDDPSQ SANLLAEAKK LNDAQAPK | 75 |
| ZHER2:278 | VDNKFNKELR | TAYWEIIKLP | NLNNYQRRAF | IRSLYDDPSQ SANLLAEAKK LNDAQAPK | 76 |
| ZHER2:0024* | VDNKFNKEPR | EAYWEIQRLP | NLNNKQKTAF | IRSLYDDPSQ SANLLAEAKK LNDAQAPK | 77 |
| ZHER2:0434 | VDNKFNKEMY | AAYWEIIDLP | NLNTPQIHAF | IRSLYDDPSQ SANLLAEAKK LNDAQAPK | 78 |
| ZHER2:3053 | VDNKFNKETR | SAYWEIVNLP | NLNQGQRHAF | IKSLYDDPSQ SANLLAEAKK LNDAQAPK | 79 |

FIG. 1C

POLYPEPTIDES HAVING BINDING AFFINITY FOR HER2

CROSS REFERENCE TO RELATED APPLICATIONS

This application is a U.S. National Stage application of International Application No. PCT/SE2004/001049 filed on Jun. 30, 2004.

FIELD OF THE INVENTION

The present invention is related to a new polypeptide, which binds to Human Epidermal Growth Factor Receptor 2 (in the following referred to as HER2). The polypeptide is related to a domain of staphylococcal protein A (SPA) in that the sequence of the polypeptide corresponds to the sequence of the SPA domain having at least one substitution mutation. The present invention also relates to use of such a HER2 binding polypeptide as a medicament, more particularly use thereof for the preparation of a medicament for treatment of forms of cancer characterized by overexpression of HER2.

BACKGROUND

Molecules related to protein Z, derived from domain B of staphylococcal protein A (SPA) (Nilsson B et al (1987) Protein Engineering 1, 107-133), have been selected from a library of randomized such molecules using different interaction targets (see e g WO 95/19374; Wo00/63243; Nord K et al (1995) Prot Eng 8:601-608; Nord K et al (1997) Nature Biotechnology 15, 772-777). Different target molecules have been used to select such protein Z derivatives, e.g., as described in Nord K et al (1997, supra). The experiments described in this reference outline principles of the general technology of selecting protein Z derivatives against given targets, rather than being a study directed towards the express objective of obtaining a molecule with high enough affinity for use in a specific therapeutic or biotechnological application.

HER2 and its Role in Cancer Diseases

The HER2 proto-oncogene encodes the production of a 185 kD cell surface receptor protein known as the HER2 protein or receptor (Hynes N E et al (1994) Biochim Biophys Acta 1198:165-184). This gene is also sometimes referred to as neu, HER2/neu or c-erbB-2. Neu was first discovered in rats that had been treated with ethylnitrosourea, and exhibited mutation of this gene (Shih C et al (1981) Nature 290:261-264). The mutated version of neu results in the production of a constitutively active form of the receptor, and constitutes a potent oncogene that can transform cells at low copy number (Hynes N E et al, supra).

Normal cells express a small amount of HER2 protein on their plasma membranes in a tissue-specific pattern. No known ligand to HER2 has been elucidated; however, HER2 has been shown to form heterodimers with HER1 (the epidermal growth factor receptor, EGFR), HER3 and HER4 in complex with the ligands for these receptors. Such formation of heterodimer leads to the activated HER2 receptor transmitting growth signals from outside the cell to the nucleus, thus controlling aspects of normal cell growth and division (Sundaresan S et al (1999) Curr Oncol Rep 1:16-22).

In tumor cells, errors in the DNA replication system may result in the existence of multiple copies of a gene on a single chromosome, which is a phenomenon known as gene amplification. Amplification of the HER2 gene leads to an increased transcription of this gene. This elevates HER2 mRNA levels and increases the concomitant synthesis of HER2 protein, which results in HER2 protein overexpression on the surface of these tumor cells. This overexpression can result in HER2 protein levels that are 10- to 100-fold greater than those found in the adjacent normal cells. This, in turn, results in increased cell division and a concomitantly higher rate of cell growth. Amplification of the HER2 gene is implicated in transformation of normal cells to the cancer phenotype (Hynes N E et al, supra; Sundaresan S et al, supra).

Overexpression of HER2 protein is thought to result in the formation of homodimers of HER2, which in turn results in a constitutively active receptor (Sliwkowski M X et al (1999) Semin Oncol 26(4 Suppl 12):60-70). Under these conditions, growth-promoting signals may be continuously transmitted into the cells in the absence of ligands. Consequently, multiple intracellular signal transduction pathways become activated, resulting in unregulated cell growth and, in some instances, oncogenic transformation (Hynes N E et al, supra). Thus, the signal transduction mechanisms mediated by growth factor receptors are important targets for inhibiting cell replication and tumor growth.

Breast cancer is the most common malignancy among women in the United States, with 192200 new cases projected to have occurred in 2001 (Greenlee R et al (2001) C A Cancer J Clin 51:15-36). In approximately 25% of all breast cancer patients, there is an overexpression of the HER2 gene due to amplification thereof (Slamon D J et al (1989) Science 244: 707-712). This overexpression of HER2 protein correlates with several negative prognostic variables, including estrogen receptor-negative status, high S-phase fraction, positive nodal status, mutated p53, and high nuclear grade (Sjogren S et al (1998) J Clin Oncol 16(2):462-469). According to Slamon et al (supra), the amplification of the HER2 gene was found to correlate strongly with shortened disease-free survival and shortened overall survival of node-positive patients.

For these reasons, it has been, and is still, an important goal to further pursue investigations into the role of HER2 in the pathogenesis and treatment of breast cancer. The identification of molecules that interact with HER2 forms one part of this effort.

Preclinical in vitro studies have examined whether inhibition of HER2 activity could affect tumor cell growth. Treatment of SK-BR-3 breast cancer cells overexpressing HER2 protein with 4D5, one of several murine anti-HER2 monoclonal antibodies, did indeed inhibit tumor cell proliferation, compared to treatment with a control monoclonal antibody. Administration of 4D5 to mice bearing human breast and ovarian cancers (xenografts) that overexpress HER2 prolonged their tumor-free survival time. Similar studies demonstrated the growth inhibition by anti-HER2 monoclonal antibodies in human gastric cancer xenografts in mice (Pietras R J et al (1994) Oncogene 9:1829-1838).

Among the approaches to inhibiting the HER2 protein abundantly present on tumor cell surfaces with an antibody, one therapy has become commercially available during recent years. Thus, the monoclonal antibody 4D5, or trastuzumab, is marketed for this purpose by F Hoffman-La Roche and Genentech under the trade name of Herceptine.

Notwithstanding the obvious advantages shown by antibody therapy against cancers characterized by overexpression of HER2 protein, the fact remains that a variety of factors have the potential of reducing antibody efficacy (see e g Reilly R M et al (1995) Clin Pharmacokinet 28:126-142). These include the following: (1) limited penetration of the antibody into a large solid tumor or into vital regions such as the brain; (2) reduced extravasation of antibodies into target sites owing to decreased vascular permeability; (3) cross-reactivity and nonspecific binding of antibody to normal tissues, reducing the targeting effect; (4) heterogeneous tumor uptake resulting in untreated zones; (5) increased metabolism of injected antibodies, reducing therapeutic effects; and (6) rapid formation of HAMA and human antihuman antibodies, inactivating the therapeutic antibody.

In addition, toxic effects have been a major obstacle in the development of therapeutic antibodies for cancer (Carter P (2001) Nat Rev Cancer 1:118-129; Goldenberg D M (2002) J Nucl Med 43:693-713; Reichert J M (2002) Curr Opin Mol Ther 4:110-118). Cross-reactivity with healthy tissues can cause substantial side effects for unconjugated (naked) antibodies, which side effects may be enhanced upon conjugation of the antibodies with toxins or radioisotopes. Immune-mediated complications include dyspnea from pulmonary toxic effects, occasional central and peripheral nervous system complications, and decreased liver and renal function. On occasion, unexpected toxic complications can be seen, such as the cardiotoxic effects associated with the HER-2 targeting antibody trastuzumab (Herceptin®) (Schneider J W et al (2002) Semin Oncol 29(3 suppl 11):22-28). Radioimmunotherapy with isotope-conjugated antibodies also can cause bone marrow suppression.

Despite the recent clinical and commercial success of the currently used anticancer antibodies, a substantial number of important questions thus remain concerning the future of this therapeutic strategy. As a consequence, the continued provision of agents with a comparable affinity for HER2 remains a matter of substantial interest within the field, as well as the provision of uses of such molecules in the treatment of disease.

DISCLOSURE OF THE INVENTION

It is an object of the present invention to satisfy this interest through the provision of a polypeptide that is characterized by specific binding to HER2.

A related object of the invention is an HER2 binding polypeptide which exhibits little or no non-specific binding.

It is another object of the invention to provide an HER2 binding polypeptide that can readily be used as a moiety in a fusion polypeptide.

Another object is the provision of an HER2 binding polypeptide, which solve one or more of the known problems experienced with existing antibody reagents.

A further object of the invention is to provide an HER2 binding polypeptide, which is amenable to use in therapeutic applications.

A related object is to find new forms for the treatment, inhibition and/or targeting in the clinical setting of cancer diseases characterized by an overexpression of HER2 protein.

It is also an object to provide a molecule which can be used as a reagent for the detection of HER2 at a low concentration.

These and other objects are met by the different aspects of the invention as claimed in the appended claims. Thus, in a first aspect, the invention provides a polypeptide, which has a binding affinity for HER2 and which is related to a domain of staphylococcal protein A (SPA) in that the sequence of the polypeptide corresponds to the sequence of the SPA domain having from 1 to about 20 substitution mutations.

In an embodiment of the polypeptide according to this aspect of the invention, the affinity thereof for HER2 is such that the $K_D$ value of the interaction is at most $1 \times 10^{-6}$ M. In another embodiment, the affinity of the polypeptide for HER2 is such that the $K_D$ value of the interaction is at most $1 \times 10^{-7}$ M.

In another embodiment, the polypeptide according to the invention binds specifically to the extracellular domain, ECD, of the HER2 protein.

In accordance herewith, the present inventors have found that it is possible to obtain a high-affinity HER2 binding polypeptide through substitution mutagenesis of a domain from SPA, and that such a polypeptide is able to interact with HER2. The inventive polypeptide finds application as an alternative to antibodies against HER2 in diverse applications. As non-limiting examples, it will be useful in the treatment of cancers characterized by HER2 overexpression, in inhibiting cell signaling by binding to the HER2 on a cell surface, in the diagnosis of cancer both in vivo and in vitro, in targeting of agents to cells overexpressing HER2, in histochemical methods for the detection of HER2, in methods of separation and other applications. The polypeptide according to the invention may prove useful in any method which relies on affinity for HER2 of a reagent. Thus, the polypeptide may be used as a detection reagent, a capture reagent or a separation reagent in such methods, but also as a therapeutic agent in its own right or as a means for targeting other therapeutic agents to the HER2 protein. Methods that employ the polypeptide according to the invention in vitro may be performed in different formats, such as in microtiter plates, in protein arrays, on biosensor surfaces, on tissue sections, and so on. Different modifications of, and/or additions to, the polypeptide according to the invention may be performed in order to tailor the polypeptide to the specific use intended, without departing from the scope of the present invention. Such modifications and additions are described in more detail below, and may comprise additional amino acids comprised in the same polypeptide chain, or labels and/or therapeutic agents that are chemically conjugated or otherwise bound to the polypeptide according to the invention. Furthermore, the invention also encompasses fragments of the polypeptide that retain the capability of binding to HER2.

"Binding affinity for HER2" refers to a property of a polypeptide which may be tested e.g., by the use of surface Plasmon resonance technology, such as in Biacore® instrument. HER2 binding affinity may be tested in an experiment wherein HER2 is immobilized on a sensor chip of the instrument, and a sample containing the polypeptide to be tested is passed over the chip. Alternatively, the polypeptide to be tested is immobilized on a sensor chip of the instrument, and a sample containing HER2 is passed over the chip. The skilled person may then interpret the sensorgrams obtained to establish at least a qualitative measure of the polypeptide's binding affinity for HER2. If a quantitative measure is sought, e.g., with the purpose to establish a certain $K_D$ value for the interaction, it is again possible to use surface plasmon resonance methods. Binding values may e.g., be defined in a Biacore®2000 instrument (Biacore AB). HER2 is immobilized on a sensor chip of the instrument, and samples of the polypeptide whose affinity is to be determined are prepared by serial dilution and injected in random order. $K_D$ values may then be calculated from the results, using e.g., the 1:1 Langmuir binding model of the BIAevaluation 3.2 software provided by the instrument manufacturer.

As stated above, the sequence of the polypeptide according to the present invention is related to the SPA domain sequence in that from 1 to about 20 amino acid residues of said SPA domain have been substituted for other amino acid residues. However, the substitution mutations introduced should not affect the basic structure of the polypeptide. That is, the overall fold of the $C_\alpha$ backbone of the polypeptide of the invention will be essentially the same as that of the SPA domain to which it is related, e.g., having the same elements of secondary structure in the same order etc. Thus, polypeptides fall under the definition of having the same fold as the SPA domain if basic structural properties are shared, those properties e.g., resulting in similar CD spectra. The skilled person is aware of other parameters that are relevant. This requirement of essentially conserving the basic structure of the SPA domain, upon mutation thereof, places restrictions on what positions of the domain may be subject to substitution. When starting from the known structure of the Z protein, for example, it is preferred that amino acid residues located on the surface of the Z protein are substituted, whereas amino acid residues buried within the core of the Z protein "three-helix bundle" should be kept constant in order to preserve the structural properties of the molecule. The same reasoning applies to other SPA domains, and fragments thereof.

The invention also encompasses polypeptides in which the HER2 binding polypeptide described above is present as an HER2binding domain, to which additional amino acid residues have been added at either terminal. These additional amino acid residues may play a role in the binding of HER2 by the polypeptide, but may equally well serve other purposes, related for example to one or more of the production, purification, stabilization, coupling or detection of the polypeptide. Such additional amino acid residues may comprise one or more amino acid residues added for purposes of chemical coupling. An example of this is the addition of a cysteine residue at the very first or very last position in the polypeptide chain, i.e., at the N or C terminus. Such additional amino acid resides may also comprise a "tag" for purification or detection of the polypeptide, such as a hexahistidyl ($His_6$) tag, or a "myc" tag or a "flag" tag for interaction with antibodies specific to the tag. The skilled person is aware of other alternatives.

The "additional amino acid residues" discussed above may also constitute one or more polypeptide domain(s) with any desired function, such as the same binding function as the first, HER2-binding domain, or another binding function, or an enzymatic function, or a fluorescent function, or mixtures thereof.

Thus, the invention encompasses multimers of the polypeptide with affinity for HER2. It may be of interest, e g when using the polypeptide according to the invention for treatment of cancer or in a method of purification of HER2, to obtain even stronger binding of HER2 than is possible with one polypeptide according to the invention. In this case, the provision of a multimer, such as a dimer, trimer or tetramer, of the polypeptide may provide the necessary avidity effects. The multimer may consist of a suitable number of polypeptides according to the invention. These polypeptide domains according to the invention, forming monomers in such a multimer, may all have the same amino acid sequence, but it is equally possible that they have different amino acid sequences. The linked polypeptide "units" in a multimer according to the invention may be connected by covalent coupling using known organic chemistry methods, or expressed as one or more fusion polypeptides in a system for recombinant expression of polypeptides, or joined in any other fashion, either directly or via a linker, for example an amino acid linker.

Additionally, "heterogenic" fusion polypeptides, in which the HER2 binding polypeptide constitutes a first domain, or first moiety, the second and further moieties have other functions than binding HER2, are also contemplated and fall within the ambit of the present invention. The second and further moiety/moieties of the fusion polypeptide may comprise a binding domain with affinity for another target molecule than HER2. Such a binding domain may well also be related to an SPA domain through substitution mutation at from 1 to about 20positions thereof. The result is then a fusion polypeptide having at least one HER2-binding domain and at least one domain with affinity for said other target molecule, in which both domains are related to an SPA domain. This makes it possible to create multispecific reagents that may be used in several biotechnological applications, such as used as therapeautic agents or as capture, detection or separation reagents. The preparation of such multispecific multimers of SPA domain related polypeptides, in which at least one polypeptide domain has affinity for HER2, may be effected as described above for the multimer of several HER2 binding "units". In other alternatives, the second or further moiety or moieties may comprise an unrelated, naturally occurring or recombinant, protein (or a fragment thereof retaining the binding capability of the naturally occurring or recombinant protein) having a binding affinity for a target. An example of such a binding protein, which has an affinity for human serum albumin and may be used as fusion partner with the HER2 binding SPA domain derivative of the invention, is the albumin binding domain of streptococcal protein G (SPG) (Nygren P-Å et al (1988) Mol Recogn 1:69-74). A fusion polypeptide between the HER2 binding SPA domain-related polypeptide and the albumin binding domain of SPG thus falls within the scope of the present invention. When the polypeptide according to the invention is administered to a human subject as a therapeutic agent or as a targeting agent, the fusion thereof to a moiety which binds serum albumin may prove beneficial, in that the half-life in vivo of such a fusion protein may likely prove to be extended as compared to the half-life of the SPA domain related HER2 binding moiety in isolation (this principle has been described e.g., in WO91/01743).

Other possibilities for the creation of fusion polypeptides are also contemplated. Thus, the HER2 binding SPA domain-related polypeptide according to the first aspect of the invention may be covalently coupled to a second or further moiety or moieties, which in addition to, or instead of, target binding exhibit other functions. One example is a fusion between one or more HER2 binding polypeptide(s) and an enzymatically active polypeptide serving as a reporter or effector moiety. Examples of reporter enzymes, which may be coupled to the HER2 binding polypeptide to form a fusion protein, are known to the skilled person and include enzymes such as β-galactosidase, alkaline phosphatase, horseradish peroxidase, carboxypeptidase. Other options for the second and further moiety or moieties of a fusion polypeptide according to the invention include fluorescent polypeptides, such as green fluorescent protein, red fluorescent protein, luciferase and variants thereof.

Other options for the second and further moiety or moieties of a fusion polypeptide according to the invention include a moiety or moieties for therapeutic applications. In therapeutic applications, other molecules may also be coupled, covalently or non-covalently, to the inventive polypeptide by other means. Non-limiting examples include enzymes for "ADEPT" (antibody-directed enzyme prodrug therapy) applications using the polypeptide according to the invention for direction of the effector enzyme (e.g., carboxypeptidase); proteins for recruitment of effector cells and other components of the immune system; cytokines, such as IL-2, IL-12, TNFα, IP-10; proco-agulant factors, such as tissue factor, von Willebrand factor; toxins, such as ricin A, Pseudomonas exotoxin, calcheamicin, maytansinoid; toxic small molecules, such as auristatin analogs, doxorubicin. Also, the above named additional amino acids (notably hexahistidine tag, cysteine), provided with the aim of coupling chelators for radioisotopes to the polypeptide sequence, are contemplated, in order to easily incorporate radiating nuclides for diagnosis (e.g., $^{68}$Ga, $^{76}$Br, $^{111}$Br, $^{99}$Tc, $^{124}$I, $^{125}$I) or therapy (e.g., $^{90}$Y, $^{131}$I, $^{211}$At).

The invention encompasses polypeptides in which the HER2 binding polypeptide described above has been provided with a label group, such as at least one fluorophore, biotin or a radioactive isotope, for example for purposes of detection of the polypeptide.

With regard to the description above of fusion proteins incorporating the HER2 binding polypeptide according to the invention, it is to be noted that the designation of first, second and further moieties is made for clarity reasons to distinguish between the HER2 binding moiety or moieties on the one hand, and moieties exhibiting other functions on the other hand. These designations are not intended to refer to the actual order of the different domains in the polypeptide chain of the fusion protein. Thus, for example, said first moiety may without restriction appear at the N-terminal end, in the middle, or at the C-terminal end of the fusion protein.

An example of an SPA domain for use as a starting, point for the creation of a polypeptide according to the invention is protein Z, derived from domain B of staphylococcal protein A. As pointed out in the Background section, this protein has previously been used as a scaffold structure for the creation of molecules, denoted Affibody® molecules, capable of binding to a variety of targets. The 58 amino acid sequence of unmodified protein Z, denoted $Z_{wt}$, is set out in SEQ ID NO:1 and illustrated in FIG. 1.

In an embodiment of the polypeptide according to the invention, it is related to a domain of SPA in that the sequence of the polypeptide corresponds to the sequence of the SPA domain having from 4 to about 20 substitution mutations. Other embodiments may have from 1 to about 13 substitution mutations, or from 4 to about 13 substitution mutations.

In a more specific embodiment of the polypeptide according to the invention, its sequence corresponds to the sequence set forth in SEQ ID NO:1 having from 1 to about 20 substitution mutations, such as from 4 to about 20, from 1 to about 13 or from 4 to about 13 substitution mutations.

The polypeptide according to the invention may in some embodiments correspond to the sequence set forth in SEQ ID NO:1, which sequence comprises substitution mutations at one or more of the positions 13, 14, 28, 32 and 35. Additionally, the sequence of the polypeptide according to the invention may comprise substitution mutations at one or more of the positions 9, 10, 11, 17, 18, 24, 25 and 27.

The sequence of a polypeptide according to another embodiment of the invention corresponds to SEQ ID NO:1, comprising at least a substitution mutation at position 13 from phenylalanine to tyrosine.

The sequence of a polypeptide according to another embodiment of the invention corresponds to SEQ ID NO:1, comprising at least a substitution mutation at position 14 from tyrosine to tryptophan.

The sequence of a polypeptide according to another embodiment of the invention corresponds to SEQ ID NO:1, comprising at least a substitution mutation at position 28 from asparagine to an amino acid residue selected from arginine and histidine, more preferably to arginine.

The sequence of a polypeptide according to another embodiment of the invention corresponds to SEQ ID NO:1, comprising at least a substitution mutation at position 32 from glutamine to arginine.

The sequence of a polypeptide according to another embodiment of the invention corresponds to SEQ ID NO:1, comprising at least a substitution mutation at position 35 from lysine to tyrosine.

The sequence of a polypeptide according to another embodiment of the invention corresponds to SEQ ID NO:1, comprising at least a substitution mutation at position 10 from glutamine to arginine.

The sequence of a polypeptide according to another embodiment of the invention corresponds to SEQ ID NO:1, comprising at least a substitution mutation at position 11 from asparagine to threonine.

The sequence of a polypeptide according to another embodiment of the invention corresponds to SEQ ID NO:1, comprising at least a substitution mutation at position 17 from leucine to valine.

The sequence of a polypeptide according to another embodiment of the invention corresponds to SEQ ID NO:1, comprising at least a substitution mutation at position 27 from arginine to an amino acid residue selected from lysine and serine.

A preferred polypeptide according to the invention corresponds to SEQ ID NO:1, comprising at least the following mutations: F13Y, Y14W, N28R, Q32R and K35Y.

Examples of specific sequences of different embodiments of the polypeptide according to the invention, each comprising one or more of the specific mutations described above, are set out in SEQ ID NO:2-79 and illustrated in FIG. 1. HER2 binding characteristics of these polypeptides are disclosed in the examples that follow this general description of the invention.

As an alternative to using the unmodified SPA domain, the SPA domain may also be subjected to mutagenesis in order to increase the stability thereof in alkaline conditions. Such stabilization involves the site-directed substitution of any asparagine residues appearing in the unmodified sequence with amino acid residues that are less sensitive to alkaline conditions. When using the polypeptide according to the invention as an affinity ligand in affinity chromatography, this property of having a reduced sensitivity to alkali provides benefits; affinity chromatography columns are frequently subjected to harsh alkali treatment for cleaning in place (CIP) between separation runs, and the ability to withstand such treatment prolongs the useful lifetime of the affinity chromatography matrix. As an example, making use of protein Z as starting point, the polypeptide according to the invention may, in addition to the substitution mutations conferring HER2 binding, have modifications in that at least one asparagine residue selected from N3, N6, N11, N21, N23, N28, N43 and N52 has been substituted with an amino acid residue that is less sensitive to alkaline treatment. Non-limiting examples of such polypeptides are those having the following sets of mutations (with respect to the sequence of $Z_{wt}$): N3A; N6D; N3A, N6D and N23T; N3A, N6D, N23T and N28A; N23T; N23T and N43E; N28A; N6A; N11S; N11S and N23T; N6A and N23T. Thus, these SPA domains, as well as other SPA domains that have been subjected to asparagine mutation for stability reasons, may all be subjected to further substitution mutation of amino acid residues in order to obtain the HER2 binding polypeptide of the invention. Alternatively, an HER2 binding polypeptide of the invention which comprises asparagine residues may be subjected to further mutation to replace such residues. Evidently, this latter alternative is only possible to the extent that the HER2 binding capability of such a molecule is retained.

The invention also encompasses polypeptides that have been derived from any of the polypeptides described above, through generation of a fragment of the above polypeptides, which fragment retains HER2 affinity. The fragment polypeptide is such that it remains stable, and retains the specificity to bind HER2. The possibility to create fragments of a wild-type SPA domain with retained binding specificity to immunoglobulin G is shown by Braisted A C and Wells J A et al in Proc Natl Acad Sci USA 93:5688-5692 (1996). By using a structure-based design and phage display methods, the binding domain of a three-helix bundle of 59 residues was reduced to a resulting two-helix derivative of 33 residues. This was achieved by stepwise selection of random mutations from different regions, which caused the stability and binding affinity to be iteratively improved. Following the same reasoning with the polypeptides according to the first aspect of the invention, the skilled man would be able to obtain a "minimized" HER2 binding polypeptide with the same binding properties as that of the "parent" HER2 polypeptide. Hence, a polypeptide constituting a fragment of a polypeptide according to the above aspect of the invention, which fragment retains binding affinity for HER2, is a further aspect of the invention.

Another aspect of the present invention relates to a nucleic acid molecule comprising a sequence which encodes a polypeptide according to the invention.

A further aspect of the present invention relates to an expression vector comprising the nucleic acid molecule of the previous aspect, and other nucleic acid elements that enable production of the polypeptide according to the invention through expression of the nucleic acid molecule.

Yet another aspect of the present invention relates to a host cell comprising the expression vector of the previous aspect.

The latter three aspects of the invention are tools for the production of a polypeptide according to the invention, and the skilled person will be able to obtain them and put them into practical use without undue burden, given the information herein concerning the polypeptide that is to be expressed and given the current level of skill in the art of recombinant expression of proteins. As an example, a plasmid for the expression of unmodified protein Z (see e g Nilsson B et al (1987), supra) may be used as starting material. The desired substitution mutations may be introduced into this plasmid, using known techniques, to obtain an expression vector in accordance with the invention.

However, the polypeptide according to the invention may also be produced by other known means, including chemical synthesis or expression in different prokaryotic or eukaryotic hosts, including plants and transgenic animals. When using chemical polypeptide synthesis, any of the naturally occurring amino acid resides in the polypeptide as described above may be replaced with any corresponding, non-naturally occurring amino acid residue or derivative thereof, as long as the HER2 binding capacity of the polypeptide is not substantially compromised. The binding capability should at least be retained, but replacement with a corresponding, non-naturally occurring amino acid residue or derivative thereof may actually also serve to improve the HER2 binding capacity of the polypeptide. Also, the incorporation of a non-naturally occurring amino acid may be performed in order to provide a site for alternative coupling of molecules (e.g., labels, effectors, chelators etc) to the HER2 binding polypeptide. Non-classical amino acids, or synthetic amino acid analogs, include, but are not limited to, the D-isomers of the common amino acids, α-amino isobutyric acid, 4-amino butyric acid, 2-amino butyric acid, 6-amino hexanoic acid, 2-amino isobutyric acid, 3-amino propionic acid, ornithine, norleucine, norvaline, hydroxyproline, sarcosine, citrulline, cysteic acid, t-butylglycine, t-butylalanine, phenylglycine, cyclohexylalanine, β-alanine, fluoroamino acids, designer amino acids such as β-methyl amino acids, Cα-methyl amino acids, Nα-methyl amino acids, and amino acid analogs in general. Furthermore, the amino acid residues can be present in D or L form.

The present invention also concerns different aspects of using the above-described HER2 binding polypeptide, as well as various methods for treatment, diagnosis and detection in which the polypeptide is useful due to its binding characteristics. When referring to the "HER2 binding polypeptide" in the following description of these uses and methods, this term is intended to encompass the HER2 binding polypeptide alone, but also all those molecules based on this polypeptide described above that e.g., constitute fragments thereof and/or incorporate the HER2 binding polypeptide as a moiety in a fusion protein and/or are conjugated to a label or therapeutic agent and/or are provided with additional amino acid residues as a tag for other purposes. As explained above, such fusion protein, derivatives, fragments etc form a part of the present invention.

Thus, in one such aspect, the invention provides use of the HER2 binding polypeptide as described herein as a medicament.

In a further aspect, the invention provides use of the HER2 binding polypeptide as described herein in the preparation of a medicament for the treatment of at least one form of cancer characterized by overexpression of HER2. One particular form of cancer characterized by overexpression of HER2 is a breast cancer. As described in the Background section, approximately 25% of all breast cancer patients show an overexpression of HER2 (Slamon D J et al, supra).

Without wishing to be bound by this theory, the polypeptide described herein is thought to be useful as a therapeutic agent based on at least one of the following mechanisms: (i) Potentiation of chemotherapy (cytotoxic), in that administration of the polypeptide will function in synergy with existing and coming chemotherapies and hormonal therapies. Blocking of the HER2 protein on cell surfaces has been shown to prevent DNA repair following the impact of DNA-damaging drugs (Pietras R J et al (1994) Oncogene 9:1829-1838). (ii) Inhibition of the proliferation of tumor cells (cytostatic). This reasoning is based on the observation that downregulation of HER2 protein occurs when a molecule (antibody) attaches to the HER2 protein on the cell surface, causing some receptors to be endocytosed, limiting the signal for further cell growth (Baselga J et al (1998) Cancer Res 58:2825-2831; Sliwkowski M X et al, supra).

A related aspect of the present invention is the provision of a method for the treatment of at least one form of cancer characterized by overexpression of HER2, which method comprises administering to a subject in need of such treatment a therapeutically effective amount of a composition, which comprises a HER2 binding polypeptide as described herein as an active substance.

The HER2 binding properties of the polypeptide according to the invention, together with the suitability of the polypeptide for the creation of fusion proteins and/or labeled binding molecules, means that the polypeptide may also be useful for targeting of other active substances to the site of a tumor which comprises cells that overexpress HER2. Thus, another aspect of the present invention is the provision of use of the HER2 binding polypeptide as described herein in conjugated to an substance with anti-cancer activity for delivery of said substance to cells that overexpress HER2. The conjugated substance may also be one that functions to elicit a response of the subject's endogenous immune system. Natural killer (NK) cells, or other effectors of the immune system, may be attracted to the complex of HER2 and HER2 binding polypeptide on the cell's surface through the provision of a fusion moiety that serves the function of recruiting such effectors. The NK cells or other effectors, having detected that the cell is abnormal, attach to the HER2 binding fusion protein. Eventually, the cancer cell is consumed by the NK cells (Sliwkowski M X et al, supra; Pegram M D et al (1997) Proc Am Assoc Cancer Res 38:602, Abstract 4044).

Such an active substance may be a protein coupled to the HER2 binding polypeptide by fusion or by chemical linkage, such as chosen among effector enzymes for "ADEPT" (antibody-directed enzyme prodrug therapy) applications; proteins for recruitment of effector cells and other components of the immune system; cytokines, such as IL-2, IL-12, TNFα, IP-10; procoagulant factors, such as tissue factor, von Willebrand factor; toxins, such as ricin A, *Pseudomonas* endotoxin, calcheamicin, maytansinoid. Alternatively, the active substance may be a cytotoxic drug, such as auristatin analogs or doxorubicin, or a radioactive isotope (e g $^{90}$Y, $^{131}$I, $^{211}$At), which isotope may be associated with the HER2 binding polypeptide directly, or associated via a chelating agent, such as the well known chelators DOTA or DTPA.

In a related aspect, the invention also provides a method of directing a substance having an anti-cancer activity to cells overexpressing HER2 in vivo, comprising administering a conjugate of said active substance and a HER2 binding polypeptide as described herein to a patient. The conjugate is suitably as described in the pre-ceding paragraph.

Another aspect of the present invention is the use of the HER2 binding polypeptide as described herein for the detection of HER2 in a sample. For example, such detection may be performed with the aim of diagnosing disease states characterized by overexpression of HER2. The detection of HER2 presence in a sample may be performed in vitro or in vivo. A preferred option for in vivo diagnosis is the use of positron emission tomography, PET. The sample in question may e.g., be a biological fluid sample or a tissue sample. A common method, in use today with antibodies directed against HER2, which method may be adapted for use with the HER2, which method may be adapted for use with the HER2 binding polypeptides of the present invention, is histochemical detection of HER2 presence used for identification of HER2 protein overexpression in fresh, frozen, or formalin-fixed, paraffinembedded tissue samples. For the purposes of HER2 detection, the polypeptide according to the invention may again be used as part of a fusion protein, in which the other domain is a reporter enzyme or fluorescent enzyme. Alternatively, it may be labeled with one or more fluorescent agent(s) and/or radioactive isotope(s), optionally via a chelator. Suitable radioactive isotopes include $^{68}$Ga, $^{76}$Br, $^{111}$In, $^{99}$Tc $^{124}$I and $^{125}$I.

Yet another aspect of the present invention is constituted by the use of an HER2 binding polypeptide as described herein in a method of detecting HER2 in a biological fluid sample. This method comprises the steps of (i) providing a biological fluid sample from a patient to be tested, (ii) applying an HER2 binding polypeptide as described herein to the sample under conditions such that binding of the polypeptide to any HER2 present in the sample is enabled, (iii) removing non-bound polypeptide, and (iv) detecting bound polypeptide. The amount of the detected bound polypeptide is correlated to the amount of HER2 present in the sample. In step (ii), the application of HER2 binding polypeptide to the sample may be performed in any suitable format, and includes for example the situation when the HER2 binding polypeptide is immobilized on a solid support with which the sample is brought into contact, as well as set-ups in which the HER2 binding polypeptide is present in solution.

Another, related, aspect of the present invention is a method for the detection of HER2 in a sample, comprising the steps of (i) providing a tissue sample suspected of containing HER2, for example a cryostat section or a paraffin-embedded section of tissue, (ii) applying an HER2 binding polypeptide according to the invention to said sample under conditions conducive for binding of the polypeptide to any HER2 present in the sample, (iii) removing non-bound polypeptide, and (iv) detecting bound polypeptide. The amount of the detected bound polypeptide is correlated to the amount of HER2 present in the sample.

Also provided by the present invention is a kit for diagnosis of HER2 overexpression in a tissue sample, comprising the HER2 binding polypeptide according to the invention fused to a reporter enzyme (such as alkaline phosphatase or horseradish peroxidase), reagents for detection of enzyme activity, and positive and negative control tissue slides.

Also provided by the present invention is a kit for diagnosis of HER2 overexpression in a tissue sample, comprising the HER2 binding polypeptide according to the invention fused to a tag for detection by an antibody (such as a flag tag or myc tag), a primary antibody specific for the tag, a secondary antibody specific for the primary antibody and conjugated to a reporter enzyme, reagents for detection of enzyme activity, and positive and negative control tissue slides.

One area in diagnosis applications is the in vivo detection of cancer cells or aggregates thereof. The invention provides a kit for performing such diagnosis, which kit comprises the HER2 binding polypeptide according to the invention labeled with a chelator, a diagnostic radioactive isotope (non-limiting examples are $^{68}$Ga, $^{76}$Br, $^{111}$In, $^{99}$Tc, $^{124}$I and $^{125}$I), and reagents for the analysis of the incorporation efficiency.

As described above, the invention encompasses use of the HER2 binding polypeptide according to the invention to target active substances to cells that overexpress HER2, such as certain types of cancer cells. The invention also provides a kit for this purpose, comprising HER2 binding polypeptide according to the invention labeled with a chelator, a therapeutic radioactive isotope (non-limiting examples are $^{90}$Y, $^{131}$I, $^{211}$At), and reagents for the analysis of the incorporation efficiency.

BRIEF DESCRIPTION OF THE DRAWINGS

FIG. 1 shows an alignment of the sequences of the sequence listing. The amino acid positions that have been subjected to modification in the polypeptides $Z_{HER2\ A}$ according to the invention (represented by SEQ ID NO:2-79) are indicated in bold.

Figure 2:
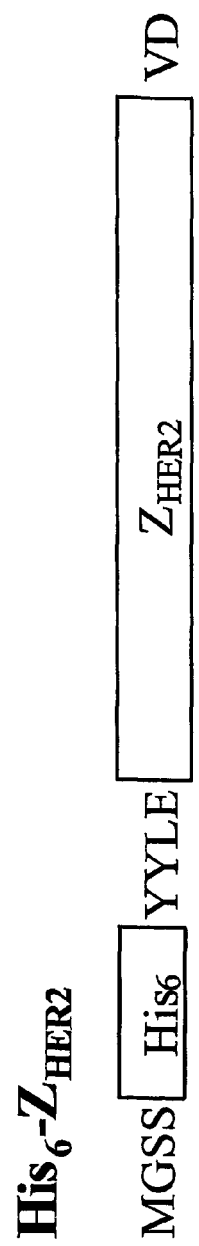
FIG. 2 is a schematic illustration of the amino acid sequence of a fusion polypeptide produced in Example 1. $Z_{HER2}$ represents a HER2 binding domain with a sequence selected from SEQ ID NO:2-3 and His$_6$ represents a hexahistidyl tag.

The invention will now be illustrated further through the non-limiting recital of experiments conducted in accordance therewith.

EXAMPLE 1

Selection and Study of HER2 Binding Polypeptides

In these experiments, several HER2 binding polypeptides according to the invention were selected from a library of a multitude of different SPA domain related polypeptides, and subsequently characterized.

Library Panning and Clone Selection

A combinatorial phage display library was prepared essentially as described in Nord K et al (1995, supra). The pool of this library which was used in the present study comprised $8.7 \times 10^8$ variants of protein Z (Affibody® molecules), with random amino acid residues at positions 9, 10, 11, 13, 14, 17, 18, 24, 25, 27, 28, 32 and 35. Antigen binding Affibody® molecules were selected in four panning cycles using biotinylated human HER2 extracellular domain (HER2-ECD) as the target (recombinant human HER2 extracellular domain, amino acids 238-2109, provided by Fox Chase Cancer Center, Philadelphia, USA). From the outcome of the four selection cycles, 91 clones were picked for phage ELISA in order to perform an analysis of their HER2 binding activity.

Phage ELISA for Analysis of HER2 Binding

Phages from the clones obtained after four rounds of selection were produced in 96 well plates, and an Enzyme Linked ImmunoSorbent Assay (ELISA) was used for screening for phages expressing HER2 binding Affibody® molecules. Single colonies were used to inoculate 250 μl TSB medium (30.0 g Tryptic Soy Broth (Merck), water to a final volume of 1 l, autoclaved) supplemented with 2% glucose and 100 μg/ml ampicillin in a deep well 96 well plate and grown on a shaker over night at 37° C. 5 μl overnight culture was added to 500 μl TSB+YE medium (30.0 g Tryptic Soy Broth (Merck), 5.0 g yeast extract, water to a final volume of 1 l, autoclaved) supplemented with 0.1% glucose and 100 μg/ml ampicillin in a new plate. After growing at 37° C. for 3 h, 0.5 μl of $5 \times 10^{12}$ pfu/ml ($2.5 \times 10^9$ pfu) helper phage M13K07 (New England Biolabs, #NO315S) and 100 μl TSB+YE medium were added to each well, and the plates were incubated without shaking at 37° C. for 30 minutes. 300 μl TSB+YE supplemented with IPTG, kanamycin and ampicillin were added to each well to a final concentration of 1 mM IPTG, 25 μg/ml kanamycin and 100 μg/ml ampicillin, and the plates were incubated on a shaker overnight at 30° C. Cells were pelleted by centrifugation at 2500 g for 15 minutes and supernatants, containing phages expressing Affibody® molecules, were used in ELISA. 100 μl of 4 μg/ml of HER2 in PBS (2.68 mM KCl, 137 nM NaCl, 1.47 mM $KH_2PO_4$, 8.1 mM $Na_2HPO_4$, pH 7.4) were added to a microtiter plate (Nunc #446612) and incubated for 1 month at 4° C. After blocking wells with 2% skim milk powder in PBS (blocking buffer) for 1 h at room temperature, 200 μl phage-containing supernatant and 50 μl 10% blocking buffer were added. The plates were incubated for 2 h at room temperature. A polyclonal antibody (rabbit anti-M13, Abcam #ab6188) was diluted 1:1000 in 2% blocking buffer, and 150 μl were added to each well. The plate was incubated at room temperature for 1 h. A goat anti-rabbit IgG antibody conjugated with alkaline phosphatase (Sigma #A-3687) was diluted 1:10000 in 2% blocking buffer, after which 150 μl were added to each well and incubated for 1 h at room temperature. Developing solution was prepared by dissolving Sigma-104 substrate (Sigma #104-105) in a 1:1 mixture of 1 M diethanolamine, 5 mM $MgCl_2$, pH 9.8 and water (1 tablet/5 ml of 1:1 mixture). Thereafter, 180 μl of the developing solution were added to each well. Wells were washed twice with PBS-T (PBS+0.1% Tween-20) and once with PBS before addition of each new reagent. 25 minutes after addition of substrate, the plates were read at $A_{405}$ in an ELISA spectrophotometer (Basic Sunrise, Tecan).

Phages encoding HER2 binders were identified using a threshold criterion of an ELISA value of $A_{405}$ above 0.5. 48 clones gave an ELISA signal above this value, and were selected for DNA sequence analysis, together with 5 clones selected at random for which no ELISA results were available.

DNA Sequence Analysis

Sequencing of the DNA from the clones isolated according to the procedure above was performed with the ABI PRISM, BigDye Terminator v2.0 Ready Reaction Cycle Sequencing Kit (Applied Biosystems) according to the manufacturer's recommendations. Plasmids were prepared and DNA encoding the Affibody molecules was sequenced using the oligonucleotides RIT-27 (5'-GCTTCCGGCTCGTATGTTGT-GTG- 3') (SEQ ID NO:80) and the biotinylated NOKA-2 (5'-biotin-CGGAACCAGAGCCACCACCGG-3') (SEQ ID NO:81). The sequences were analyzed on an ABI PRISM 3700 Genetic Analyser (Applied Biosystems). From the 53 clones previously selected, several clones were found to encode the same amino acid sequence. Taking these degeneracies into account, four sequences of Affibody molecules expressed by clones selected in the ELISA binding assay are given in FIG. 1 ($Z_{HER2\ A-D}$). and identified in the sequence listing as SEQ ID NO: 2-5.

Figure 3:
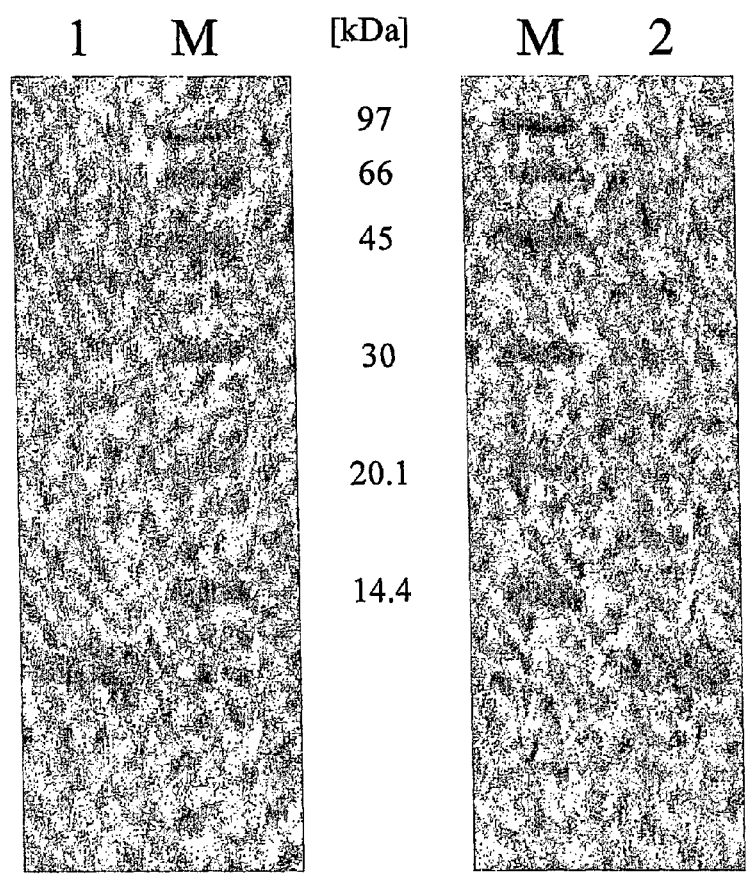
FIG. 3 shows the result of gel electrophoresis of purified fusion proteins. Lane 1: His$_6$-$Z_{HER2\ A}$ (8.7 kDa); Lane 2: His$_6$-$Z_{HER2\ B}$ (8.7 kDa); M: Molecular weight marker (LMW-SDS Marker Kit, Amersham Biosciences #17-0446-01).

Cloning and Protein Production $Z_{HER2}$ polypeptides were expressed in E. coli cells, using expression vectors encoding constructs that are schematically illustrated in FIG. 2. The polypeptides were thereby produced as fusions to an N-terminal hexahistidyl tag. The fusion polypeptides $His_6$-$Z_{HER2\ A}$ and $His_6$-$Z_{HER2\ B}$ were purified on Immobilized Metal ion Affinity Chromatography (IMAC) columns and analyzed on SDS-PAGE. The result of the SDS-PAGE experiment is given in FIG. 3.

Biosensor Analysis of Fusion Polypeptides

Figure 4:
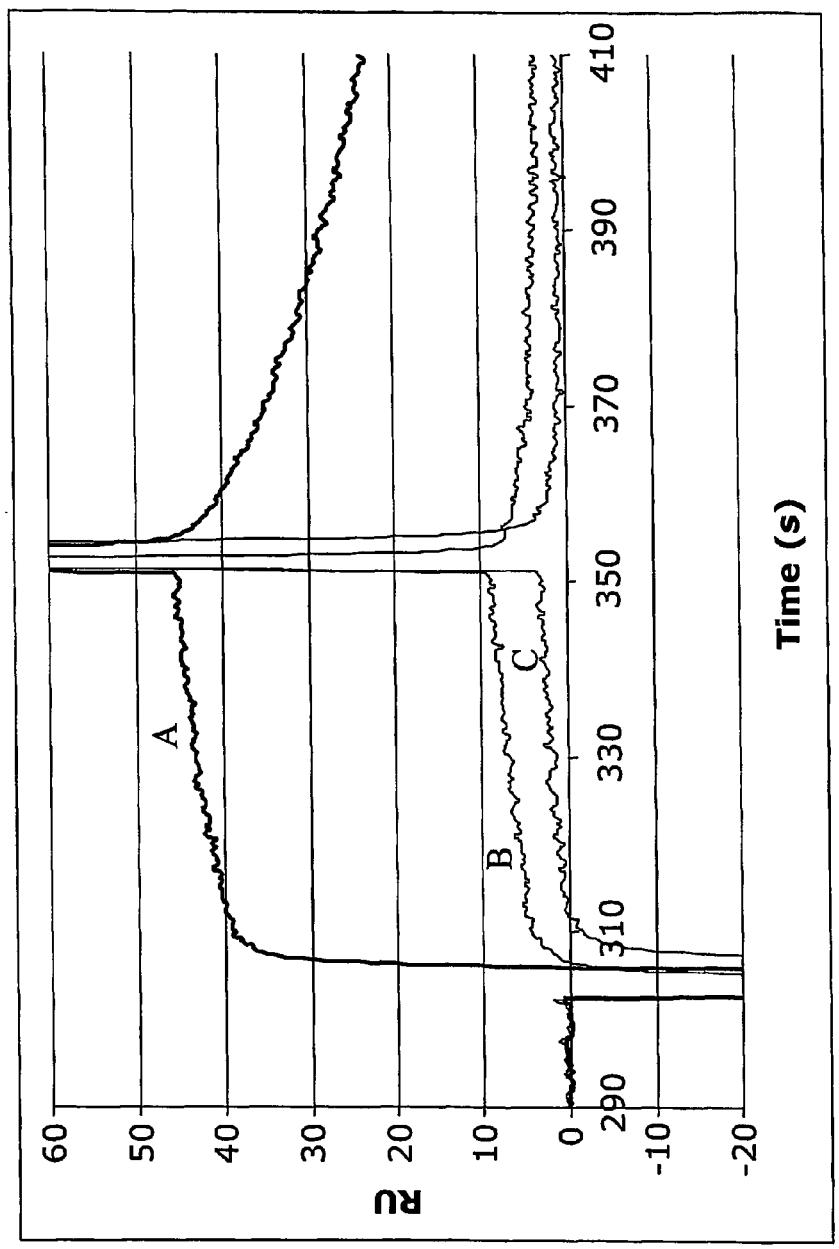
FIG. 4 shows Biacore sensorgrams obtained after injection of 10 μM of the His$_6$-$Z_{HER2\ A}$ fusion protein over sensor chip surfaces having A: HER2, B: HIV-1 gp120, and C: BB immobilized thereto.
Figure 5:
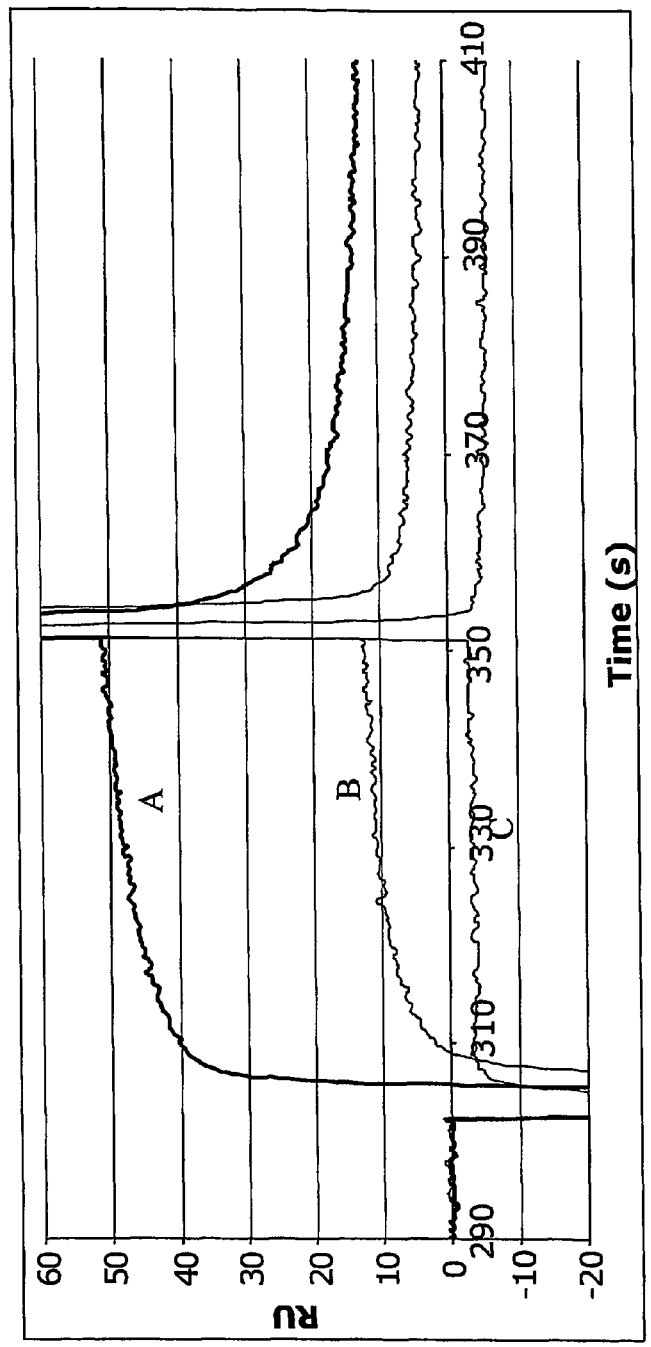
FIG. 5 shows Biacore sensorgrams obtained after injection of 10 μM of the $His_6$-$Z_{HER2\ B}$ fusion protein over sensor chip surfaces having A: HER2, B: HIV-1 gp120, and C: BB immobilized thereto.

The interactions between the His-tagged $Z_{HER2}$ variants produced according to the preceding section and HER2 were analyzed using surface plasmon resonance in a Biacore® 2000 system (Biacore AB, Uppsala, Sweden). Human HER2, HIV-1 gp120 (Protein Sciences Corporation, #2003-MN), and BB (albumin-binding protein derived from streptococcal protein G), the latter two for use as controls, were immobilized in different flow cells by amine coupling onto the carboxylated dextran layer on surfaces of CM-5 chips, according to the manufacturer's recommendations. Immobilization of human HER2, HIV-1 gp120, and BB resulted in 1900, 6290, and 1000 resonance units (RU), respectively. A fourth flow cell surface was activated and deactivated for use as blank during injections. The $His_6$-$Z_{HER2\ A}$ and $His_6$-$Z_{HER2\ B}$ proteins were diluted in HBS (5 mM HEPES, 150 mM NaCl, 3.4 mM EDTA, 0.005% surfactant P-20, pH 7.4) to a final concentration of 10 μM, and injected in random order as duplicates at a constant flow-rate of 30 μl/minute. The ability of the purified proteins $His_6$-$Z_{HER2\ A}$ and $His_6$-$Z_{HER2\ B}$ to interact with HER2 was confirmed, as illustrated by the sensorgrams of FIGS. 4 and 5, respectively.

Figure 6:
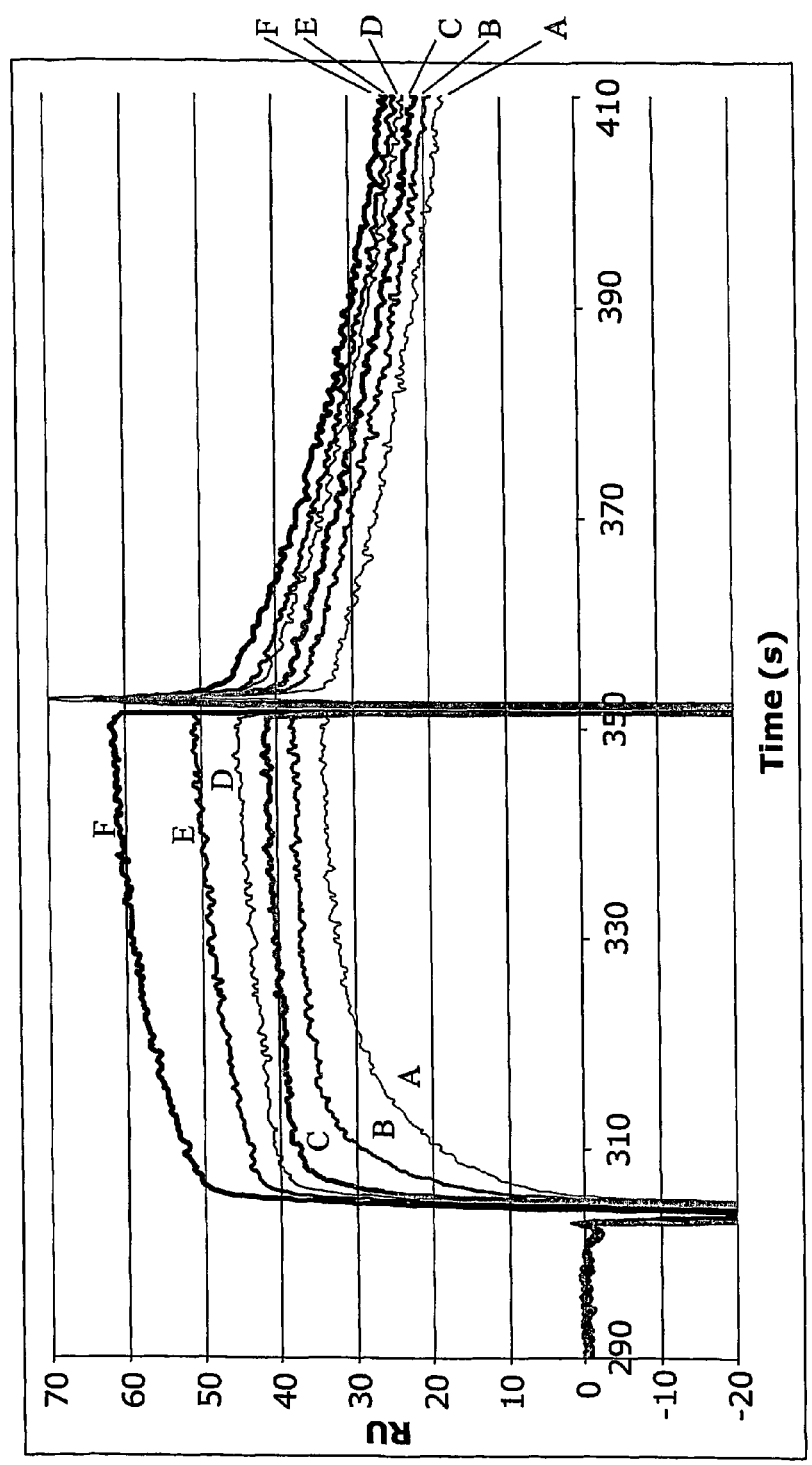
FIG. 6 shows Biacore sensorgrams obtained after injection of A: 1 μM; B: 2 μM; C: 5 μM; D: 10 μM, E: 20 μM; F: 40 μM of the $His_6$-$Z_{HER2\ A}$ fusion protein over a sensor chip surface having HER2 immobilized thereto.
Figure 7:
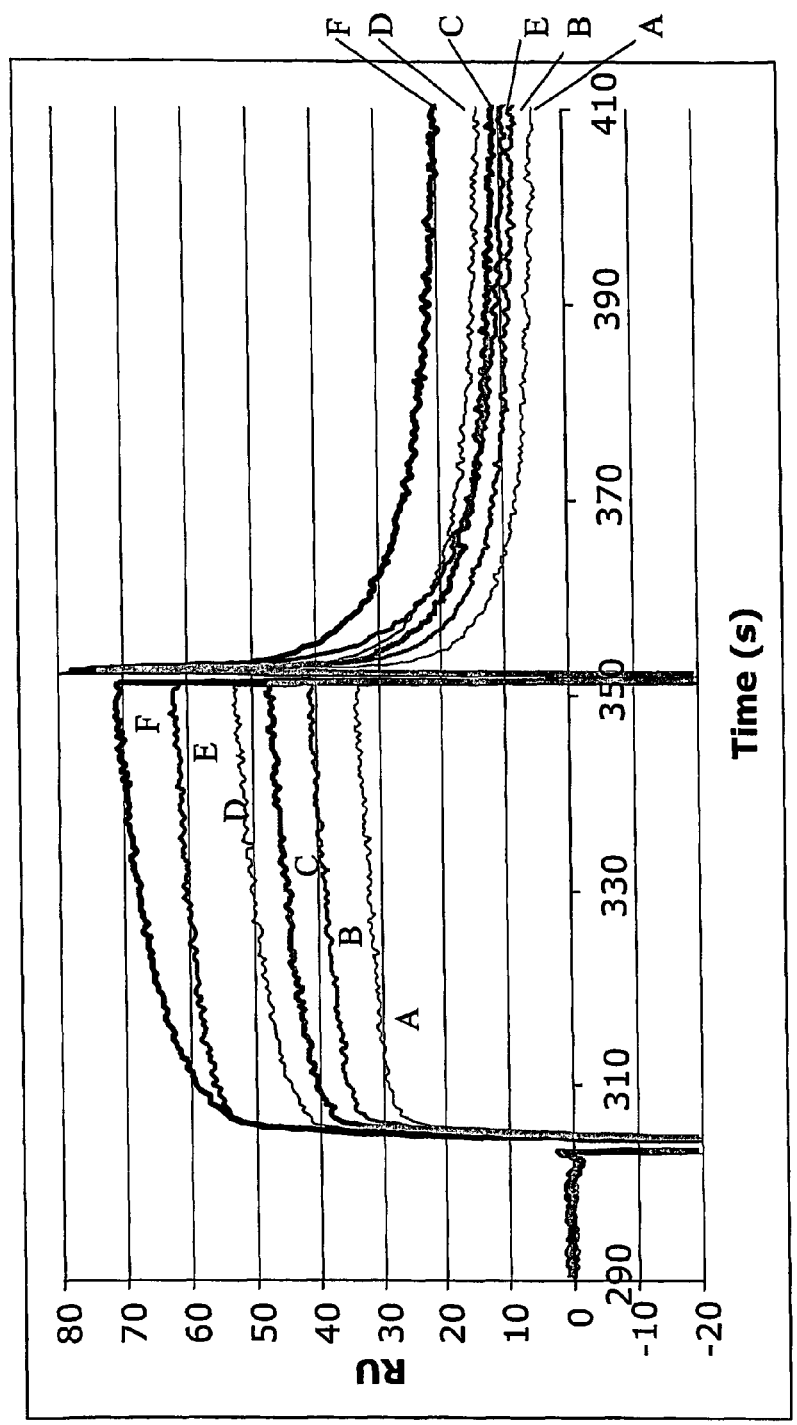
FIG. 7 shows Biacore sensorgrams obtained after injection of A: 1 μM; B: 2 μM; C: 5 μM; D: 10 μM, E: 20 μM; F: 40 μM of the $His_6$-$Z_{HER2\ B}$ fusion protein over a sensor chip surface having HER2 immobilized thereto.

Furthermore, kinetic studies were performed for $His_6$-$Z_{HER2\ A}$ and $His_6$-$Z_{HER2\ B}$. The CM-5 chip having 1900 RU of human HER2 immobilized thereto was used. A series of six different concentrations (1 μM-40 μM) of HER2 binding polypeptide was prepared in HBS for each of $His_6$-$Z_{HER2\ A}$ and $His_6$-$Z_{HER2\ B}$, and injected in random order as duplicates at a flow-rate of 30 μl/minute. The total injection time was 50 seconds (association) followed by a wash during 6 minutes (dissociation). The surfaces were regenerated with 20 mM HCl for 10 seconds. The responses measured in reference cells (activated/deactivated surface) were subtracted from the response measured in the cells with immobilized HER2. The binding curves (sensorgrams) were analyzed using the 1:1 Langmuir binding model of the BIAevaluation 3.0.2 software (Biacore AB). As is clear from the binding curves presented in FIGS. 6 (His$_6$-Z$_{HER2\ A}$) and 7 (His$_6$-Z$_{HER2\ B}$), His$_6$-Z$_{HER2\ A}$ and His$_6$-Z$_{HER2\ B}$ both clearly bind to HER2, as evidenced by the association and dissociation curves with an indicated $K_D$ of 10-100 nM for His$_6$-Z$_{HER2\ A}$ and 200-400 mM for His$_6$-Z$_{HER2\ B}$. Furthermore, the binding is selective, since neither of the HER2 binding polypeptides studied bind to the BB and gp120 control antigens (FIGS. 4 and 5).

Figure 8A:
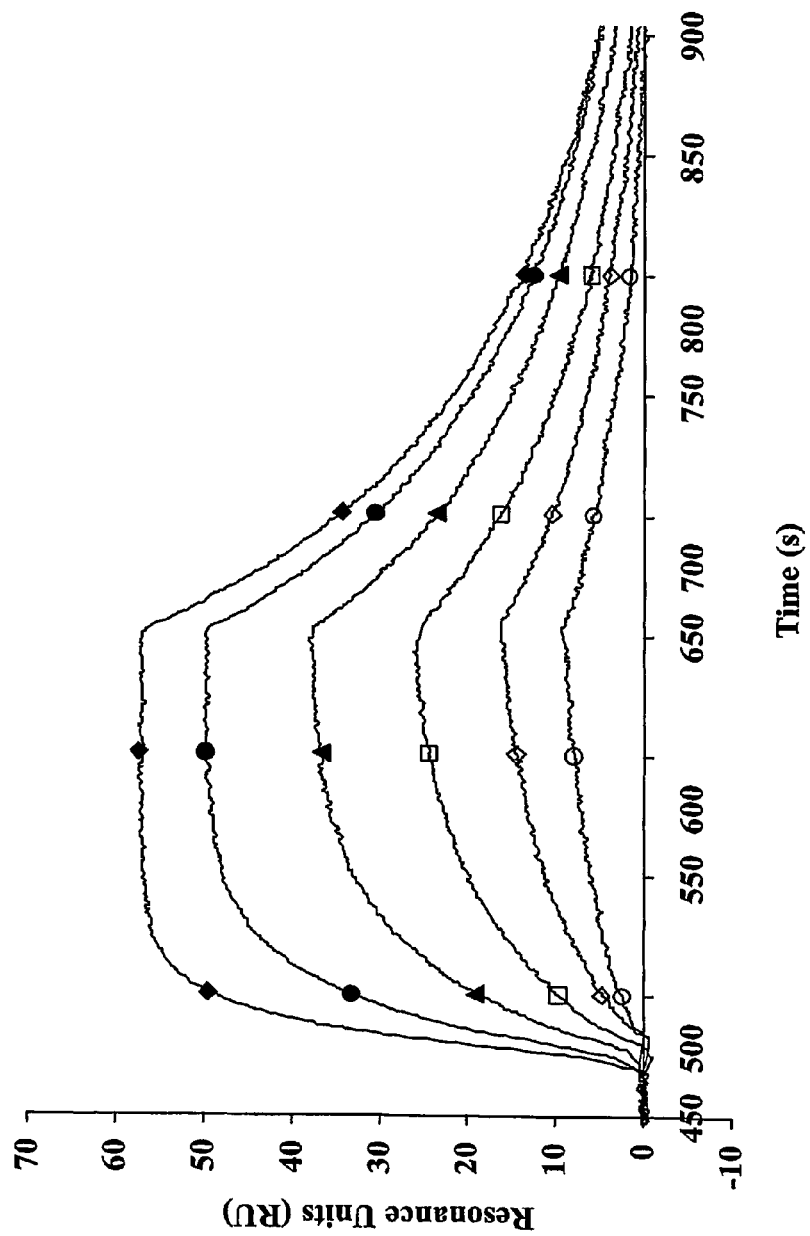
FIG. 8A shows Biacore sensorgrams obtained after injection of $His_6$-$Z_{HER2\ A}$ over a HER2-ECD flow-cell surface at selected concentrations; 312.5 nM (filled diamonds), 156.3 nM (filled circles), 78.2 nM (filled triangles), 39.1 nM (open squares), 19.6 nM (open diamonds), and 9.8 nM (open circles).
Figure 8B:
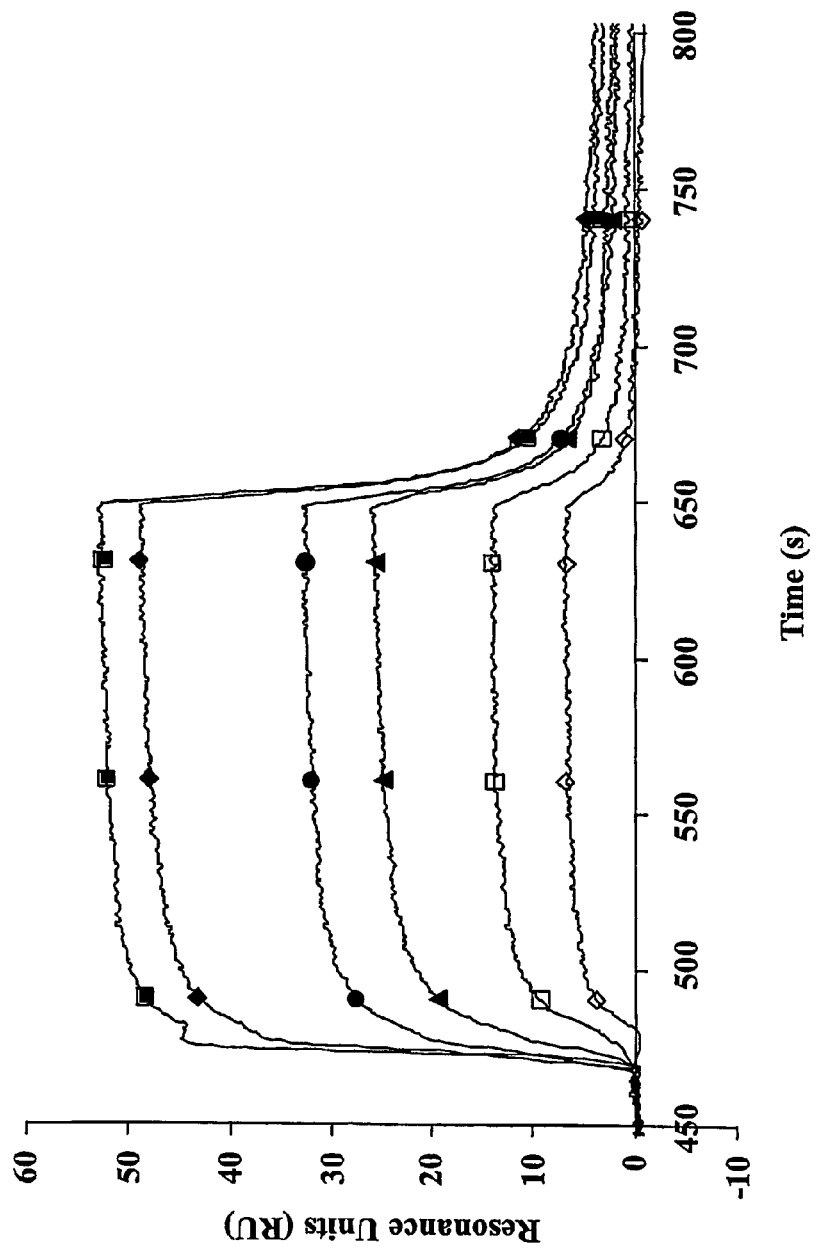
FIG. 8B shows Biacore sensorgrams obtained after injection of $His_6$-$Z_{HER2\ B}$ over a HER2-ECD flow-cell surface at selected concentrations; 625 nM (filled squares), 312.5 mM (filled diamonds), 156.3 nM (filled circles), 78.2 nM (filled triangles), 39.1 nM (open squares), and 19.6 nM (open diamonds).

In a second kinetic experiment, the His$_6$-Z$_{HER2\ A}$ and His$_6$-Z$_{HER2\ B}$ variants were again injected over the HER2 surface at different concentrations (0-5 μM, with 0.0098 μM as the lowest concentration for His$_6$-Z$_{HER2\ A}$ and 0.0196 μM for His$_6$-Z$_{HER2\ B}$, diluted in HBS) with a flow rate of 30 μl/min. Prior to the kinetic analysis, the protein concentration had been determined by amino acid analysis. The dissociation equilibrium constant ($K_D$), the association rate constant ($k_a$), and the dissociation rate constant ($k_d$) were calculated using BIAevaluation 3.2 software (Biacore), assuming a one-to-one binding. For the first two Biacore analyses, the samples were run at 25° C. in duplicates in random order, and after each injection the flow cells were regenerated by the injection of 10 mM HCl. Upon evaluation of the binding curves (FIG. 8A-8B), the dissociation equilibrium constant ($K_D$) was determined to be about 50 nM for His$_6$-Z$_{HER2\ A}$ and about 140 nM for His$_6$-Z$_{HER2\ B}$. The reason for the difference in $K_D$ is most likely due to the marked difference in dissociation rate, as can be seen by comparing FIG. 4, diagram A with FIG. 5, diagram A. For His$_6$-Z$_{HER2\ A}$, the association rate constant ($k_a$) was calculated to be about $1.8\times10^5$ M$^{-1}$ s$^{-1}$ and the dissociation rate constant ($k_d$) about $9.9\times10^{-3}$ s$^{-1}$, while for His$_6$-Z$_{HER2\ B}$, $k_a$ and $k_d$ were difficult to estimate due to the fast association and dissociation kinetics. Thus, the His$_6$-Z$_{HER2\ A}$ affibody variant, showing stronger binding to its target, was selected for further characterization.

EXAMPLE 2

Binding of Z$_{HER2\ A}$ to Cells Expressing HER2

Cell Culture

The human breast cancer cell line SKBR-3, known to express about $2\times10^6$ HER2 molecules per cell, was purchased from ATCC (ATCC #HTB-30). The cells were cultured in RPMI 1640 medium supplemented with 10% fetal bovine serum, 2 mM L-glutamine, and PEST (100 IU/ml penicillin and 100 μg/ml streptomycin), all from Biochrom KG (Berlin, Germany). The cells were cultured at 37° C. in humidified air containing 5% CO$_2$, and seeded in 3 cm petri dishes three days before the experiment.

Radiolabeling

Labeling precursor, N-succinimidyl p-(trimethylstannyl) benzoate (SPMB), was prepared according to Orlova et al in Nucl Med Biol 27:827-835 (2000), and 5 μg of SPMB was added to 5 MBq of $^{125}$I in a 5% solution of acetic acid. To start the reaction, 40 μg of chloramine-T (Sigma, St. Louis, Mo.) in aqueous solution was added. The reaction mixture was agitated for 5 min, and 80 μg of sodium-meta-bisulphate (Aldrich, Steinheim, Germany) in aqueous solution was added to stop the reaction. The radiolabeled precursor was added to 40 μg of His$_6$-Z$_{HER2\ A}$ or His$_6$-Z$_{HER2\ B}$ in 0.07 M borate buffer, pH 9.2. The coupling reaction was performed at room temperature for 45 min with continuous shaking. Labeled Z$_{HER2}$ variants were separated from low molecular weight products using a NAP™-5 size exclusion column (Amersham Biosciences) equilibrated with PBS. The radiolabeled Z$_{HER2}$ variants were then analyzed using Biacore technology to verify that the labeling procedure had not affected the binding affinity towards HER2-ECD. Both Z$_{HER2}$ variants showed retained affinity (data not shown).

Cellular Tests

To each dish of about 100000 SKBR-3 cells, 14 ng of labeled His$_6$-Z$_{HER2\ A}$ or His$_6$-Z$_{HER2\ B}$ in 1 ml complemented medium was added. This amount corresponds to a theoretical ligand:receptor ratio of 5:1. Three dishes without cells were treated in the same way, in order to determine unspecific binding not derived from cells. This value was subtracted from all others. To analyze the specificity of cell binding, three dishes were treated not only with labeled Z$_{HER2}$ variants, but also with a 500-fold excess of unlabeled Z$_{HER2}$ variants. After three hours of incubation at 37° C., the radioactive medium was removed and the dishes were washed rapidly three times with ice-cold serum-free medium. Cells were trypsinated with 0.5 ml Trypsin/EDTA solution (0.25%/0.02% in PBS; Biochrom KG, Berlin, Germany) for 15 min at 37° C. The cells were then resuspended in 1 ml complemented medium, and 0.5 ml of the cell suspension was used for cell counting and the remaining 1 ml was used for radioactivity measurement in an automated γ counter.

Figure 9:
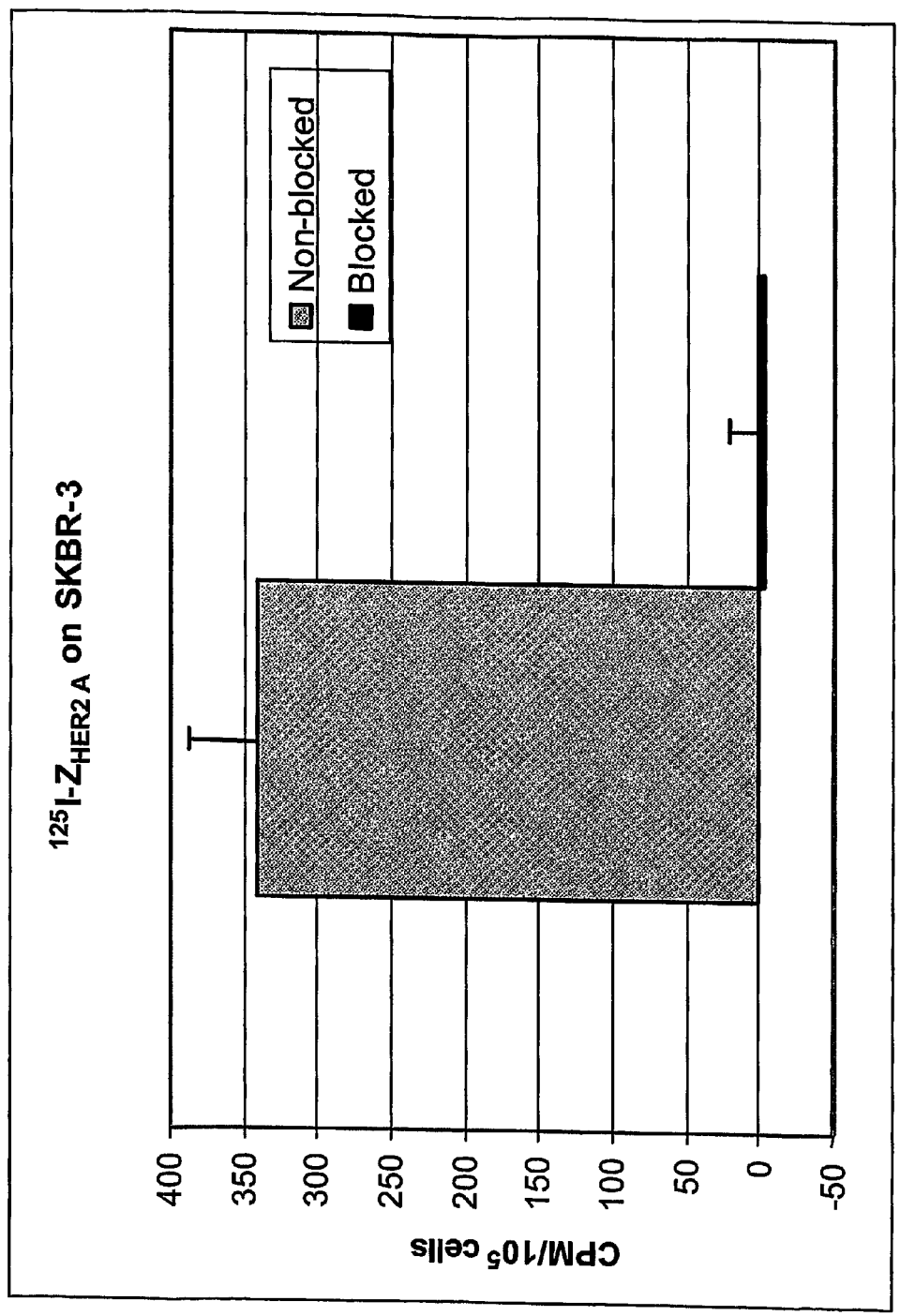
FIG. 9 shows specificity of the $His_6$-$Z_{HER2\ A}$ binding to SKBR-3 cells. $^{125}$I-labelled $His_6$-$Z_{HER2\ A}$ was allowed to bind to SKBR-3 cells with an estimated theoretical ligand: HER2 receptor ratio of 5:1. Values are means of three measurements. Error bars represent standard deviations.

As presented in FIG. 9, His$_6$-Z$_{HER2\ A}$ showed specific binding to SKBR-3 cells, known to express $2\times10^6$ HER2 receptors per cell ("non-blocked" bar). The binding of radiolabeled His$_6$-Z$_{HER2\ A}$ could be totally blocked by the addition of an excess of non-labeled His$_6$-Z$_{HER2\ A}$ ("blocked" bar). However, the binding of His$_6$-Z$_{HER2\ B}$ to SKBR-3 cells was below the detection limit (data not shown), probably as a result of the faster dissociation rate for this Z$_{HER2}$ variant (cf above).

EXAMPLE 3

Expression and Characterization of Dimers of HER2 Binding Polypeptides

DNA Construction and Protein Production

The selection of a novel affibody ligand, denoted His$_6$-Z$_{HER2\ A}$ and having affinity for the HER2 receptor, was described above. A dimeric Z$_{HER2}$ variant was constructed by subcloning the gene fragment encoding the Z$_{HER2\ A}$ polypeptide into the expression vector for His$_6$-Z$_{HER2\ A}$. The introduced Z$_{HER2\ A}$ fragment was verified by DNA sequencing on a DNA sequencer ABI Prisms 3700 Analyzer (Applied Biosystems, Foster City, Calif.). The *Escherichia coli* strain RR1ΔM15 (Rüther, Nucleic Acids Res 10:5765-5772 (1982)) was used as bacterial host during the cloning procedure. The resulting vector encodes, under the control of the T7 promoter (Studier et al, Methods Enzymol 185:60-89 (1990)), a dimeric Z$_{HER2}$ variant, (Z$_{HER2\ A}$)$_2$, fused to an N-terminal hexahistidyl (His$_6$) tag, which allows purification by immobilized metal ion affinity chromatography (IMAC).

Figure 10:
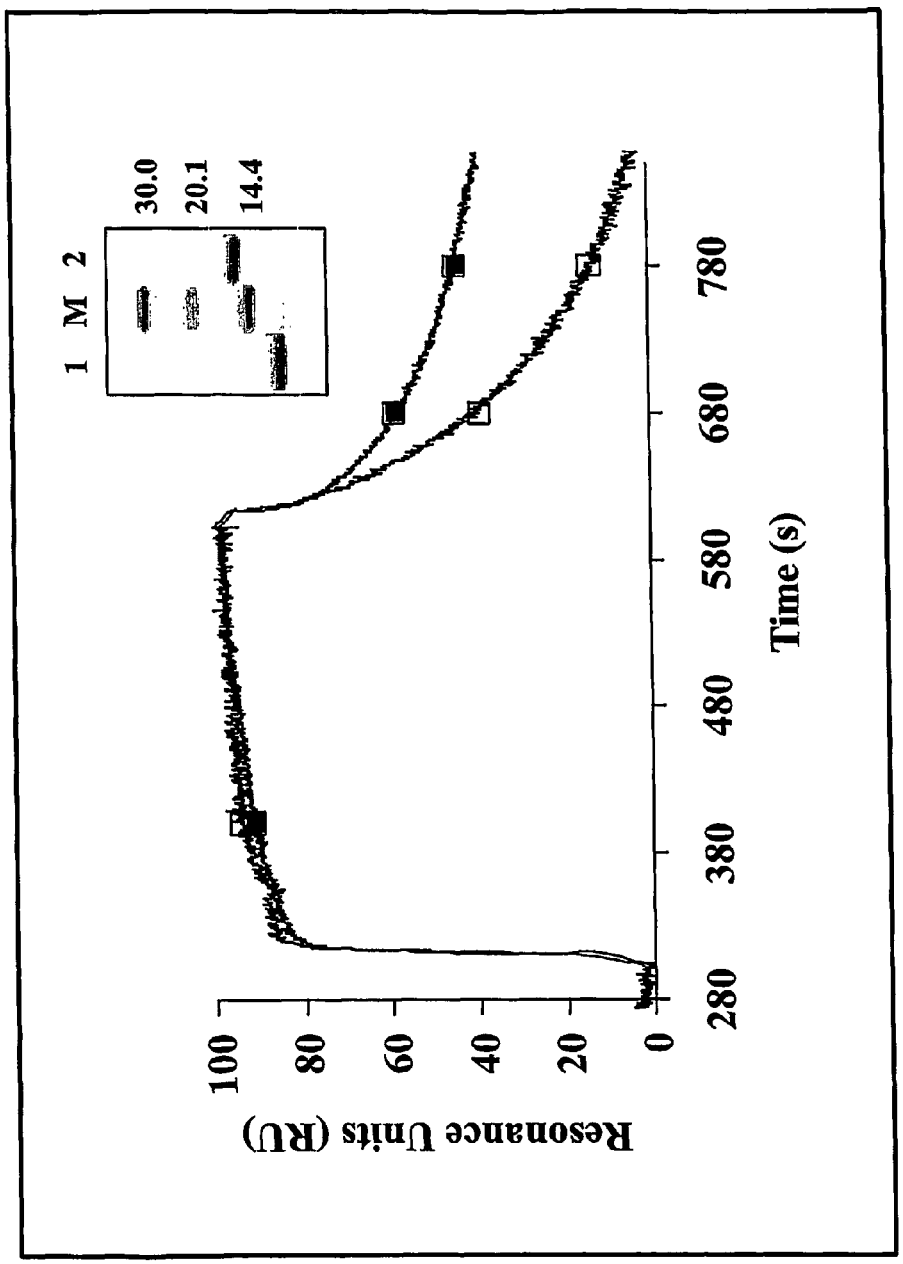
FIG. 10 shows Biacore sensorgrams obtained after injection of purified $His_6$-$Z_{HER2\ A}$ (open squares) and $His_6$-$(Z_{HER2\ A})_2$ (filled squares) over a sensor chip flow-cell surface containing amine-coupled HER2-ECD. The y values of the curves have been normalized to between 0 and 100 Resonance Units. The inserted SDS-PAGE gel (Tris-Glycine 16% homogenous gel, reducing conditions) shows the expressed and IMAC-purified $His_6$-$Z_{HER2\ A}$ (lane 1) and $His_6$-$(Z_{HER2\ A})_2$ (lane 2). Lane M, marker proteins with molecular masses in kilodaltons.

The dimeric Z$_{HER2}$ variant was expressed as a His$_6$-tagged fusion protein in *E. coli* strain BL21 (DE3), and recovered by IMAC purification on a Talon Metal Affinity Resin (8901-2, BD Biosciences, CA) column under denaturing conditions, as described for the monomeric polypeptides in Example 1. Renaturation of the purified His$_6$-(Z$_{HER2\ A}$)$_2$ fusion protein was performed by gel filtration using PD-10 columns, equilibrated with PBS (10 mM phosphate, 154 mM NaCl, pH 7.1), according to the manufacturer's protocol (Amersham Biosciences). Protein concentration was calculated from absorbance measurements at 280 nm, using the appropriate extinction coefficient (30440 M$^{-1}$ cm$^{-1}$), and also verified by amino acid analysis (Aminosyraanalyscentralen, Uppsala, Sweden). The purified protein was further analyzed by SDS-PAGE on a Tris-Glycine 16% homogenous gel, using a Novex system (Novex, CA, USA). Protein bands were visualized with Coomassie Brilliant Blue staining. Upon SDS-PAGE analysis, the protein was observed as a specific band of the expected molecular weight (15.6 kD) (FIG. 10, Lane 2 of insert). Estimations from absorbance measurements at 280 nm demonstrated an expression level of about 200 mg/l of cell culture.

Biosensor Analysis

A Biacore® 2000 instrument (Biacore AB) was used for real-time biospecific interaction analysis (BIA). A recombinant extracellular domain of HER2 (HER2-ECD), diluted in 10 mM NaAc, pH 4.5, was immobilized (about 2200 RU) on the carboxylated dextran layer of one flow-cell surface of a CM5 sensor chip (research grade) (BR-1000-14, Biacore AB) by amine coupling according to the manufacturer's instructions. Another flow-cell surface was activated and deactivated, to serve as a reference surface. For the $Z_{HER2}$ sample, the buffer was changed to HBS (5mM HEPES, 150 mM NaCl, 3.4 mM EDTA, 0.005% surfactant P20, pH 7.4) be gel filtration using a NAP™ -10 column, according to the manufacturer's protocol (Amersham Biosciences), and the sample was thereafter filtrated (0.45 μm, Millipore, Billerica, MA). Binding analyses were performed at 25 °C., and HBS was used as running buffer. For all Biacore analyses, the samples were run in duplicates in random order, and after each injection the flow cells were regenerated by the injection of 10 mM HCl.

In a first experiment, difference in binding to HER2-ECD between the monomeric and the dimeric $Z_{HER2}$ proteins (His$_6$-$Z_{HER2\ A}$ of Example 1 and His$_6$-$(Z_{HER2\ A})_2$) was tested by injection of 5 μM of each protein over the HER2-ECD surface, with a flow rate of 5 μl/min. As can be seen in FIG. 10, a slower off-rate was observed for His$_6$-$(Z_{HER2\ A})_2$, indicating a stronger binding between HER-ECD and His$_6$-$(Z_{HER2\ A})_2$, compared to His$_6$-$Z_{HER2\ A}$.

In a second experiment, His$_6$-$(Z_{HER2}A)_2$ was subjected to a kinetic analysis, in which the protein was injected over the HER2-ECD surface at different concentrations (0-5 μM, with 0.0049 μM as the lowest concentration, diluted in HBS) with a flow rate of 30 μl/min. Prior to the kinetic analysis, the protein concentration had been determined by amino acid analysis. The dissociation equilibrium constant ($K_D$), the association rate constant ($k_a$), and the dissociation rate constant ($k_d$) were calculated using BIAevaluation 3.2 software (Biacore AB), assuming 1:1 binding. Upon evaluation of the binding curves, the dissociation equilibrium constant ($K_D$) was determined to be about 3 nM, the association rate constant ($k_a$) was calculated to be about $2.5 \times 10^5$ $M^1$ $s^{-1}$ and the dissociation rate constant ($k_d$) about $7.6 \times 10^{-4}$ $s^{-1}$. These values can be compared to the kinetic constants obtained for the monomeric His$_6$-$Z_{HER2\ A}$ of Example 1, confirming the stronger binding of the dimeric His$_6$-$(Z_{HER2\ A})_2$. Such improved apparent higher affinity, due to avidity effects for the dimeric constructs, have been demonstrated earlier for other Affibody® molecules (Gunneriusson E et al, Protein Eng 12:873-878 (1999)).

EXAMPLE 4

Biodistribution and Tumor Targeting with $(Z_{HER2\ A})_2$ in Nude Mice Bearing SKOV-3 Xenografts In the experiments making up this example, the His$_6$-tagged dimeric $(Z_{HER2\ A})_2$ polypeptide according to Example 3 was radiolabeled with $^{125}$I and injected into mice bearing a grafted tumor characterized by HER2 overexpression. Studies of the biodistribution of the polypeptide were conducted, as well as imaging of the injected mice to study localization of the labeled polypeptide. A labeled Z domain derivative with binding affinity for Taq DNA polymerase was used as control without specificity for HER2 ($Z_{Taq}$; described in Gunneriusson E et al, supra and referred to therein as $Z_{Taq\ S1-1}$).

Materials and Methods

Indirect Radioiodination of $(Z_{HER2\ A})_2$

A volume of 2.3 μl $^{125}$I (corresponding to 10 MBq) (Na [$^{125}$I], Amersham Biosciences, Uppsala, Sweden) was added to a siliconized microcentrifuge tube. 10 μl acetic acid (0.1% in water), 5 μl N-succinimidyl p-trimethylstannyl-benzoate (1 mg/ml in 5% acetic acid in methanol) (prepared according to Koziorowski J et al, Appl Radiat Isot 49:955-959 (1998)) and 10 μl Chloramine-T (4 mg/ml in water) ($CH_3C_6H_4SO_2N$(Cl)Na.3$H_2O$, Sigma, St Louis, Mo., USA) was added. The reaction was allowed to take place for five minutes with some mixing. The reaction was then terminated with 10 μl sodium metabisulfate (8 mg/ml in water) ($Na_2S_2O_5$, Sigma, St Louis, Mo., USA). A volume of 40 μl $(Z_{HER2\ A})_2$ dimer (0.25 mg/ml in 0.07 M borate buffer, pH 9.2 (sodium borate, $Na_2B_4O_7.10H_2O$, Sigma, St Louis, Mo., USA, and hydrochloric acid, HCl, Merck, Darmstadt, Germany)) was added to the reaction tube. Another 40 μl of borate buffer was added to each tube in order to raise the pH to about 9. After a reaction time of 45 minutes with continuous shaking, the reaction components were separated on NAP-5 size exclusion columns (Amersham Biosciences, Uppsala, Sweden) equilibrated with PBS according to the manufacturer's protocol. The reaction tube, void fraction, high MW fraction, low MW fraction and column were measured at 60 cm ($^{125}$I) with a handheld γdetector (Mini-instruments Ltd, Essex, UK) in order to calculate the labeling yield. The high molecular weight fraction was stored in siliconized microcentrifuge tube at −20° C. until use the following day. The obtained yield was 25-30%.

Indirect Radioiodination of $Z_{Taq}$

A stock solution of [$^{125}$I]-NaI was mixed with 10 μl 0.1% aqueous solution of acetic acid, 5 μl of N-succinimidyl p-trimethylstannyl-benzoate solution (1 mg/ml in 5% acetic acid in methanol), and 10 μl aqueous solution of Chloramine-T (4 mg/ml). The reaction mixture was vigorously vortexed, and incubated during 5 min at room temperature with shaking. The reaction was quenched with 10 μl aqueous solution of sodium metabisulfite (8 mg/ml). 21 μl solution of $Z_{Taq}$ in PBS (2.4 mg/ml) was added to the crude reaction mixture. The pH of the reaction mixture pH was adjusted to about 9 by addition of borate buffer (0.1 M, pH 9.15). The reaction mixture was incubated at room temperature during 30 min with shaking, and separated into high molecular weight fraction (labeled $Z_{Taq}$) and low molecular weight fraction on a NAP-5 column pre-equilibrated with 5% albumin (bovine, fraction V, Sigma, St. Louis, Mo., USA) in PBS, using PBS as eluent. The obtained radiochemical yield was between 75% and 80%. The specific radioactivity was 100 kBq/μg.

Animal Preparation

Female outbred nu/nu balb mice from M&B (10-12 weeks old when arrived) were used under permission C181/1. Mice were acclimatized in the animal facilities of the Rudbeck laboratory, Uppsala, Sweden, using standard diet, bedding and environment during the week before xenografts were established in them. The mice had free access to food and drinking water.

Two months before the first experiment, $5 \times 10^6$ SKOV-3 human ovarian cancer cells (ATCC #HTB-77) were injected subcutaneously in the right hind leg of 33 mice. This group is denoted "Set A".

Three weeks before the second experiment, $10^7$ SKOV-3 cells were injected subcutaneously in both hind legs of 32 mice. This group is denoted "Set B".

For imaging studies, two mice with big tumors (see below) were taken from Set A and all others from Set B.

By the time of the experiments, tumors had been established in all mice, but were rather small and differed in size and status (encapsulated and invasive, stage of vascularization). At the time of use, all mice weighed 22-27 g.

Biodistribution Experiment I 20 mice from Set A were randomly divided into 5 groups (I-V) with 4 mice in each group. 2 mice from Set A with bigger tumors were excluded for use in imaging studies. Groups, injections and times of sacrifice were according to Scheme 1.

The mice were injected iv in the tail with 0.5 µg $(Z_{HER2\ A})_2$, indirectly labeled with $^{125}$I (100 kBq per mouse) in 50 µl PBS. Mice in group II ("blocked group") were pre-injected sc with 0.05 mg of unlabeled $(Z_{HER2\ A})_2$ in 200 µl PBS, 45 min before the injection of labeled $(Z_{HER2\ A})_2$. All injections were tolerated well, judging by the lack of any visible problems.

Scheme 1

| Group | Mouse ID | Additional treatment | Time of sacrifice post injection (h) |
|---|---|---|---|
| I | 1-4 | | 1 |
| II | 5-8 | Unlabeled $(Z_{HER2\ A})_2$ | 1 |
| III | 9-12 | | 4 |
| IV | 13-16 | | 8 |
| V | 17-20 | | 24 |

5 min before the time of sacrifice, mice were injected ip with a lethal dose of Ketalar/Rompun solution (20 µl/g body weight, Ketalar 10 mg/ml (Pfizer, New York, USA), Rompun 1 mg/ml (Bayer, Leverkusen, Germany)). Blood was taken at the time of sacrifice by heart puncture with a 1 ml syringe washed with diluted heparin (5000 IE/ml, Leo Pharma, Copenhagen, Denmark). Blood, samples of urine, muscle, bone, large and small intestines, heart, bladder, lung, liver, spleen, pancreas, kidney, stomach, salivary and thyroid glands, brain, tumors and tails were dissected and collected in weighed 20 ml plastic bottles. In the case of multiple tumors in some mice from Set B, every tumor was collected in a separate bottle. The samples of organs and tissue were weighed, and their radioactivity measured with a γ-counter (Automated γ-counter with a 3-inch NaI(Tl) detector, 1480 Wallac WIZARD, Wallac O Y, Turku, Finland).

Biodistribution Experiment II 24 mice from Set B were randomly divided into 6 groups with 4 mice in each group. 8 mice from Set B with bigger tumors were selected for use in imaging studies. Groups, injections and times of sacrifice were according to Scheme 2.

The mice of groups I and IV-VI were injected iv in the tail with 0.5 µg $(Z_{HER2\ A})_2$, indirectly labeled with $^{125}$I (100 kBq per mouse) in 50 µl PBS. The mice of group II were injected with the same amount of radioiodinated $(Z_{HER2\ A})_2$, but subcutaneously in the tail. The mice of group III ("negative control group") were injected iv in the tail with 1.07 µg $Z_{Taq}$ indirectly labeled with $^{125}$I (100 kBq per mouse) in 50 µl PBS. All injections were tolerated well, judging by the lack of any visible problems.

Scheme 2

| Group | Mouse ID | Additional treatment | Time of sacrifice post injection (h) |
|---|---|---|---|
| I | 1-4 | | 4 |
| II | 5-8 | | 4 |
| III | 9-12 | Labeled $Z_{Taq}$ | 4 |
| IV | 13-16 | | 6 |
| V | 17-20 | | 10 |
| VI | 21-24 | | 15 |

Sacrifice and taking of samples were performed as described above for Biodistribution Experiment I. In this second experiment, the carcass was also collected and its radioactivity content measured. The samples of organs and tissue were weighed, and their radioactivity measured with a γ-counter.

Measurement of Radioactivity

A standard protocol for measurement of $^{125}$I was used. Counts per minute corrected with background level were used for the evaluation. The tissue uptake value, expressed as % ID/g, percent injected dose per gram tissue, was calculated as $$\% \ ID/g = \frac{\text{tissue radioactivity/injected radioactivity}}{\text{tissue weight}} \times 100$$

wherein for iv injections:

Injected radioactivity=Average radioactivity in control syringes−Radioactivity in used syringe−Radioactivity in tail and for sc injections:

Injected radioactivity=Average radioactivity in control syringes−Radioactivity in used syringe Imaging Study For the imaging, mice were divided in two groups with 5 mice in each, taking into account that every group would comprise one mouse with a big tumor from Set A. Mice from Set B were randomized. The two groups of mice were injected with 2.3 µg $(Z_{HER2\ A})_2$ indirectly labeled with $^{125}$I (2.9 MBq per mouse) in 90 µl PBS 6 h or 8 h before imaging, respectively. All injections were tolerated well, judging by the lack of any visible problems.

Whole body imaging of the mice was performed at 6 and 8 h post injection (pi) of radioconjugate. Mice were forced to urinate, anesthetized with lethal Ketalar/Rompun injection ip and killed by cervical dislocation. Mice (5 in each group) were placed in an e.CAM γ-camera (Siemens, Germany), and 10 min images were obtained at each time point. Two mice with bigger tumors (1 from each group) were selected for a special image in the same camera, with an exposure of 20 min. The images were acquired in a 256×256-bit matrix with a low energy, high resolution collimator in a 35 keV energy window with 99% window size. The images were evaluated with the aid of Hermes software from Nuclear Diagnostics (Kent, UK).

Results

Blocking Experiment

Figure 11:
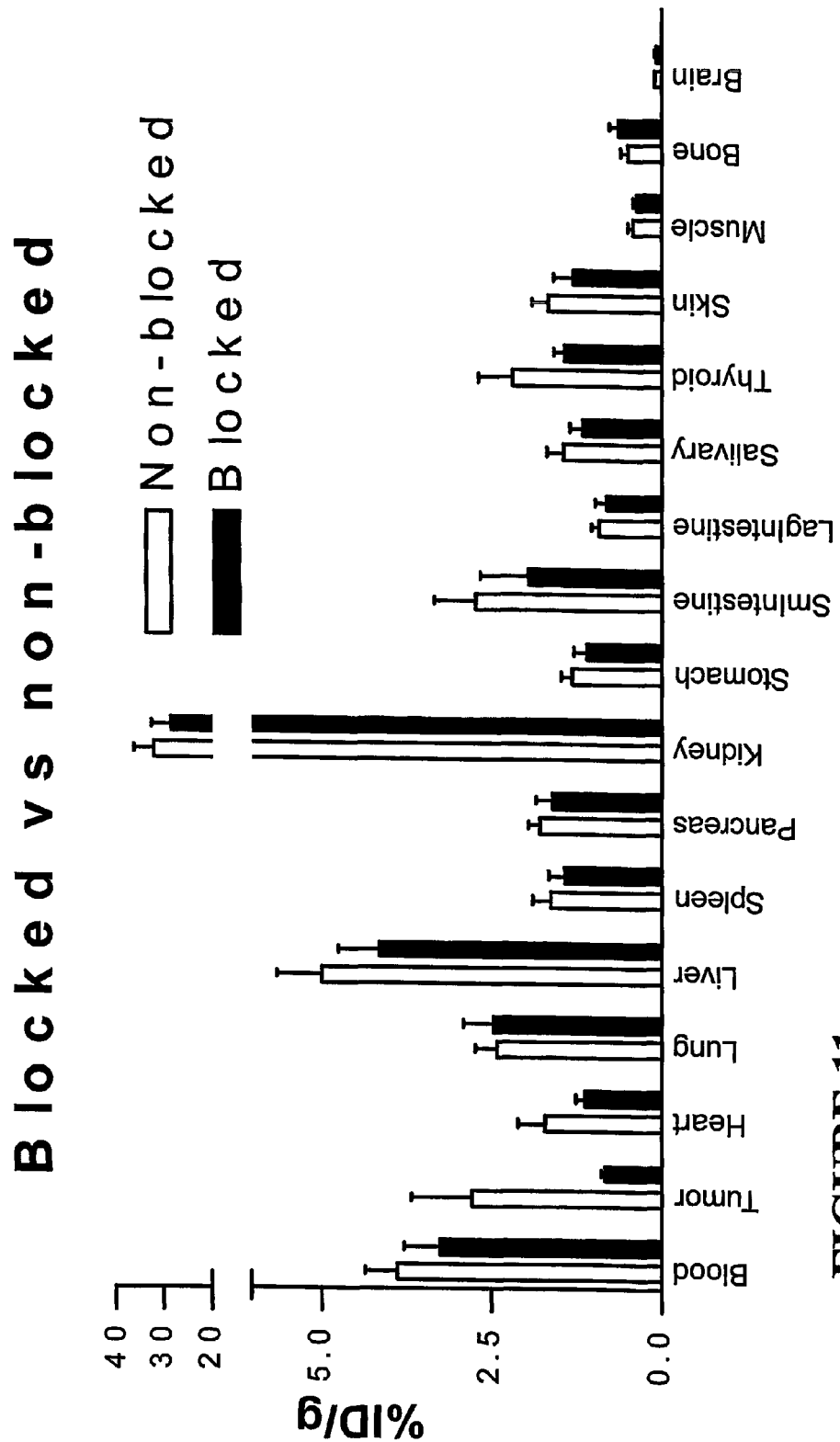
FIG. 11 shows a comparison of biodistribution of radioactivity in tumor bearing nude mice 1 h after injection of $^{125}$I-benzoate-$(Z_{HER2\ A})_2$. Blocked: Data for mice pre-injected with non-labeled $(Z_{HER2\ A})_2$. Non-blocked: Data for mice without pre-injection.

The blocking experiment in Biodistribution Experiment I was performed in order to establish whether uptake of $(Z_{HER2\ A})_2$ in tumors was specific and receptor regulated. Before the major iv injection of radioiodinated dimer, 0.05 mg of unlabeled $(Z_{HER2\ A})_2$ was injected sc in the mice of group II of Scheme 1. Uptake of radioactivity at 1 h post injection in group I and group II was compared. Tumor to blood ratios for the two groups of mice were 0.72 (group I, average) and 0.25 (group II, average) (FIG. 11). However, the difference in uptake was not significant (p=0.16). In all organs except the tumor, radioactivity uptake was the same for both blocked and non-blocked animals.

The rather low tumor to blood ratio in the case of non-blocked mice can be explained by the early time point (1 h pi) chosen for this experiment.

Specificity of Uptake

Figure 12:
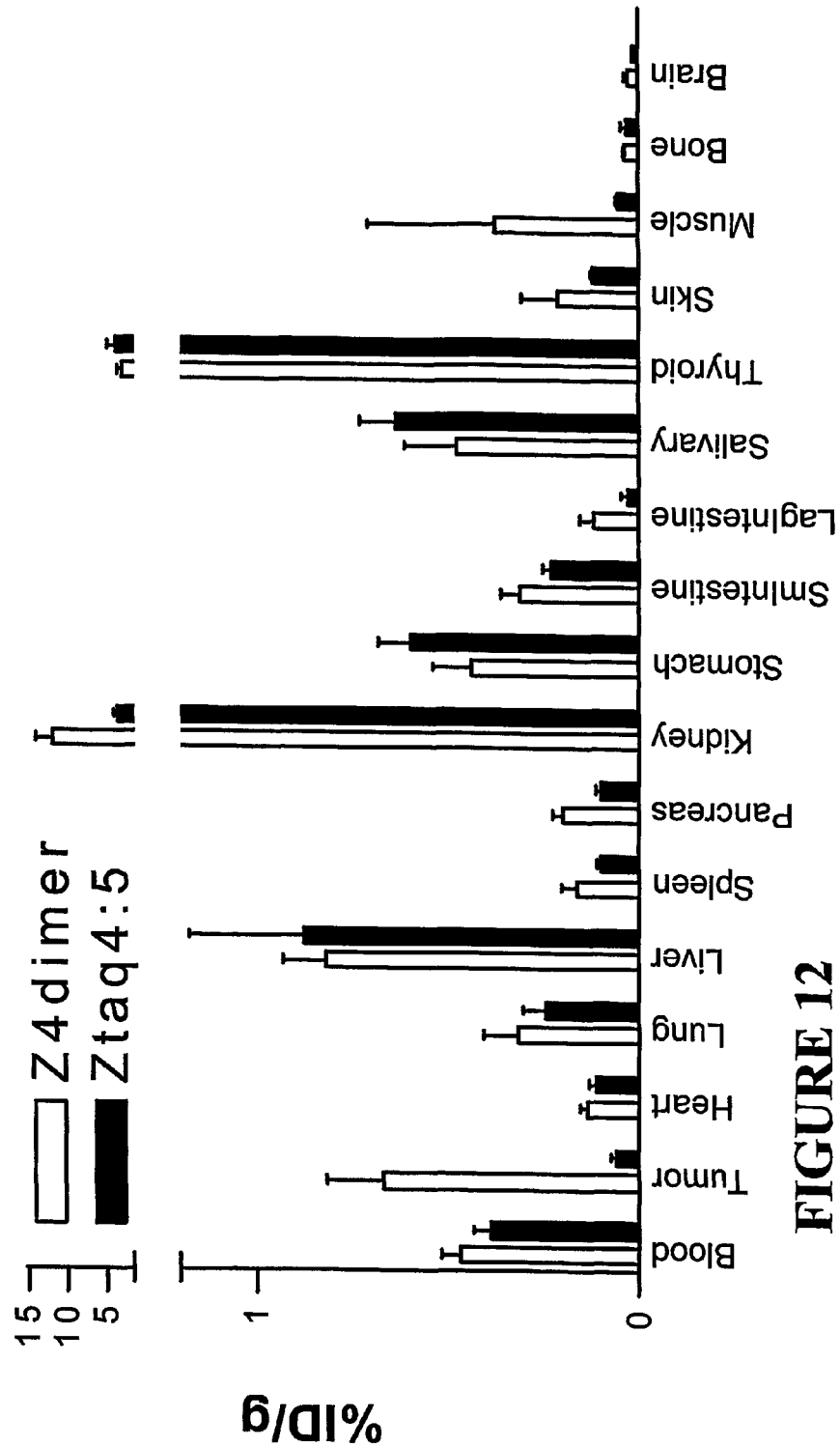
FIG. 12 shows a comparison of biodistribution of radioactivity in tumor bearing nude mice 4 h after injection of $^{125}$I-benzoate-$(Z_{HER2\ A})_2$ (Z4dimer) or $^{125}$I-benzoate-$Z_{Taq}$ (Ztaq4: 5).

In Biodistribution Experiment II, the mice of group III were injected with an amount of $Z_{Taq}$ corresponding to the amount of $(Z_{HER2\ A})_2$ injected in the mice of the other groups. $Z_{Taq}$ had been labeled with radioiodine using the same indirect method as for $(Z_{HER2\ A})_2$. $Z_{Taq}$ is non-specific with respect to HER2 receptors. Uptake of radioactivity at 4 h post injection in group I and group III were compared. The results of this experiment (FIG. 12) showed that the non-specific $Z_{Taq}$ molecule had a lower tumor uptake than the specific $(Z_{HER2\ A})_2$ molecule. Tumor to blood ratios in this experiment were 1.43 (group I, specific $(Z_{HER2\ A})_2$) and 0.15 (group III, unspecific $Z_{Taq}$). Statistical analysis showed that the difference was significant (p=0.009). In all other organs, radioactivity uptake was on the same level for both Z molecules.

A higher tumor to blood ratio for $(Z_{HER2\ A})_2$ was observed in this experiment, compared to the blocking experiment. This was likely due to the later time point of the experiment (4 h pi).

Biodistribution

The results from the groups of mice in Biodistribution Experiments I and II that had been injected iv with labeled $(Z_{HER2\ A})_2$ were combined in an analysis of the biodistribution of radioiodine in organs and tissues of the tumor bearing mice. The results are shown in FIGS. 13-16.

Figure 13:
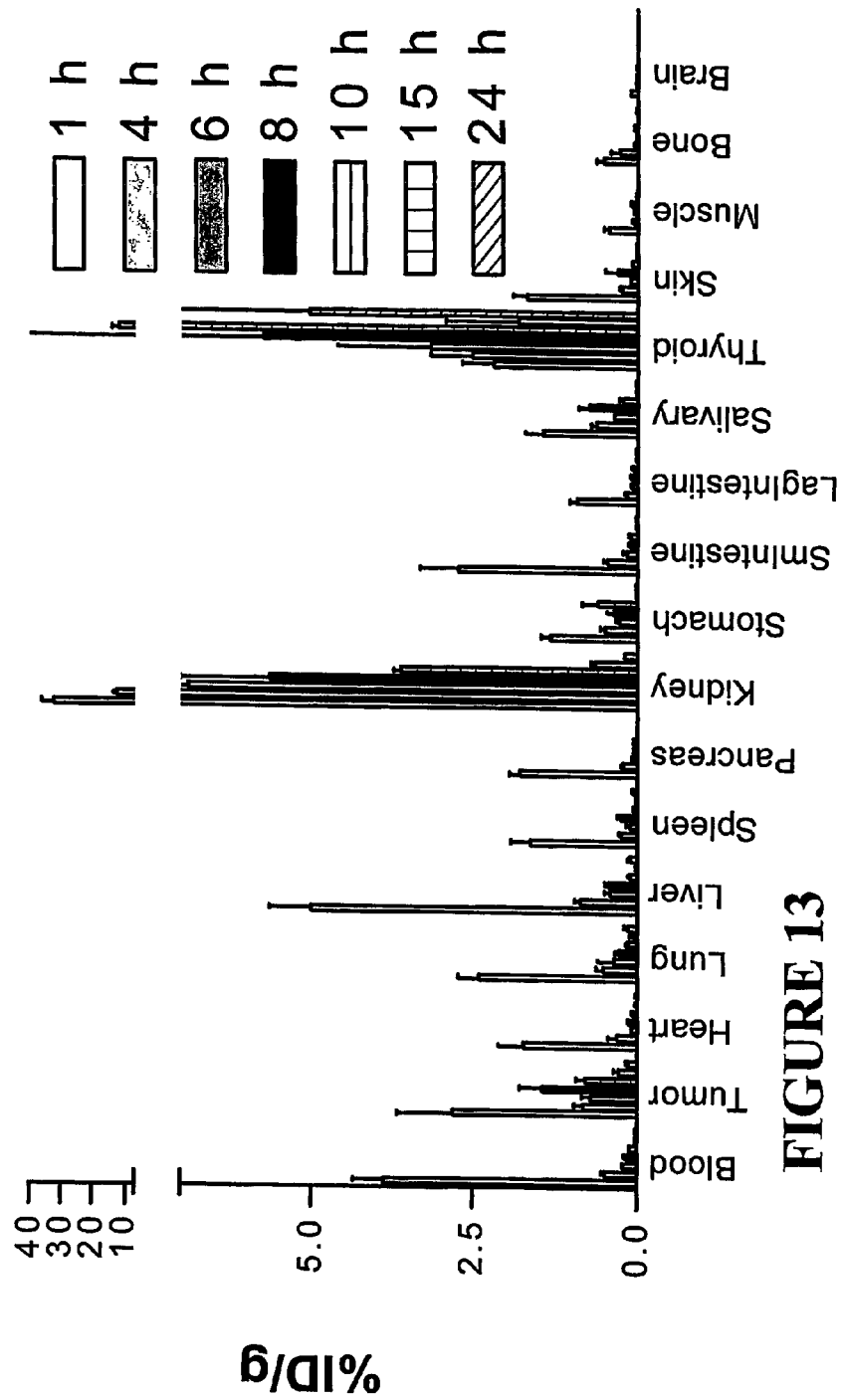
FIG. 13 shows the biodistributon of radioiodine in tumor bearing nude mice at various time points after injection of $^{125}$I-benzoate-$(Z_{HER2\ A})_2$. Data are combined from two biodistribution experiments. Data for 4 h pi are averages from both experiments.
Figure 14:
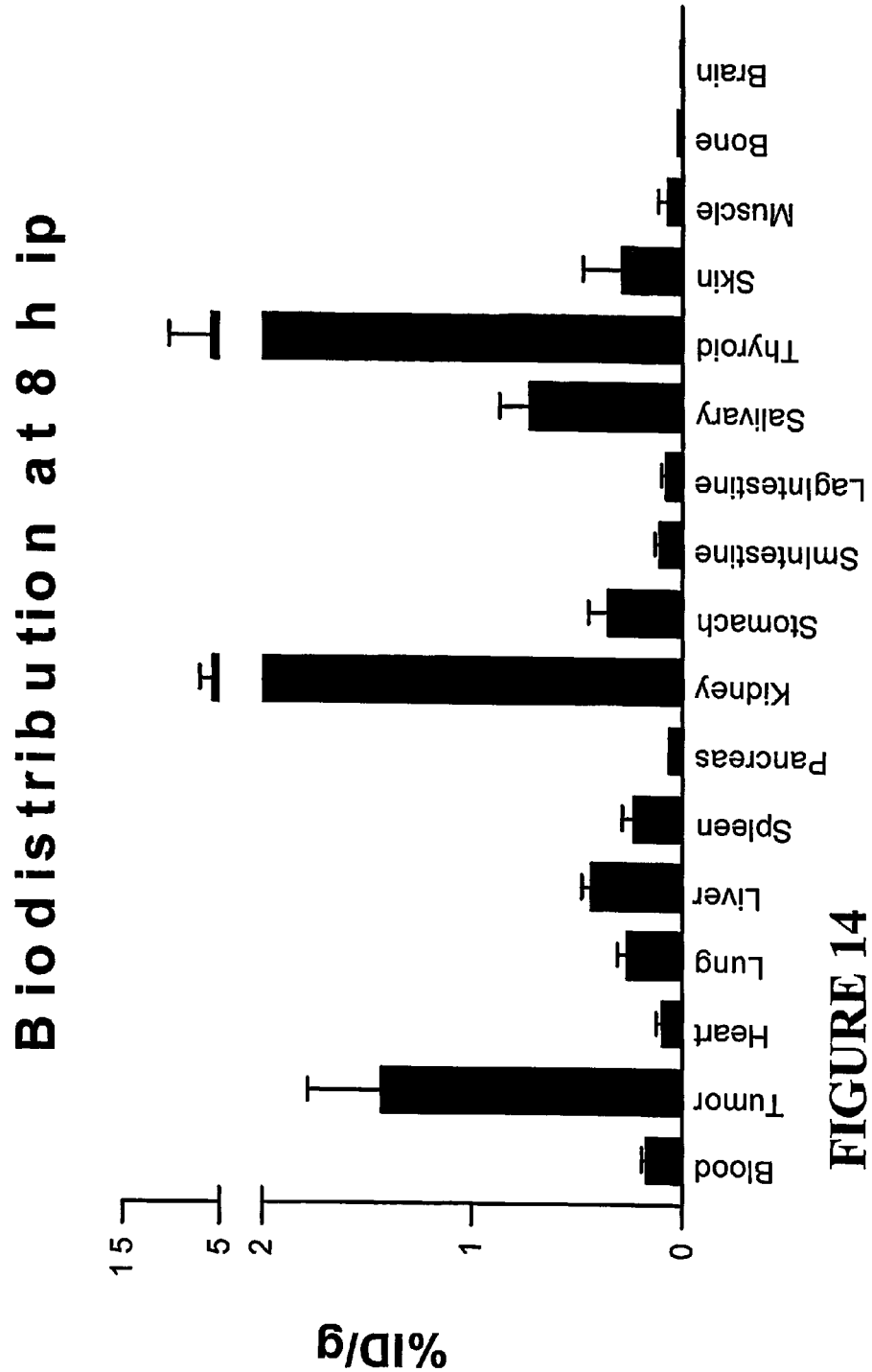
FIG. 14 shows the biodistributon of radioiodine in tumor bearing nude mice 8 h after injection of $^{125}$I-benzoate-$(Z_{HER2\ A})_2$.
Figure 15:
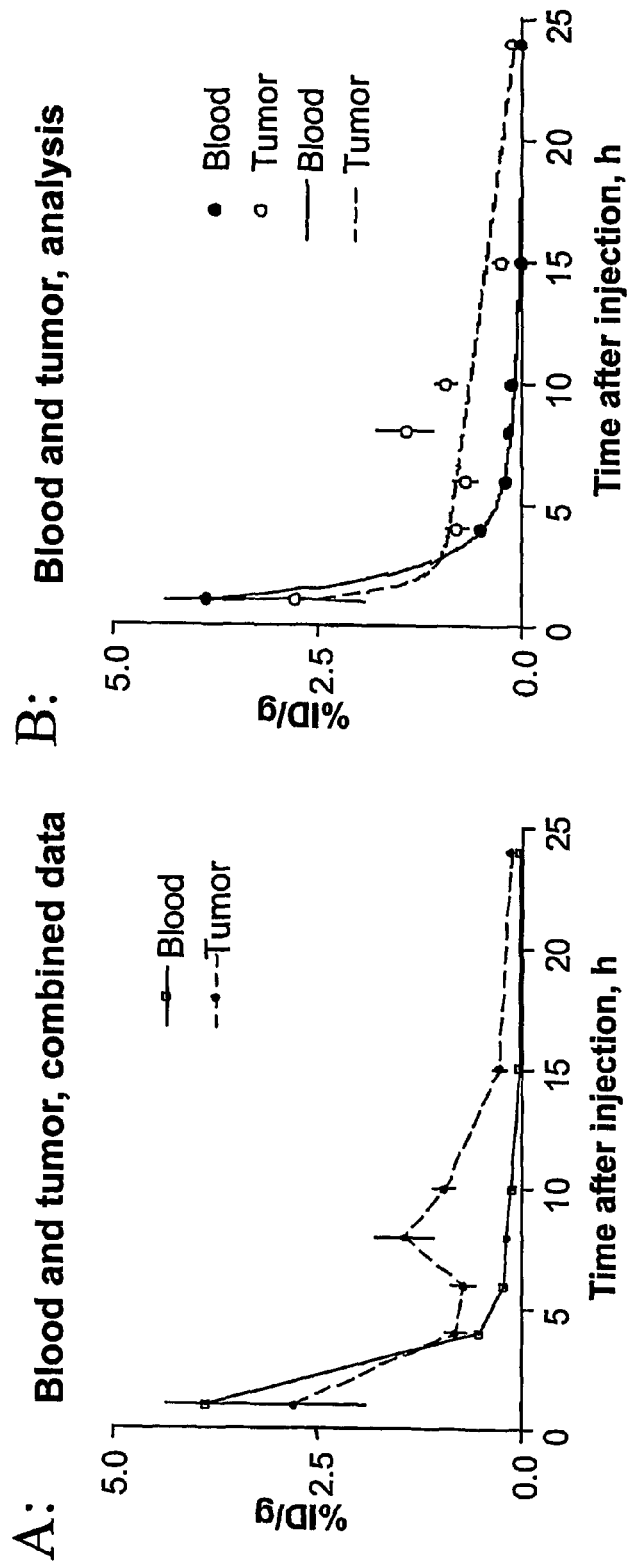
FIG. 15 shows a comparison of radioactivity concentration in blood and tumors. Data are combined from two biodistribution experiments. A: experimental data. B: curves fitted using non-linear regression with a two-phase exponential decay model.
Figure 16:
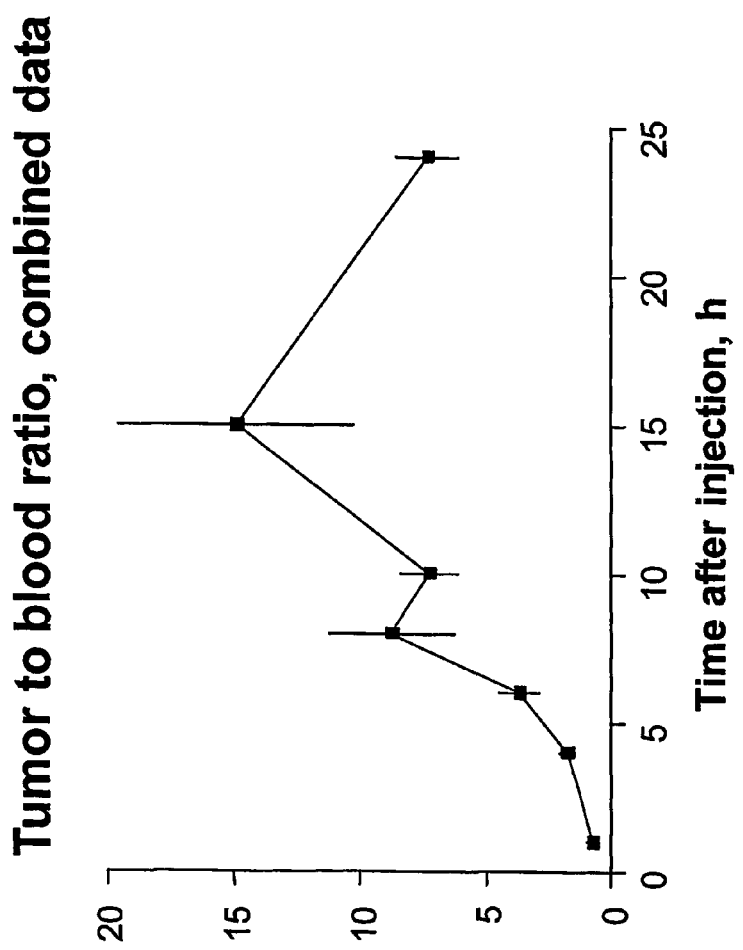
FIG. 16 shows the tumor to blood ratio of radioactivity concentration. Data are combined from two biodistribution experiments.

Referring to FIGS. 13 and 14, the concentration of $^{125}$I in tumors was higher than in most normal organs, indicating that the $(Z_{HER2\ A})_2$ polypeptide is able to target tumor cells bearing HER2. The radioactivity concentration in normal organs and tissues was found to be lower than in the tumors, with the exception of kidney (all time points), thyroid (all time points), and liver (early time points). The experiments showed a quick clearance of radioiodine from blood and normal organs. Clearance from normal organs mainly followed blood clearance, with the exception of the thyroid, where accumulation of radioiodine was found. Elevated thyroid uptake of free iodine, even for indirect labeling methods, is well known and can to some extent be prevented with "cold", or nonradioactive, iodine (Larsen R H et al, Nucl Med Biol 25:351-357 (1998)). High concentrations of radioiodine were also found in the kidneys of the mice, which was also expected since the kidneys are the main excretion pathway for such small proteins and catabolites.

FIGS. 15A and B show the progression over time of the radioiodine concentration in blood and in tumor. Starting at 4 h pi, tumor radioactivity was higher than blood radioactivity. Using the experimental data as presented in FIG. 15A, the half-lives of radioiodine in blood and tumors were calculated using GraphPad Prism©, v 3.0, from GraphPad Software (San Diego, USA). Non-linear regression with a two-phase exponential decay was used as model, and the resulting graphs are presented in FIG. 15B. $T_{1/2}\alpha$ for the tumors was shorter (0.36 h) than for blood (0.76 h), but $T_{1/2}\beta$ was longer (87.5 h for tumors vs 4.3 h for blood), which is in good agreement with the obtained results. For comparison, $T_{1/2}\alpha$ in blood for the labeled dimer, calculated with the same model using biodistribution data from normal, non-tumor bearing mice, was 0.3 h (data not shown).

The tumor to blood ratio of radioactivity concentration (FIG. 16) increased with time during at least 12 h pi. This ratio is a good estimating factor for imaging contrast, because the main background in radioactivity imaging comes from radioactivity in the blood. Taking into account the tumor to blood ratio and the tumors' radioactivity concentrations, it was concluded that 6 and 8 h pi might be the optimal time points for images. For an image with good contrast, the tumor to non-tumor radioactivity concentration ratio should not be less than 2.

Gamma Images

Gamma images were taken of each of the two groups of 5 mice each selected for imaging (at 6 h and 8 h pi, respectively). In all mice at both time points, kidneys with well-defined structures could be identified. Some additional structure (probably liver) is visible on the image of mice 6 h pi over the kidneys, as well as an elevated background from a generalized blood pool. Some animals had some urine in their bladders, which is also directly visible. On the image with mice 8 h pi, additional structure in the neck area can be identified, which in all likelihood is the thyroid.

Figure 17:
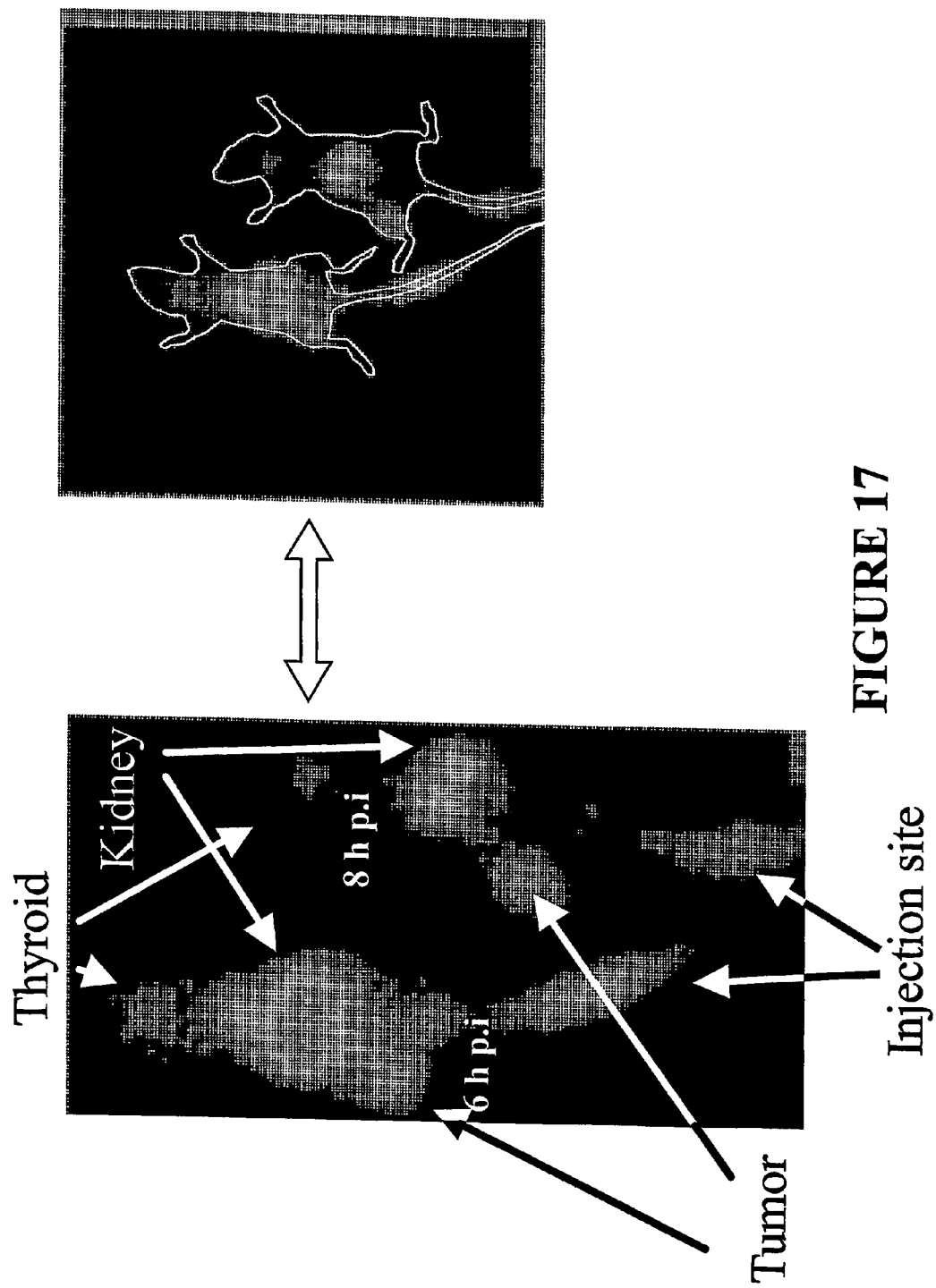
FIG. 17 is a whole body γ-camera image of tumor bearing mice (SKOV-3) 6 h (left mouse) and 8 h (right mouse) after iv tail injection of $^{125}$I-benzoate-$(Z_{HER2\ A})_2$ conjugate.

From 5 animals in each image session, one large invasive tumor (from the first batch of SKOV-3 injection) was visualized. No other tumor localization was evident. The two animals in question were chosen for an additional imaging session, and the result is shown in FIG. 17.

Summary

Biodistribution of the dimer polypeptide $(Z_{HER2\ A})_2$, indirectly labeled with radioiodine ($^{125}$I) via a benzoate group, in mice bearing SKOV-3 (ovarian cancer cell line) tumors showed good agreement with normal biodistribution of the conjugate in normal mice. Tumor uptake of radioiodine injected as $^{125}$I-benzoate-$(Z_{HER2\ A})_2$ was achieved. The tumor uptake was receptor mediated and specific, as shown by blocking experiments using a pre-injection of a high concentration of non-labeled $(Z_{HER2\ A})_2$ molecule, and by injection of a non-specific, labeled Z variant, $Z_{Taq}$. Analysis of the data obtained showed that the radioactivity concentration in tumor was higher than the radioactivity concentration in blood after 4 h pi, and higher than in the majority of normal organs and tissues after 6 h pi, except for the kidneys and thyroid. Gamma images of mice bearing SKOV-3 xenograft tumors were obtained at 6 and 8 h pi. Good resolution was achieved. At both time points, big invasive tumors could be clearly identified.

EXAMPLE 5

Biodistribution and Tumor Targeting with His$_6$-$Z_{HER2\ A}$ Monomer in Nude Mice Bearing SKOV-3 Xenografts In the experiments making up this example, the monomeric $Z_{HER2\ A}$ polypeptide according to Example 1 and 2 was radiolabeled with $^{125}$I and injected into mice bearing a grafted tumor characterized by HER2 overexpression. Studies of the biodistribution of the polypeptide were conducted to study its localization.

Materials and Methods

Indirect Radioiodination of $Z_{HER2\ A}$

For labeling with $^{125}$I, 40 μl of monomeric His$_6$-$Z_{HER2\ A}$ was subjected to the same treatment as the dimeric polypeptide construct in Example 4.

Animal Preparation

Female outbred nu/nu balb mice from M&B (10-12 weeks old when arrived) were used under permission C66/4. Mice were acclimatized in the animal facilities of the Rudbeck laboratory, Uppsala, Sweden, using standard diet, bedding and environment during the week before xenografts were established in them. The mice had free access to food and drinking water. Three weeks before the experiment, $5 \times 10^7$ SKOV-3 human ovarian cancer cells (ATCC #HTB-77) were injected subcutaneously in the right hind leg of 16 mice. By the time of the experiments, tumors had been established in all mice and all mice weighed 22-27 g.

Measurement of Radioactivity $^{125}$I measurement was performed and % ID/g calculated as described in Example 4.

Biodistribution Experiment 16 mice were randomly divided into 4 groups (I-IV) with 4 mice in each group. Groups, injections and times of sacrifice were according to Scheme 3. The mice were injected iv in the tail with 0.5 μg $Z_{HER2}$A, indirectly labeled with $^{125}$I (100 kBq per mouse) in 50 μl PBS. All injections were tolerated well, judging by the lack of any visible problems.

Scheme 3

| Group | Mouse ID | Time of sacrifice post injection (h) |
|---|---|---|
| I | 1-4 | 1 |
| II | 5-8 | 4 |
| III | 9-12 | 8 |
| IV | 13-16 | 24 |

The mice were sacrificed and samples taken as described in the first biodistribution study of Example 4. The samples of organs and tissue were weighed, and their radioactivity measured with a γ-counter (Automated γ-counter with a 3-inch NaI(Tl) detector, 1480 Wallac WIZARD, Wallac O Y, Turku, Finland).

Results

Figure 18:
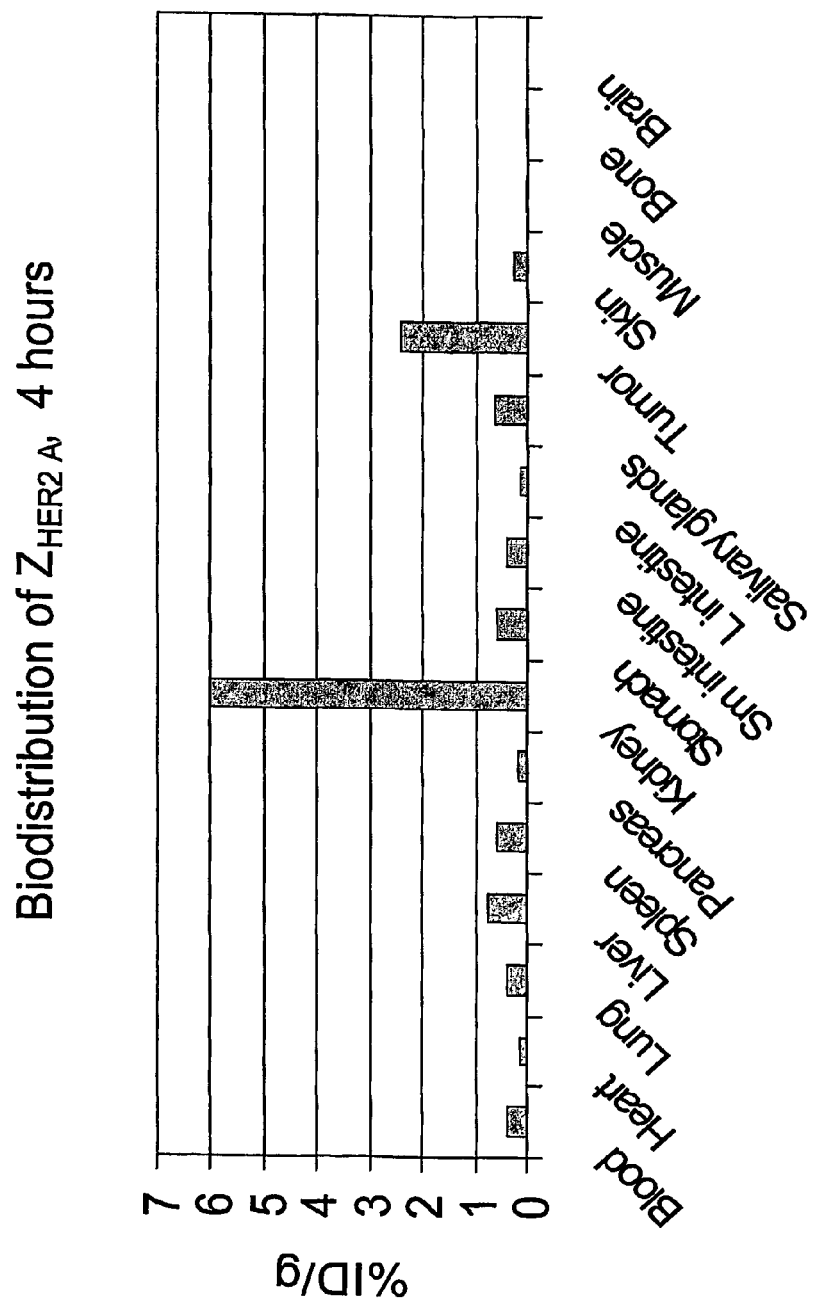
FIG. 18 shows the biodistribution of radioactivity in tumor bearing nude mice 4 hours after injection of $^{125}$I-benzoate-$Z_{HER2\ A}$.
Figure 19:
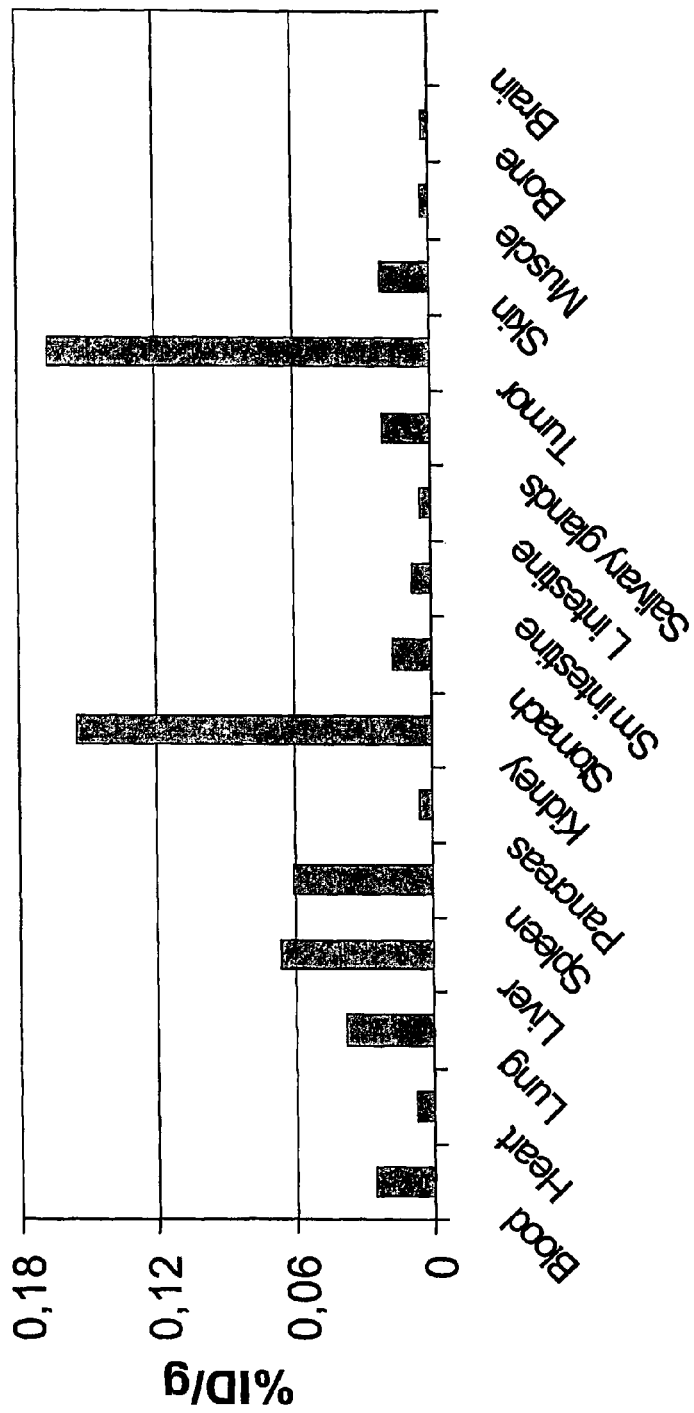
FIG. 19 shows the biodistribution of radioactivity in tumor bearing nude mice 24 hours after injection of $^{125}$I-benzoate-$Z_{HER2\ A}$.
Figure 20:
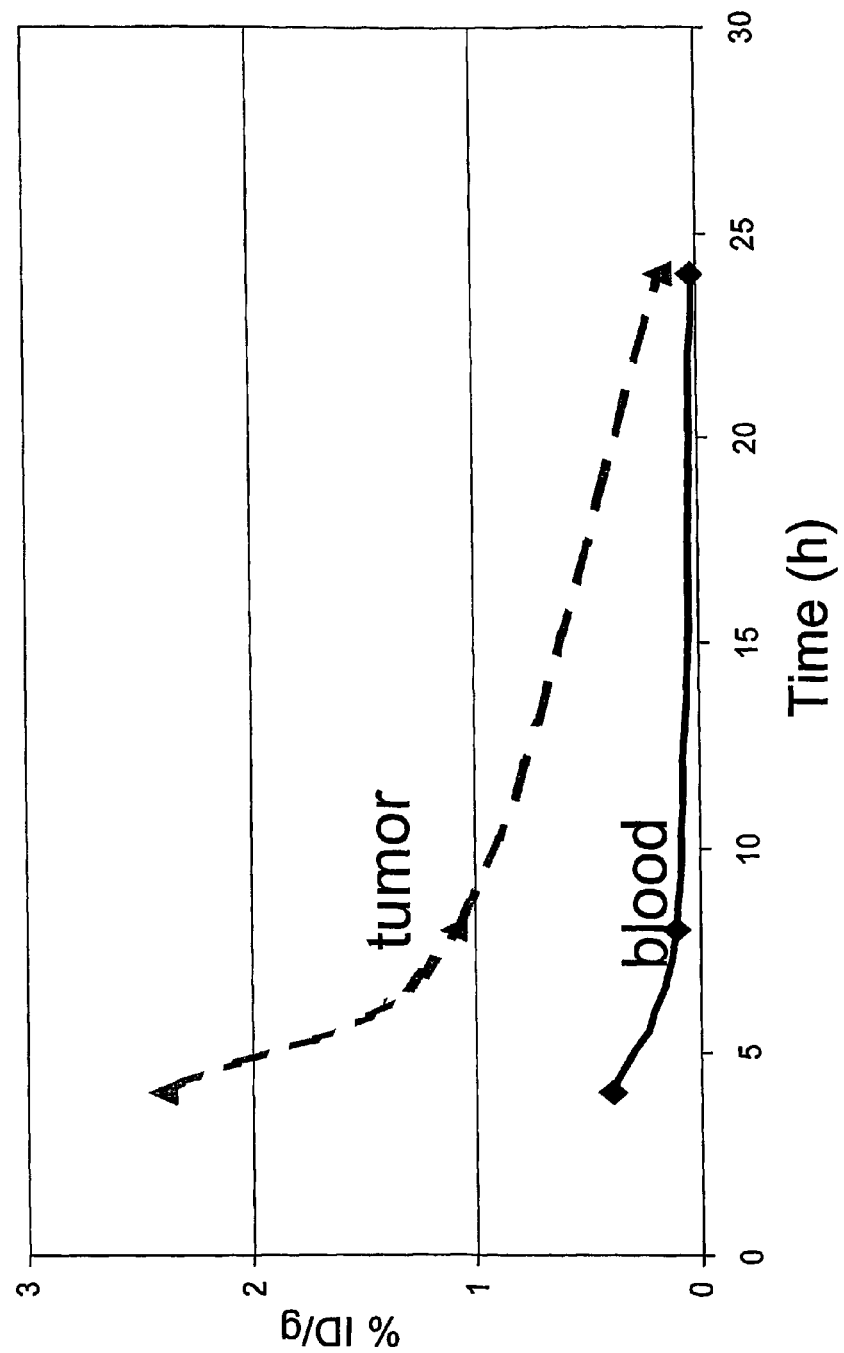
FIG. 20 shows the kinetics of radioiodine in tumor and blood of tumor bearing nude mice at various time points after injection of $^{125}$I-benzoate-$Z_{HER2\ A}$.
Figure 21:
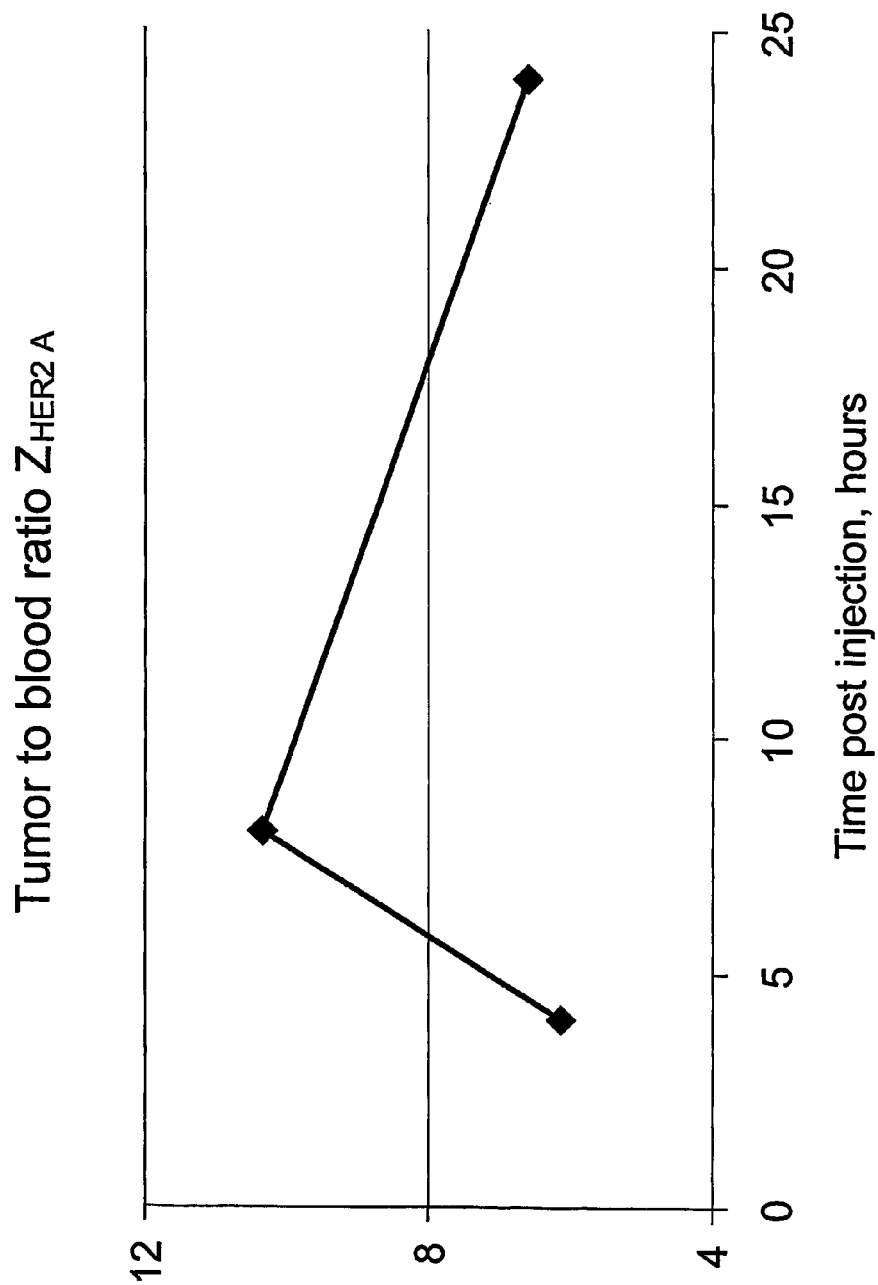
FIG. 21 shows the tumor to blood ratio of radioactivity following injection of $^{125}$I-benzoate-$Z_{HER2\ A}$.

The results from the groups of mice that had been injected sc with labeled $Z_{HER2\ A}$ were analyzed to establish the distribution of radioiodine in organs and tissues of the mice. The results are shown in FIGS. 18-20. Referring to FIGS. 18 and 19, the concentration of 125, in tumors was higher than in most normal organs at 4 and 24 hours, indicating that the $Z_{HER2\ A}$ polypeptide is able to target tumor cells bearing HER2. The radioactivity concentration in normal organs and tissues was found to be lower than in the tumors, with the exception of kidney (all time points) and thyroid (all time points). The experiments showed a quick clearance of radioiodine from blood and normal organs. Clearance from normal organs mainly followed blood clearance, with the exception of the thyroid, where accumulation of radioiodine was found. High concentrations of radioiodine were also found in the kidneys of the mice. FIG. 20 shows the progression over time of the radioiodine concentration in blood and in tumor. Starting at 4 h pi, tumor radioactivity was six times higher than blood radioactivity. The tumor to blood ratio of radioactivity concentration (FIG. 21) increased with time during at least 8 h pi, when it was 10 to 1.

Summary

Biodistribution of the monomer polypeptide $Z_{HER2\ A}$, indirectly labeled with radioiodine ($^{125}$I) via a benzoate group, in mice bearing SKOV-3 (ovarian cancer cell line) tumors showed good agreement with normal biodistribution of the conjugate in normal mice. Tumor uptake of radioiodine injected as $^{125}$I-benzoate-$Z_{HER2\ A}$ was achieved. Analysis of the data obtained showed that the radioactivity concentration in tumor was higher than the radioactivity concentration in blood after 4 h pi, and in contrast to the dimeric form ($Z_{HER2\ A})_2$, also higher than in the majority of normal organs and tissues already after 4 h pi, except for the kidneys and thyroid.

EXAMPLE 6

Figure 22:
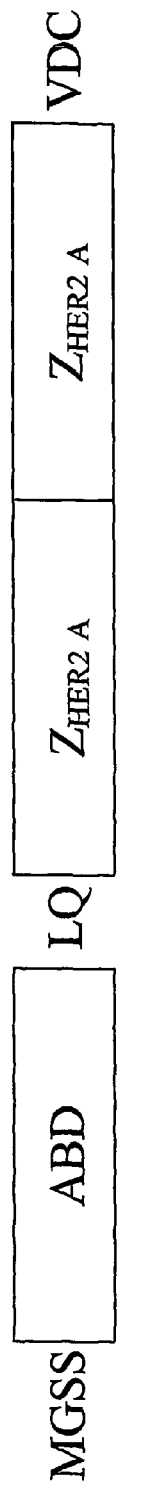
FIG. 22 is a schematic illustration of the amino acid sequence of a fusion polypeptide produced in Example 6. $Z_{HER2\ A}$ represents HER2 binding domain with the sequence shown in SEQ ID NO:2 and ABD represents an albumin binding domain from streptococcal protein G.

Biodistribution and Tumor Targeting with ABD($Z_{HER2\ A})_2$ in Nude Mice Bearing SKOV-3 Xenografts In the experiments making up this example, a dimeric ($Z_{HER2\ A})_2$ polypeptide according to Example 3 was genetically fused at its N-terminal end to "Albumin Binding Domain" (ABD) from streptococcal protein G, in order to form a polypeptide denoted ABD ($Z_{HER2\ A})_2$ (FIG. 22). ABD binds human and mouse serum albumin with high affinity (M Johansson et al, J Biol Chem 277:8114-8120 (2002)). Albumin is an abundant protein in the blood with a slow plasma clearance. Binding to albumin with high affinity should confer upon the binder slow kinetics in similar to the albumin protein itself. Extending the circulation time of a tumor targeting ligand in an animal should, in theory, enhance the dose delivered to the tumor. To test this, the ABD($Z_{HER2\ A})_2$ polypeptide was radiolabeled with $^{125}$I and injected into mice bearing a grafted tumor characterized by HER2 overexpression. Studies of the biodistribution of the polypeptide were conducted to study its localization.

Materials and Methods

DNA Construction and Protein Production

The selection of a novel affibody ligand, denoted His$_6$-$Z_{HER2\ A}$ and having affinity for the HER2 receptor, is described above in Examples 1 and 2. A dimeric $Z_{HER2\ A}$ variant, constructed by subcloning the gene fragment encoding the $Z_{HER2\ A}$ polypeptide into the expression vector for His$_6$-$Z_{HER2\ A}$, was described in Example 3. An ABD fusion protein of this dimeric $Z_{HER2\ A}$ variant was constructed by subcloning the gene fragment encoding the ABD polypeptide into the expression vector for His$_6$-$Z_{HER2\ A}$, substituting the hexahistidine tag with the ABD polypeptide. In addition, a C-terminal cysteine residue was added to the fusion protein using extension PCR. The introduced ABD fragment was verified by DNA sequencing on a DNA sequencer ABI Prisms 3700 Analyzer (Applied Biosystems, Foster City, Calif.). The *Escherichia coli* strain RR1ΔM15 (Rüther, Nucleic Acids Res 10:5765-5772 (1982)) was used as bacterial host during the cloning procedure. The resulting vector encodes, under the control of the T7 promoter (Studier et al, Meth Enzymol 185:60-89 (1990)), an ABD fused dimeric $Z_{HER2}$ variant, ABD($Z_{HER2\ A})_2$, fused to a C-terminal cysteine residue, which allows site specific chemical modifications (FIG. 22). The dimeric $Z_{HER2}$ variant was expressed as a fusion with ABD in *E. coli* strain BL21(DE3), and recovered by affinity chromatography purification on an albumin Sepharose affinity column prepared according to the manufacturer's protocol (Amersham Biosciences). Protein concentration was calculated from absorbance measurements at 280 nm, using the appropriate extinction coefficient. The purified protein was further analyzed by SDS-PAGE on a Tris-Glycine 16% homogenous gel, using a Novex system (Novex, CA, USA). Protein bands were visualized with Coomassie Brilliant Blue staining. Upon SDS-PAGE analysis, the protein was observed as a specific band of the expected molecular weight.

Indirect Radioiodination of ABD($Z_{HER2\ A})_2$

For labeling with $^{125}$I, 40 μl of ABD($Z_{HER2\ A})_2$ was subjected to the same treatment as the dimeric polypeptide construct in Example 4.

Animal Preparation

Female outbred nu/nu balb mice from M&B (10-12 weeks old when arrived) were used under permission C66/4. Mice were acclimatized in the animal facilities of the Rudbeck laboratory, Uppsala, Sweden, using standard diet, bedding and environment during the week before xenografts were established in them. The mice had free access to food and drinking water. Three weeks before the experiment, $5 \times 10^7$ SKOV-3 human ovarian cancer cells (ATCC #HTB-77) were injected subcutaneously into the right hind leg of 16 mice. By the time of the experiments, tumors had been established in all mice and all mice weighed 22-27 g.

Measurement of Radioactivity $^{125}$I measurement was performed and % ID/g calculated as described in Example 4.

Biodistribution Experiment 16 mice were randomly divided into 4 groups (I-V) with 4 mice in each group. Groups, injections and times of sacrifice were according to Scheme 4. The mice were injected iv in the tail with 0.5 µg ABD($Z_{HER2\ A}$)$_2$, indirectly labeled with $^{125}$I (100 kBq per mouse) in 50 µl PBS. All injections were tolerated well, judging by the lack of any visible problems.

Scheme 4

| Group | Mouse ID | Time of sacrifice post injection (h) |
|---|---|---|
| I | 1-4 | 12 |
| II | 5-8 | 24 |
| III | 9-12 | 48 |
| IV | 13-16 | 72 |

The mice were sacrificed and samples taken as described in the first biodistribution study of Example 4. The samples of organs and tissue were weighed, and their radioactivity measured with a γ-counter (Automated γ-counter with a 3-inch NaI(Tl) detector, 1480 Wallac WIZARD, Wallac O Y, Turku, Finland).

Results

Figure 23:
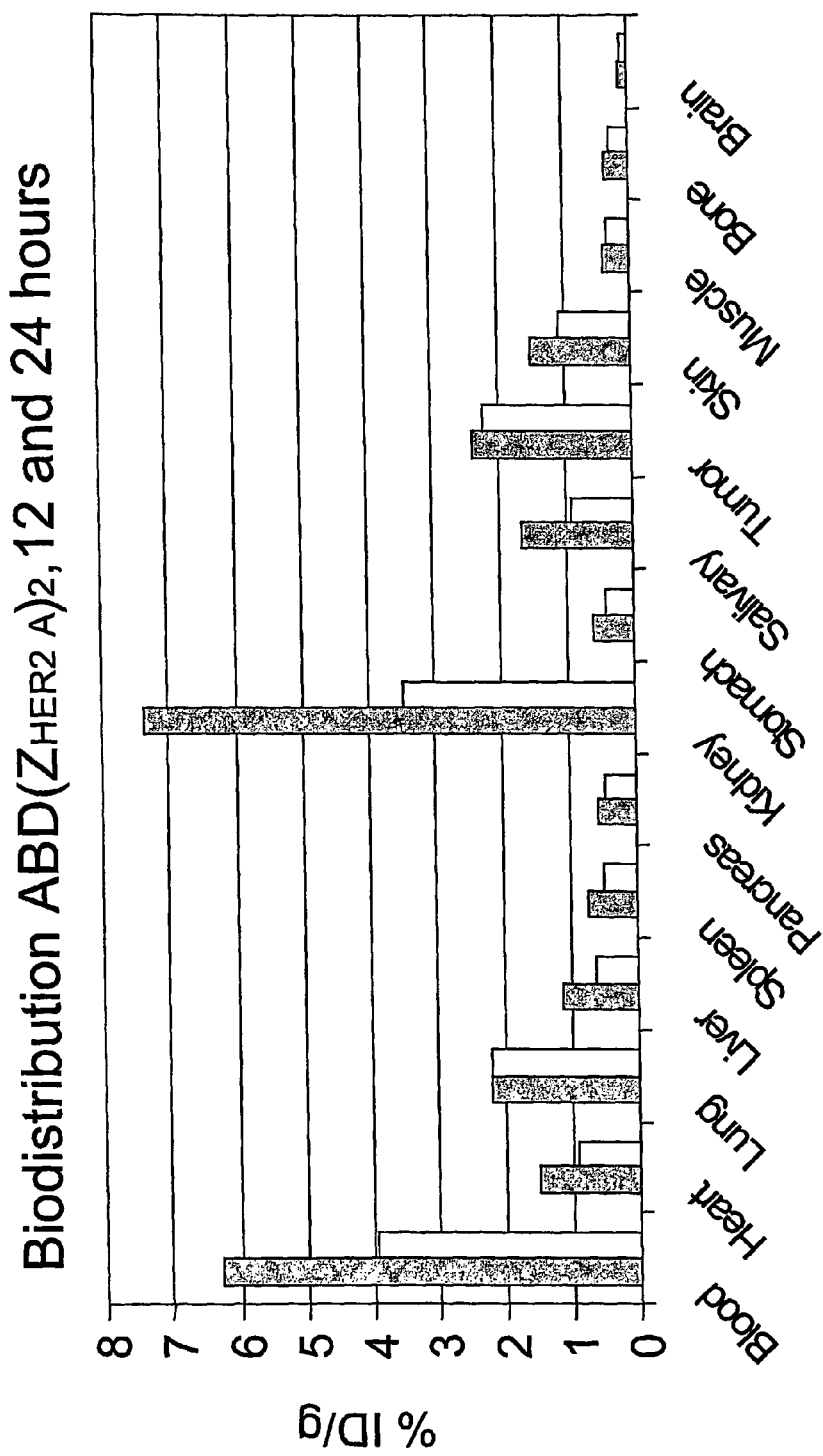
FIG. 23 shows the biodistribution of radioactivity in tumor bearing nude mice 12 (grey) and 24 hours (white) after injection of $^{125}$I-benzoate-ABD $(Z_{HER2\ A})_2$.
Figure 24:
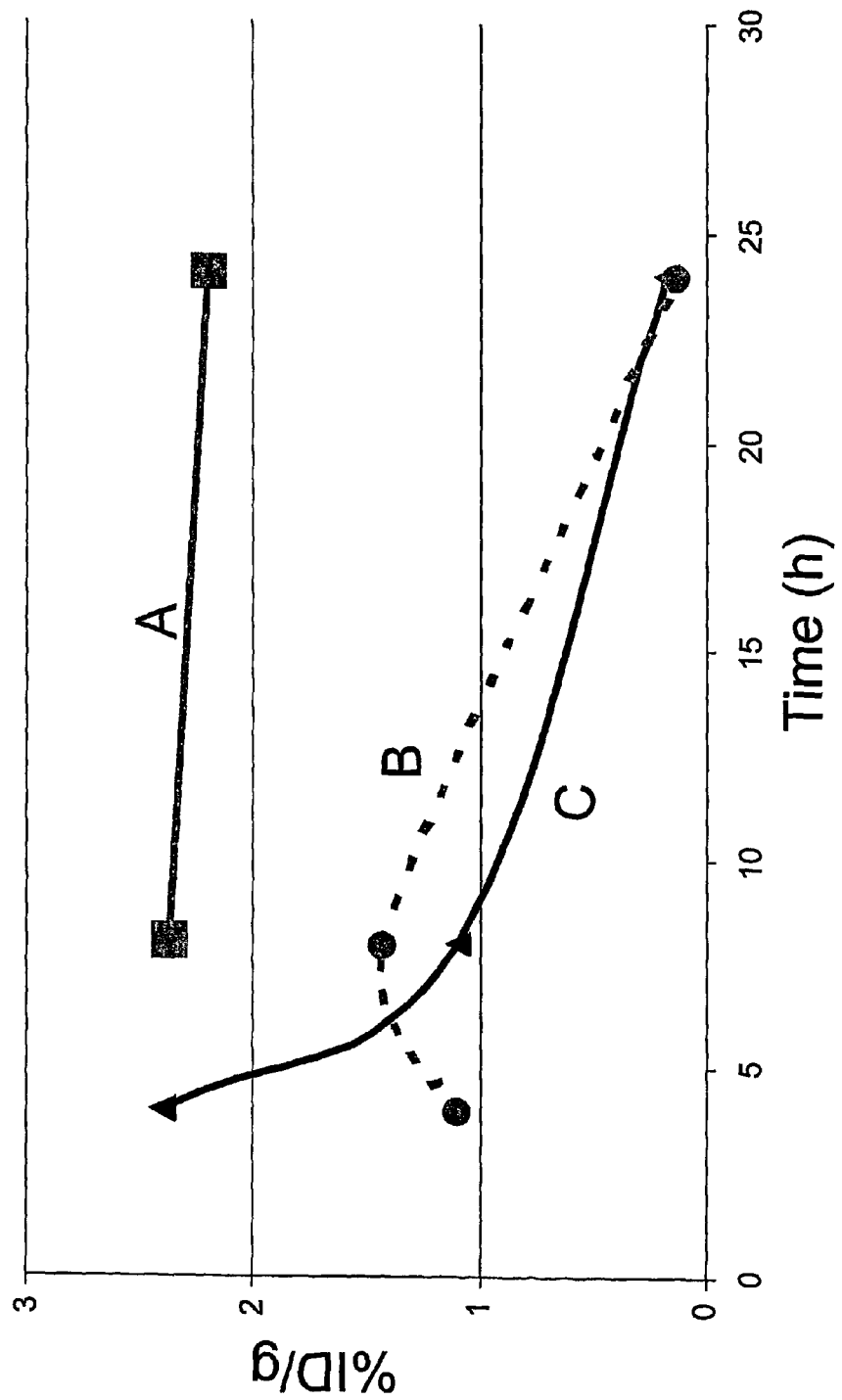
FIG. 24 shows the kinetics of radioiodine in tumors of tumor bearing nude mice at various time points after injection of (A): $^{125}$I-ABD $(Z_{HER2\ A})_2$, (B): $^{125}$I-$(Z_{HER2\ A})_2$, and (C): $^{125}$I-$Z_{HER2\ A}$.

The results are shown in FIGS. 23-24. Referring to FIG. 23, the concentration of $^{125}$I in tumors was higher than in most normal organs at 12 (tumor 2.4% ID/g) and 24 hours (tumor 2.2% ID/g), indicating that the ABD($Z_{HER2\ A}$)$_2$ polypeptide is able to target tumor cells bearing HER2. The radioactivity concentration in normal organs and tissues was found to be lower than in the tumors, with the exception of kidney (all time points, at 24 hours 3.5% ID/g), thyroid (all time points, at 24 hours 5.2% ID/g) and blood (all time points, at 24 hours 3.9% ID/g). Lung values are more or less equivalent to the tumor values, which may be due to the high blood content in the lungs. The experiments showed very slow clearance of radioiodine from blood. This is to be expected, since the ABD moiety of ABD($Z_{HER2\ A}$)$_2$ binds with high affinity to serum albumin, an abundant protein in the blood with slow kinetics. Clearance from normal organs was faster than blood clearance, with the exception of the thyroid, where accumulation of radioiodine was found. High concentrations of radioiodine were also found in the kidneys of the mice. FIG. 24 shows the progression over time of the radioiodine concentration associated with ABD ($Z_{HER2\ A}$)$_2$ in tumor, in comparison with the results generated for monomeric and dimeric constructs of $Z_{HER2}$A in Examples 4 and 5. At 24 h pi, tumor radioactivity using ABD ($Z_{HER2\ A}$)$_2$ was thirteen times higher than for monomer or dimer, indicating that extending residence time of the targeting moiety in the body indeed may be used to increase the dose on the tumor. The data also support that the ($Z_{HER2\ A}$)$_2$ moiety can be functionally coupled to the albumin binding domain.

Summary

Biodistribution of the fusion polypeptide ABD($Z_{HER2\ A}$)$_2$, indirectly labeled with radioiodine ($^{125}$I) via a benzoate group, in mice bearing SKOV-3 (ovarian cancer cell line) tumors showed good agreement with the expected properties of an albumin binding polypeptide. Tumor uptake of radioiodine injected as $^{125}$I-ABD($Z_{HER2\ A}$)$_2$ was achieved, and the dose on the tumor was higher than for the dimeric or monomeric versions of the $Z_{HER2\ A}$ polypeptide. Analysis of the data obtained showed that the radioactivity concentration in tumor was higher than the radioactivity concentration in most other organs after 12 h pi, although the radioactivity in lungs, kidneys, thyroid and blood remained high.

EXAMPLE 7

Biodistribution of Technetium-Labeled Dimer $^{99m}$Tc-($Z_{HER2\ A}$)$_2$

In the experiments making up this example, the dimeric His$_6$-($Z_{HER2\ A}$)$_2$ polypeptide according to Example 3 was labeled with the diagnostic imaging nuclide 99m-technetieum and injected into normal mice and into mice bearing a grafted tumor characterized by HER2 overexpression. $^{99m}$Technetieum ($^{99m}$Tc) is a radionuclide with close to ideal properties for in vivo diagnosis. In addition, it is cheap and readily available, making it a good candidate for medical imaging in the clinic. Studies of biodistribution of the polypeptide were conducted to study its localization.

Materials and Methods

Technetium Labeling of His$_6$-($Z_{HER2\ A}$)$_2$

The His$_6$-($Z_{HER2\ A}$)$_2$ polypeptide was labeled according to manufacturer's instructions using the commercially available IsoLink™ kit (Mallinckrodt, Netherlands), which directs the $^{99m}$Tc nuclide to the hexahistidine tag on the His$_6$-($Z_{HER2\ A}$)$_2$ protein. The IsoLink™ kit reagents generate a technetium cation, [$^{99m}$Tc (CO)$_3$ (H$_2$O)$_3$]$^+$, which can then be stably coordinated by the hexahistidine tag, providing means for labelling the His$_6$ tag of the His$_6$-($Z_{HER2\ A}$)$_2$ polypeptide specifically.

Briefly, 0.5-0.6 ml $^{99m}$Tc stock solution eluted from the generator at Uppsala University Hospital was incubated with the content of the IsoLink™ Carbonyl labelling agent (DRN4335, Mallinckrodt) for 20 min at 100° C. in a water bath. 40 µl of the thus obtained technetium cation, [$^{99m}$Tc (CO)$_3$ (H$_2$O)$_3$]$^+$, was mixed with 40 µl His$_6$-($Z_{HER2\ A}$)$_2$ in PBS (1.2 mg/ml) and incubated for 1 h at 50° C. The product was purified by separation on a NAP-5 size exclusion column with a cut-off of 5 kD (Pharmacia, Uppsala). The product purity was 97%, according to instant thin layer chromatography.

Animal Preparation

Female outbred nu/nu balb mice from M&B (10-12 weeks old when arrived) were used under permission C66/4. Mice were acclimatized in the animal facilities of the Rudbeck laboratory, Uppsala, Sweden, using standard diet, bedding and environment during the week before xenografts were established in them. The mice had free access to food and drinking water. Three weeks before the experiment, $5 \times 10^7$ SKOV-3 human ovarian cancer cells (ATCC #HTB-77) were injected subcutaneously into the right hind leg of 4 mice. By the time of the experiments, tumors had been established in all mice and all mice weighed 22-27 g.

Measurement of Radioactivity $^{99m}$Tc measurement was performed and % ID/g calculated as described for $^{125}$I in Example 4.

Biodistribution Experiment

One group of mice with 4 animals was used for the experiment. Injections and times of sacrifice were according to Scheme 5. The mice were injected iv in the tail with 0.5 µg His$_6$-(Z$_{HER2\ A}$)$_2$, labeled with $^{99m}$Tc (100 kBq per mouse) in 50 µl PBS. All injections were tolerated well, judging by the lack of any visible problems.

Scheme 5

| Group | Mouse ID | Time of sacrifice post injection (h) |
| --- | --- | --- |
| I | 1-4 | 8 |

The mice were sacrificed and samples taken as described in the first biodistribution study of Example 4. The samples of organs and tissue were weighed, and their radioactivity measured with a γ-counter (Automated γ-counter with a 3-inch NaI(Tl) detector, 1480 Wallac WIZARD, Wallac O Y, Turku, Finland).

Results

Figure 25:
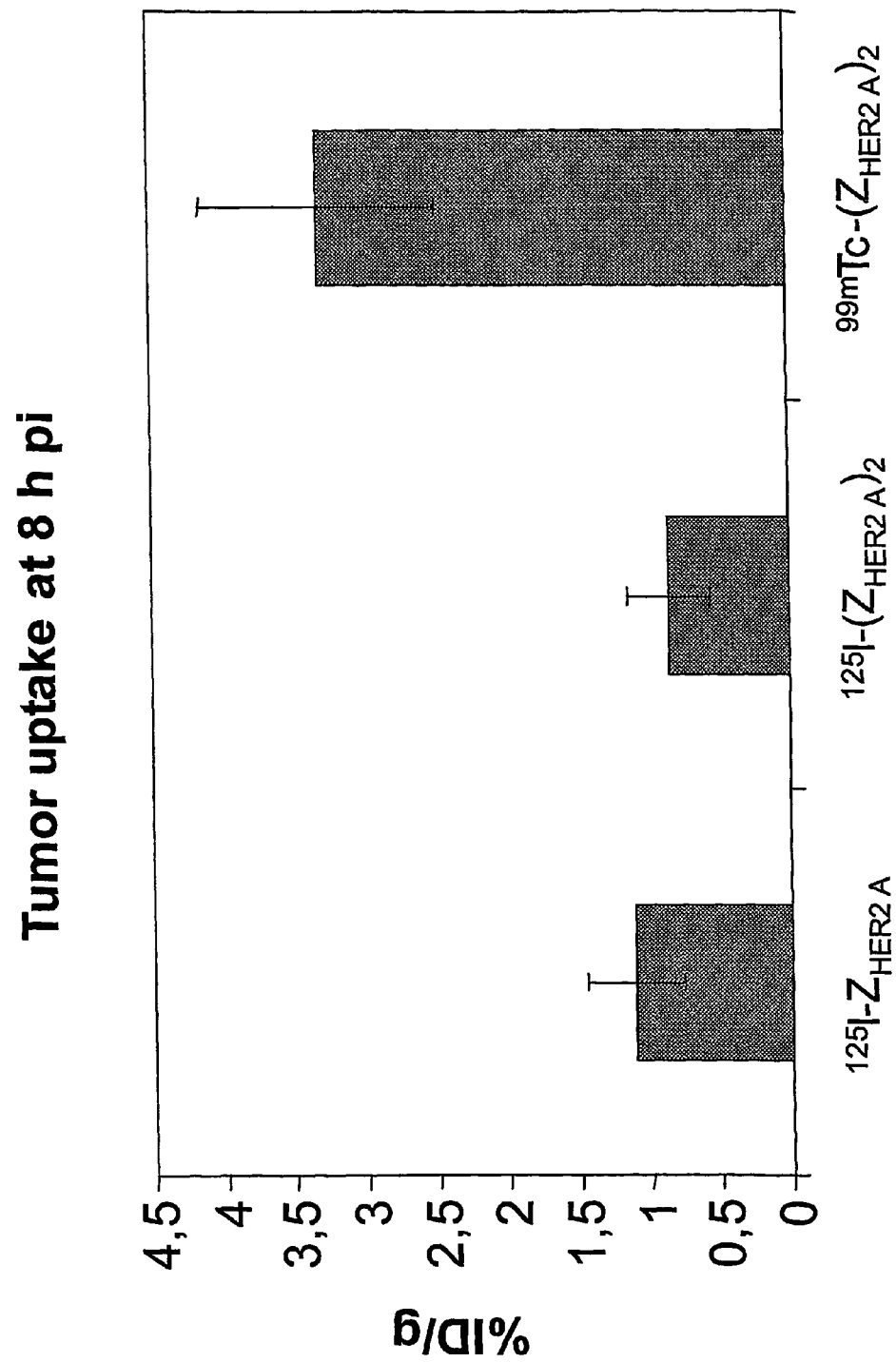
FIG. 25 shows a comparison of the delivered dose of the $^{125}$I-benzoate-$Z_{HER2\ A}$, $^{125}$I-benzoate-$(Z_{HER2\ A})_2$, and $^{99m}$Tc-$(Z_{HER2\ A})_2$.
Figure 26:
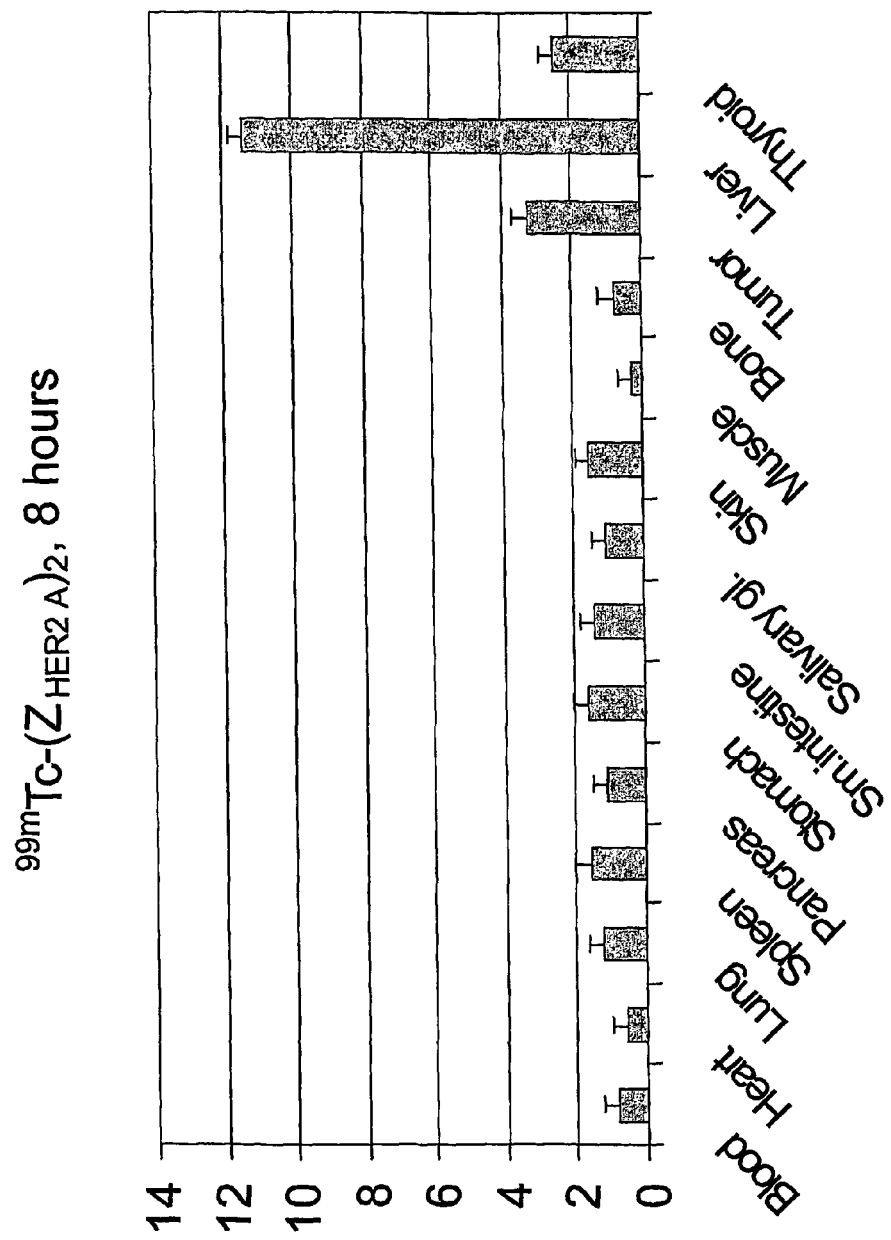
FIG. 26 shows the biodistribution of radioactivity in tumor bearing nude mice 8 hours after injection of $^{99m}$Tc-$(Z_{HER2\ A})_2$.
Figure 27:
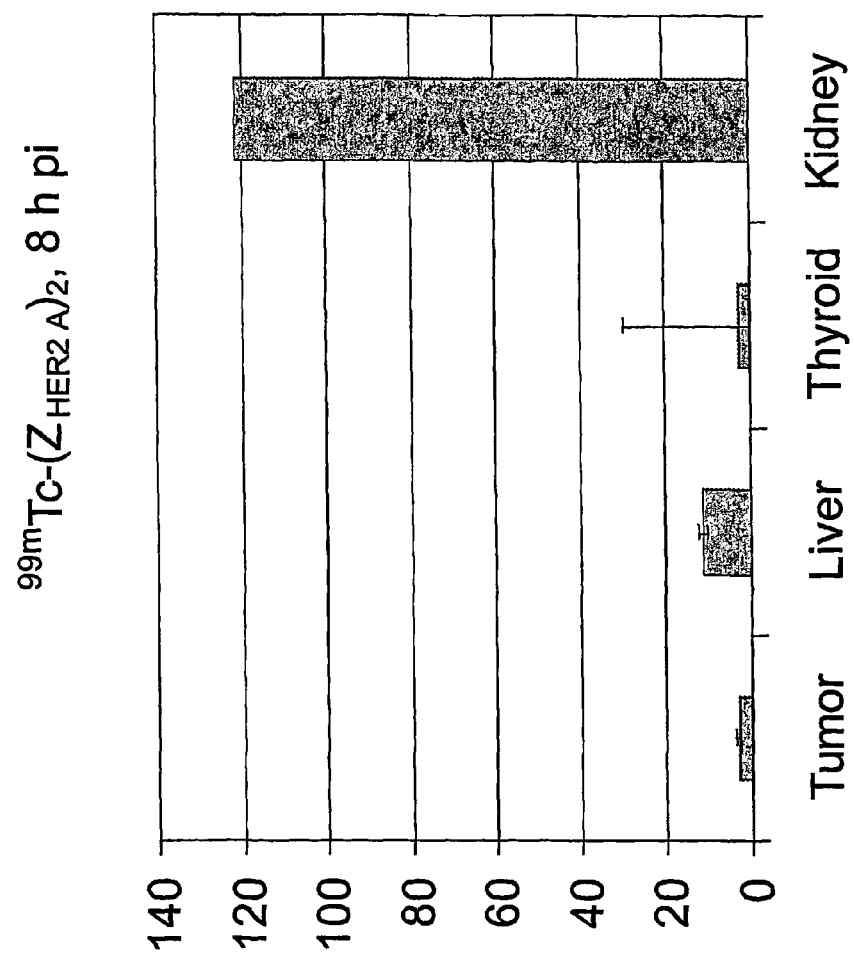
FIG. 27 shows a comparison of radioactivity in selected organs in tumor bearing nude mice 8 hours after injection of $^{99m}$Tc-$(Z_{HER2\ A})_2$.

The conjugate $^{99m}$Tc-His$_6$-(Z$_{HER2\ A}$)$_2$ had a high stability in vitro (challenge with PBS, plasma, cysteine and excess of free histidine). The results from the in vivo biodistribution $^{99m}$Tc-His$_6$-(Z$_{HER2\ A}$)$_2$ experiments are shown in FIGS. 25-27. Referring to FIG. 25, the total tumor dose was three times higher using $^{99m}$Tc-His$_6$-(Z$_{HER2\ A}$)$_2$ (3.3% ID/g at 8 h pi) as compared to the concentration of the $^{125}$I-labeled monomeric construct, $^{125}$I-benzoate-Z$_{HER2\ A}$ (1.1% ID/g at 8 h pi), or dimeric construct, $^{125}$I-benzoate(Z$_{HER2\ A}$)$_2$ (1.06% ID/g at 8 h pi). It is known that $^{99m}$Tc is a better residualizing agent than $^{125}$I, implying that the delivered dose remains, whereas iodine doses are metabolized and released from the tumor cells. Referring to FIG. 26, the concentration of $^{99m}$Tc in tumors was higher than in most normal organs at 8 h pi (tumor 3.3% ID/g), indicating that the $^{99m}$Tc-His$_6$-(Z$_{HER2\ A}$)$_2$ polypeptide is able to target tumor cells bearing HER2. The radioactivity concentration in normal organs and tissues was found to be lower than in the tumors, with the exception of kidney (at 8 hours 27% ID/g, 36× the tumor dose) and liver (at 8 hours 11.4% ID/g, 3× the tumor dose) (FIG. 27). High kidney values were expected, since $^{99m}$Tc-His$_6$-(Z$_{HER2\ A}$)$_2$ is cleared via the kidneys. The high level of tracer in the kidneys does not present a toxicity problem, since the total dose injected will be very low for diagnostic purposes. The amount of radioactivity in thyroid was not at all as high as when $^{125}$I was used (Example 4), as expected (at 8 hours 1% ID/g). Clearance from normal organs mainly followed blood clearance, with the exception of the kidneys, where accumulation of $^{99m}$technetium was observed with a peak at one hour. The levels thereafter decreased, with a rapid elimination phase during one hour (up to 2 hours pi) followed by a slow elimination phase, with a substantial dose (70% ID/g) still in the kidney after 24 hours.

Tumor to blood ratio for the technetium conjugate at 8 hours pi was 4, with a total tumor dose of 3.3% ID/g. This indicated that $^{99m}$technetium could be used for in vivo diagnostic applications. For comparison, at the same time point, the tumor doses of $^{125}$I-benzoate-(Z$_{HER2\ A}$)$_2$ and $^{125}$I-benzoate-Z$_{HER2\ A}$ were about 1%, but the tumor to blood ratios were about 11.

Summary

Biodistribution of the $^{99m}$Tc labeled polypeptide $^{99m}$Tc-His$_6$-(Z$_{HER2\ A}$)$_2$ in mice bearing SKOV-3 (ovarian cancer cell line) tumors showed relatively good distribution properties for medical imaging purposes. Tumor uptake of technetium injected as $^{99m}$Tc-His$_6$-(Z$_{HER2\ A}$)$_2$ was achieved and the dose on the tumor was higher than for $^{125}$I-labeled dimeric or monomeric versions of the Z$_{HER2\ A}$ polypeptide. Analysis of the data obtained showed that the radioactivity concentration in tumor was higher than the radioactivity concentration in most other organs and blood after 8 h pi, although the liver and the kidney had substantially higher uptake than the tumor.

EXAMPLE 8

In Vitro Labelling and Characterization using $^{211}$At

In the experiments making up this example, the dimeric His$_6$-(Z$_{HER2\ A}$)$_2$ polypeptide according to Example 3 was labeled with the therapeutic radio nuclide $^{211}$astatine ($^{211}$At), using the same chemistry as described earlier for labeling with $^{125}$I. One goal for radionuclide tumor targeting is radiation therapy. This requires nuclides that emit high energy particles, such as a particles and high energy a particles, which can eradicate the targeted cell. The a emitting radiohalogen $^{211}$At (T$_{1/2}$=7.2 h) has a range of just a few cell diameters, which means that cell eradication may take place with high precision. Studies of the cell killing ability in vitro of the $^{211}$At-labeled polypeptide were conducted.

Materials and Methods

Two days in advance, 100,000 SKBR-3 cells, characterized by HER2 overexpression, were seeded in 3 cm dishes. 60 µg His$_6$-(Z$_{HER2\ A}$)$_2$ polypeptide was labeled with $^{211}$At produced in the Scanditronix MC32 cyclotron of the Copenhagen University Hospital and purified in the laboratory of Jörgen Carlsson, Uppsala University, Uppsala, Sweden. An approximate 1:1 and 5:1 molar ratio of $^{211}$At(Z$_{HER2\ A}$)$_2$ molecules per cell receptor were added to three dishes each. Three additional dishes were supplied with the 5:1 concentration of $^{211}$At-(Z$_{HER2\ A}$)$_2$ but also a 500 times access of unlabeled His$_6$-(Z$_{HER2\ A}$)$_2$ to block the binding sites and thereby estimate effects of unspecific irradiation. Cells were incubated with $^{211}$At-(Z$_{HER2\ A}$)$_{2\ for}$ 24hours in 37° C. After 24 hours of incubation, all cells were washed and supplied with new, fresh medium. They were then monitored for growth once a week for about two months.

In parallel, a set of dishes prepared in the same way as those used in the cell killing assay described above was supplied with the same solutions of $^{211}$At-(Z$_{HER2\ A}$)$_2$. These cells were harvested at different time points, and cell numbers counted and radioactivity content measured, in order to establish uptake curves for all groups of dishes. These curves were used to calculate the amount of decays per cell over the 24 hour period used in the cell killing experiment.

Results

Figure 28:
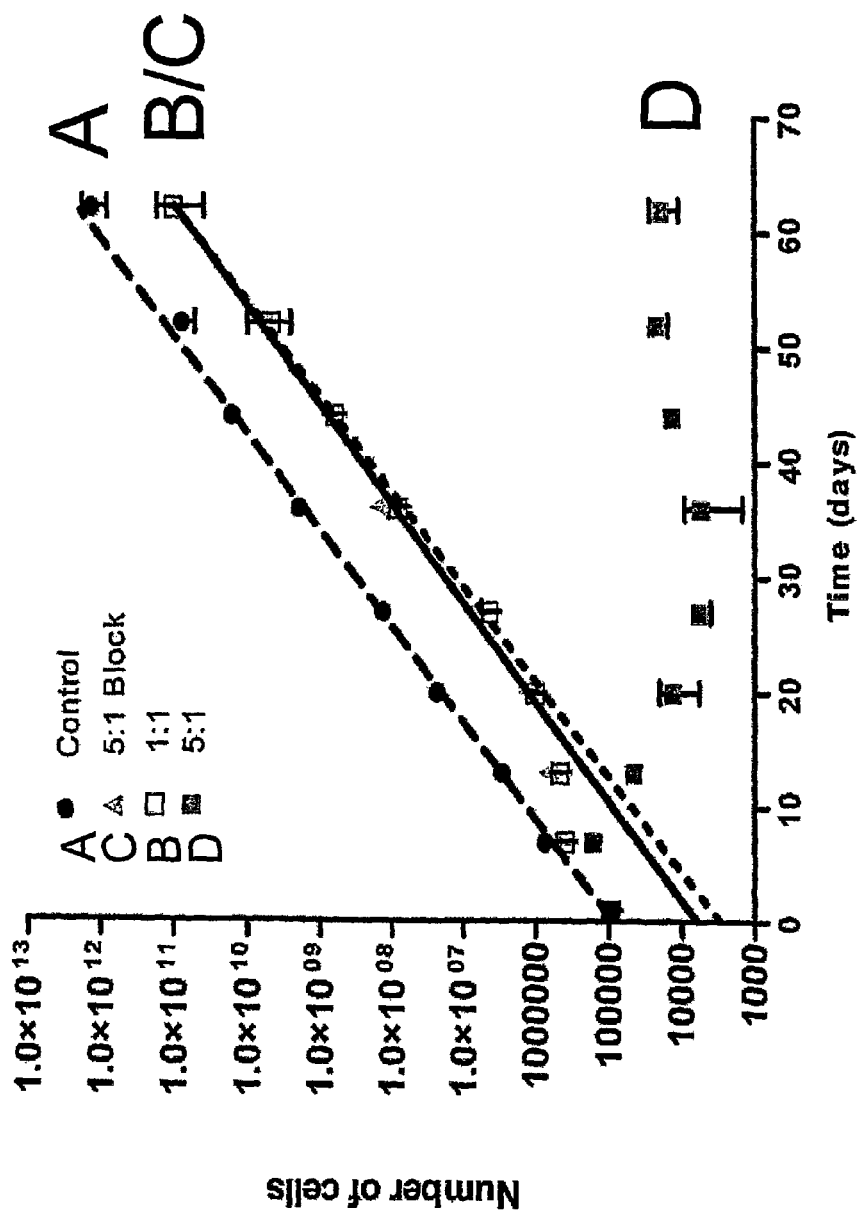
FIG. 28 is a diagram showing growth of SKBR-3 cells after exposure of $^{211}$At-$(Z_{HER2\ A})_2$ for 24 hours. The filled, black circles of curve A represent cells without exposure; the open squares of curve B represent cells exposed to a moderate level; and the filled grey squares of curve D represent cells exposed to high level of $^{211}$At-$(Z_{HER2\ A})_2$. The filled grey triangles of curve C represent cells exposed to the high level of $^{211}$At-$(Z_{HER2})_2$ combined with a 500 fold excess of unlabeled $His_6$-$(Z_{HER2\ A})_2$. Values are averages of three experiments, error bars represent standard deviation.

Cells from the human breast cancer cell line SKBR-3, which overexpresses HER-2, were exposed to two different doses of $^{211}$At-(Z$_{HER2\ A}$)$_2$ for 24 hours. In the first dose, the added $^{211}$At-(Z$_{HER2\ A}$)$_2$ molecules equaled the number of HER2 target receptors on the cells. In the second dose, $^{211}$At-labeled molecules were added in a five-fold excess. After 24 hours of incubation, the cells were monitored and counted once a week for two months, and the surviving fraction determined. As seen in FIG. 28, the response was related to the dose given. The cells receiving the equimolar amount of $^{211}$At-(Z$_{HER2\ A}$)$_2$ did not show any specific growth delay as compared with the control where radioactivity was added without a targeting agent. There was a short growth delay due to unspecific radiation damage, but the cells did not stop growing. In contrast, when $^{211}$At-$(Z_{HER2\ A})_2$ was added in fivefold excess, the inhibition of cell growth was impressive. At the end of the experiment, the group receiving the high dose had not yet recovered, whereas the low dose and the control groups had increased by 106. Assuming that surviving cells retain about the same growth rate after irradiation as before, all cells in the 5:1 group were eradicated. The uptake curve revealed that the 5:1 blocked group also had received substantial cell associated irradiation, probably due to insufficient blockage. The number of decays per cell (DPC) was estimated from integrated uptake curves. From the growth curve, doubling times were calculated as the slope of the exponential growth curve, and surviving fraction was calculated by extrapolation of delayed growth back to the time of exposure. Results are shown in Table 1.

TABLE 1

|  | Doubling time (days) | DPC | Survival |
| --- | --- | --- | --- |
| Control | 2.5 | — | 100% |
| Block | 2.6 | 12 | 7.0% |
| 1:1 | 2.5 | 37 | 3.4% |
| 5:1 | — | 98 | — |

Summary $^{211}$At-$(Z_{HER2})_2$ showed specific binding to HER2 overexpressing SKBR-3 cells in vitro. Induced cell death correlated well with the accumulated dose. Less than 100 decays per cell were shown to be enough to cause killing of single cells and to achieve complete cell eradication.

EXAMPLE 9

Identification and Characterization of Additional HER2-Binding Polypeptides

In order to increase the affinity of the HER2 binding Z variants obtained from the selection described in Example 1, an affinity maturation strategy was applied involving the construction of a second library (Gunneriusson et al, Protein Eng 12:873-878 (1999); Nord et al, Eur J Biochem 268:4269-77 (2001)), followed by reselection against HER2. An alignment of the first generation of polypeptide variants $Z_{HER2\ A}$, B, C and D showed that, apart from the identities at position, 13, 14, 28, 32 and 35, between $Z_{HER2\ A}$ and $Z_{HER2\ B}$, there is a convergence of R and K in position 10 and of Q and T in position 11. Thus, the second generation library contained five fixed positions 13, 14, 28, 32 and 35 and two partly fixed positions, position 10 (cgc/aaa as degenerated codons) and position 11 (caa/acc as degenerated codons), while the remaining positions 9, 17, 18, 24, 25 and 27 were again randomized using NNG/T degenerated codons. After transformation, a library of $3 \times 10^8$ clones was obtained. Antigen binding molecules were subjected to five rounds of selection, using decreasing concentrations of biotinylated extracellular domain of human HER2 (HER2-ECD) as the target (recombinant human HER2 extracellular domain, amino acids 238-2109, provided by Fox Chase Cancer Center, Philadelphia, USA)

80 and 260 colonies clones obtained from the fourth and fifth round, respectively, were picked in order to perform an analysis of their HER2 binding activity.

ABAS ELISA for Analysis of HER2 Binding

Figure 29:
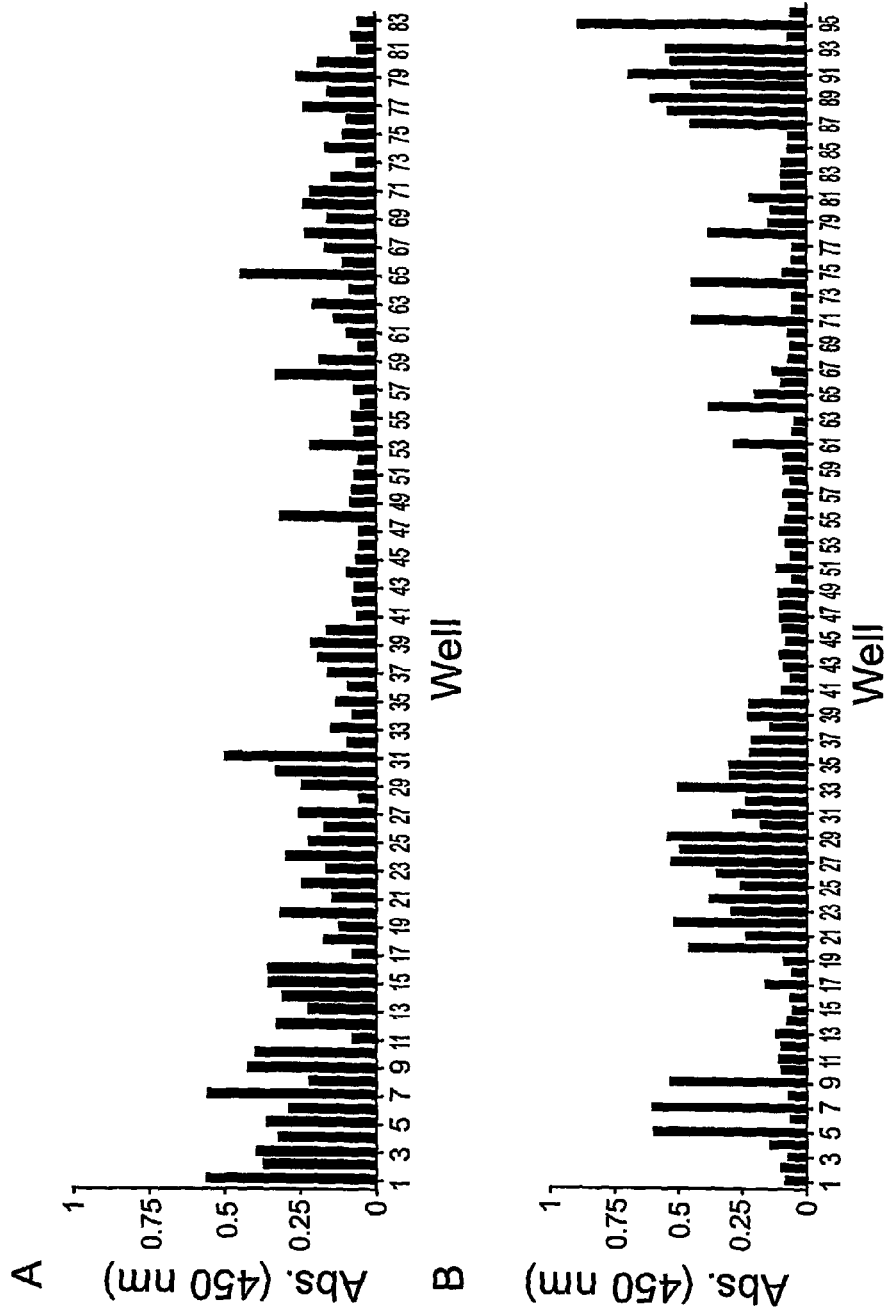
FIGS. 29A and B show results from ABAS ELISA to determine the binding activity of clones picked from the fourth and fifth round of the affinity maturation selection.

Clones randomly chosen from the fourth and fifth round of the selection were produced in 96 well plates (Nunc). An ELISA screening procedure, termed ABAS ELISA, was used to identify high affinity HER2 binding Z variants. Single colonies were inoculated in 1 ml TSB-YE medium (30.0 g Tryptic Soy Broth (Merck) and 5.0 g Yeast extract (Merck), water to a final volume of 1 l) supplemented with 1 mM IPTG and 100 µg/ml ampicillin in deep well 96 well plates and grown on a shaker over night at 37° C. Cells were pelleted by centrifugation at 3000 g for 10 minutes. The pellets were resuspended in 300 µl PBS-T and frozen at least for 30 minutes at −80° C. The plates were thawed in tepid water and centrifuged at 3500 g for 20 minutes. 100 µl of the supernatants were loaded on microtiter wells (#9018 Costar®) which had been incubated with 6 µg/ml human serum albumin (HSA) in 15 mM $Na_2CO_3$ and 35 mM $NaHCO_3$ (pH 9.6) over night at 4° C. and blocked with 2% skim milk powder in PBS-T for 1 h at room temperature. The plates were washed four times, prior to addition of 100 µl 1 µg/ml biotinylated HER2 per well and incubated for 1.5 h. After washing the wells four times, 100 µl Streptavidin-HRP (1:5000) (#P0397 Dako) per well were added and incubated for 1 h. The wells were washed four times and after the final wash, 100 µl developing solution (ImmunoPure) TMB (#34021 Pierce) was added to each well. After 20-30 minutes, 100 µl stop solution (2 M $H_2SO_4$) was added to each well. The absorbance at 450 nm was measured in an ELISA reader (Tecan). The results from the ABAS ELISA is presented in FIG. 29. The X axis of the diagrams of FIGS. 29A and 29B correspond to the numbering of the well in the 96 well plate in question—thus, FIG. 29A shows the ELISA results for a first 96 well plate, whereas FIG. 29B shows the results for a second plate.

DNA Sequence Analysis

Sequencing of DNA encoding the $Z_{HER2}$ variants analyzed in the ABAS-ELISA was performed with ABI PRISM; dGTP, BigDye Terminator v3.0 Ready Reaction Cycle Sequencing Kit (Applied Biosystems) according to the manufacturer's recommendations, using the biotinylated oligonucleotide AFFI-72 (5'-biotin-CGGAACCAGAGCCACCACCGG) (SEQ ID NO:82). The sequences were analyzed on an ABI PRISM 3100 Genetic Analyser (Applied Biosystems). The sequence analysis resulted in 130 unique sequences. Sequences originating from $Z_{HER2}$ variants that exhibited binding in the ABAS ELISA experiment, as evidenced by an absorbance value that is at least two times higher than the value of the negative control, are presented in FIG. 1 and identified in the sequence listing as SEQ ID NO: 6-76. The nomenclature of these HER2 binding Z variants is as follows. The variants isolated from the first plate of the ELISA experiment (FIG. 29A) are denoted $Z_{HER2\ 1NN}$, where NN corresponds to the number of the well in the first plate in which that particular polypeptide variant was analyzed. The variants isolated from the second plate of the ELISA experiment (FIG. 29B) are denoted $Z_{HER2:2NN}$, where NN corresponds to the number of the well in the second plate in which that particular polypeptide variant was analyzed.

Cloning and Protein Production

Figure 30:
FIG. 30 is a schematic illustration of the amino acid sequence of the fusion polypeptide produced in Examples 9 and 10. $Z_{HER2}$ represents a HER2 binding polypeptide according to the first aspect of the invention, and $His_6$ represents a hexahistidyl tag.

Selected HER2 binding polypeptides were expressed in E. coli cells using an expression vector encoding constructs that have been schematically illustrated in FIG. 30. The polypeptides were produced as fusions to an N-terminal hexahistidyl-tag. The $His_6$-tagged polypeptides $Z_{HER2:101}$, $Z_{HER2:107}$/$Z_{HER2:149}$, $Z_{HER2:202}$, $Z_{HER2:205}$, $Z_{HER2:207}$, $Z_{HER2:209}$, $Z_{HER2:222}$, $Z_{HER2:225}$ and $Z_{HER2:229}$ as well as $Z_{HER2\ A}$ were purified using a BioRobot 3000 (Qiagen) and the NI-NTA Superflow 96 BioRobot procedure under denaturating conditions. Purified, $His_6$-tagged proteins were dialyzed in PBS (2.68 mM KCl, 137 mM NaCl, 1.47 mM $KH_2PO_4$, 8.1 mM $Na_2HPO_4$, pH 7.4). The protein concentration of samples was calculated from the measured absorption value at 280 nm and the theoretical extinction coefficient of the respective protein.

Biosensor Analysis of the $His_6$-Tagged $Z_{HER2}$ Variants

Figure 31:
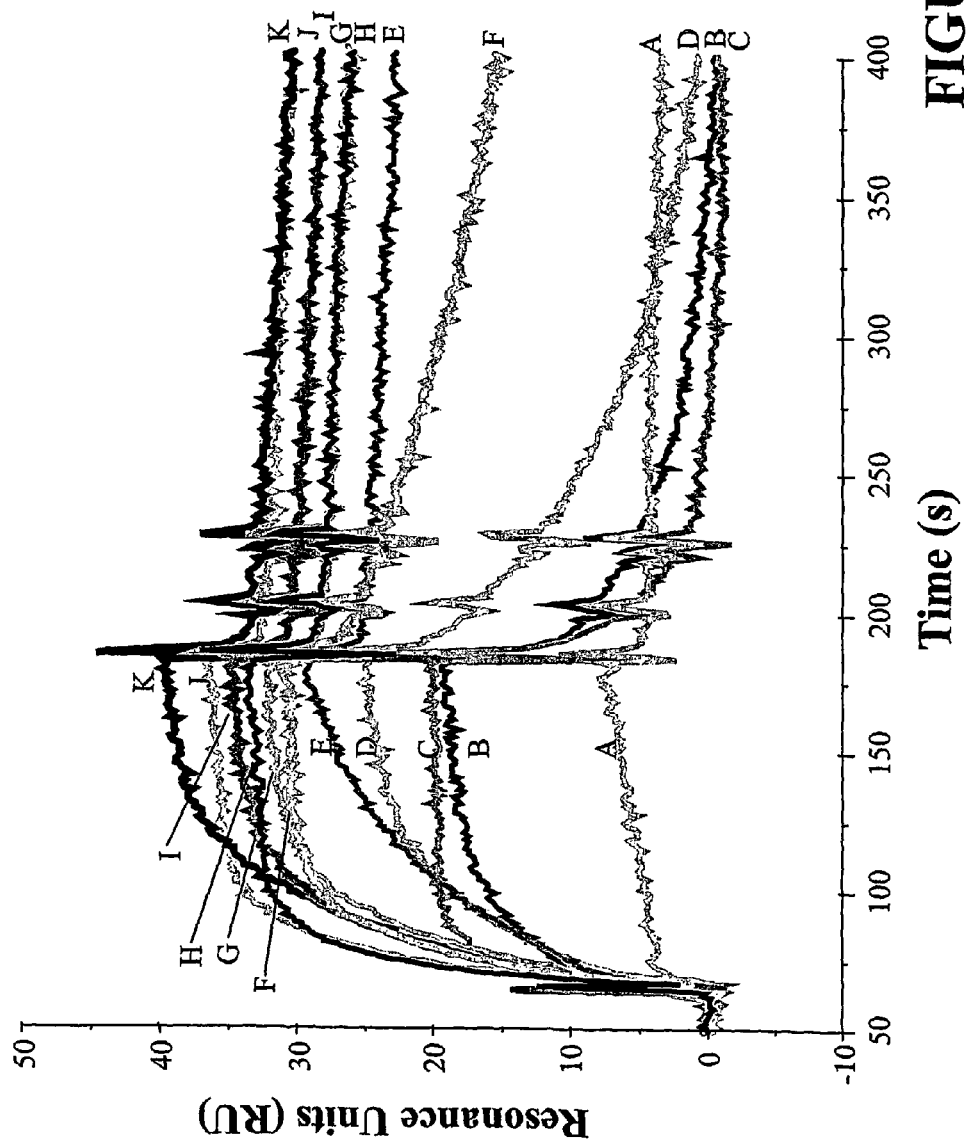
FIG. 31 is an overlay plot of sensograms obtained from 10 affinity matured HER2 binding polypeptides according to the invention, when injected over a HER2-coated surface at an approximate concentration of 50 nM. A: $Z_{HER2:205}$; B: $Z_{HER2:149}$; C: $Z_{HER2:202}$; D: $Z_{HER2\ A}$; E: $Z_{HER2:222}$; F: $Z_{HER2:225}$; G: $Z_{HER2:209}$; H: $Z_{HER2:229}$; I: $Z_{HER2:207}$; J: $Z_{HER2:107}$; K: $Z_{HER2:101}$. Note that $Z_{HER2\ A}$, isolated from the selection with the first generation library, was added in the study.

The interactions between the His-tagged $Z_{HER2}$ variants produced according to the preceding section and HER2 were analyzed using surface plasmon resonance in a Biacore® 2000 system (Biacore AB, Uppsala, Sweden). Human HER2 and IgG (immunoglobulin G) were immobilized in different flow cells by amine coupling onto the carboxylated dextran layer on surfaces of CM-5 chips, according to the manufacturer's recommendations. Immobilization of human HER2 and IgG resulted in 4600 and 5100 resonance units (RU), respectively. A third flow cell surface was activated and deactivated for use as blank during injections. The fusion polypeptides $Z_{HER2:101}$, $Z_{HER2:107}$, $Z_{HER2:149}$, $Z_{HER2:202}$, $Z_{HER2:205}$, $Z_{HER2:207}$, $Z_{HER2:209}$, $Z_{HER2:222}$, $Z_{HER2:225}$ and $Z_{HER2:229}$ were diluted in 1×HBS-EP (5 mM HEPES, 150 mM NaCl, 3.4 mM EDTA, 0.005% surfactant P-20, pH 7.4) to a final concentration of 50 nM, and injected at a constant flow rate of 10 µl/minute. The total injection time was 2 minutes (association) followed by a wash during 3 minutes (dissociation). The surfaces were regenerated with two injections of 25 mM HCl (30 seconds/injection). The responses measured in reference cells (activated/deactivated surface) were subtracted from the response measured in the cells with immobilized HER2. The ability of the purified proteins to interact with HER2 was confirmed, as illustrated by the sensograms of FIG. 31.

EXAMPLE 10

Identification and Characterization of Additional HER2-Binding Polypeptides

A comprehensive sequence analysis was performed of clones obtained after the third and fourth round from the selection described in Example 1. DNA was sequenced using the ABI PRISM dGTP, BigDye Terminator v3.0 Ready Reaction Cycle Sequencing Kit (Applied Biosystems) according to the manufacturer's recommendations and an ABI PRISME 3100 Genetic Analyser (Applied Biosystems). The biotinylated oligonucleotide AFFI-72 (5'-biotin - CGGAACCA-GAGCCACCACCGG) (SEQ ID NO:82) was used as a primer. Sequence analysis revealed 11 new polypeptide sequences, i e clones that had not been found in the study described in Example 1.

It was decided to express these Z variants in *E. coli* cells, using an expression vector encoding constructs that are schematically illustrated in FIG. 30. The polypeptides were thereby produced as fusions to an N-terminal hexahistidyl tag. The polypeptides were purified by Immobilized Metal ion Affinity Chromatography (IMAC) using a BioRobot 3000 (Qiagen) and the NI-NTA Superflow 96 BioRobot procedure under denaturating conditions. The eluted proteins were analyzed on SDS-PAGE. The buffers of purified $His_6$-tagged proteins were exchanged to 5 mM $NH_4Ac$ using PD-10 columns (Amersham Biosciences) according to the manufacturer's recommendations. Thereafter, the proteins were lyophilized and dissolved in HBS-EP (5 mM HEPES, 150 mM NaCl, 3.4 mM EDTA, 0.005% surfactant P-20, pH 7.4). Protein concentrations of samples were calculated from the measured absorption values at 280 nm and the theoretical extinction coefficient of the respective protein.

Biosensor Analysis of the $His_6$-Tagged $Z_{HER2}$ Variants

Figure 32:
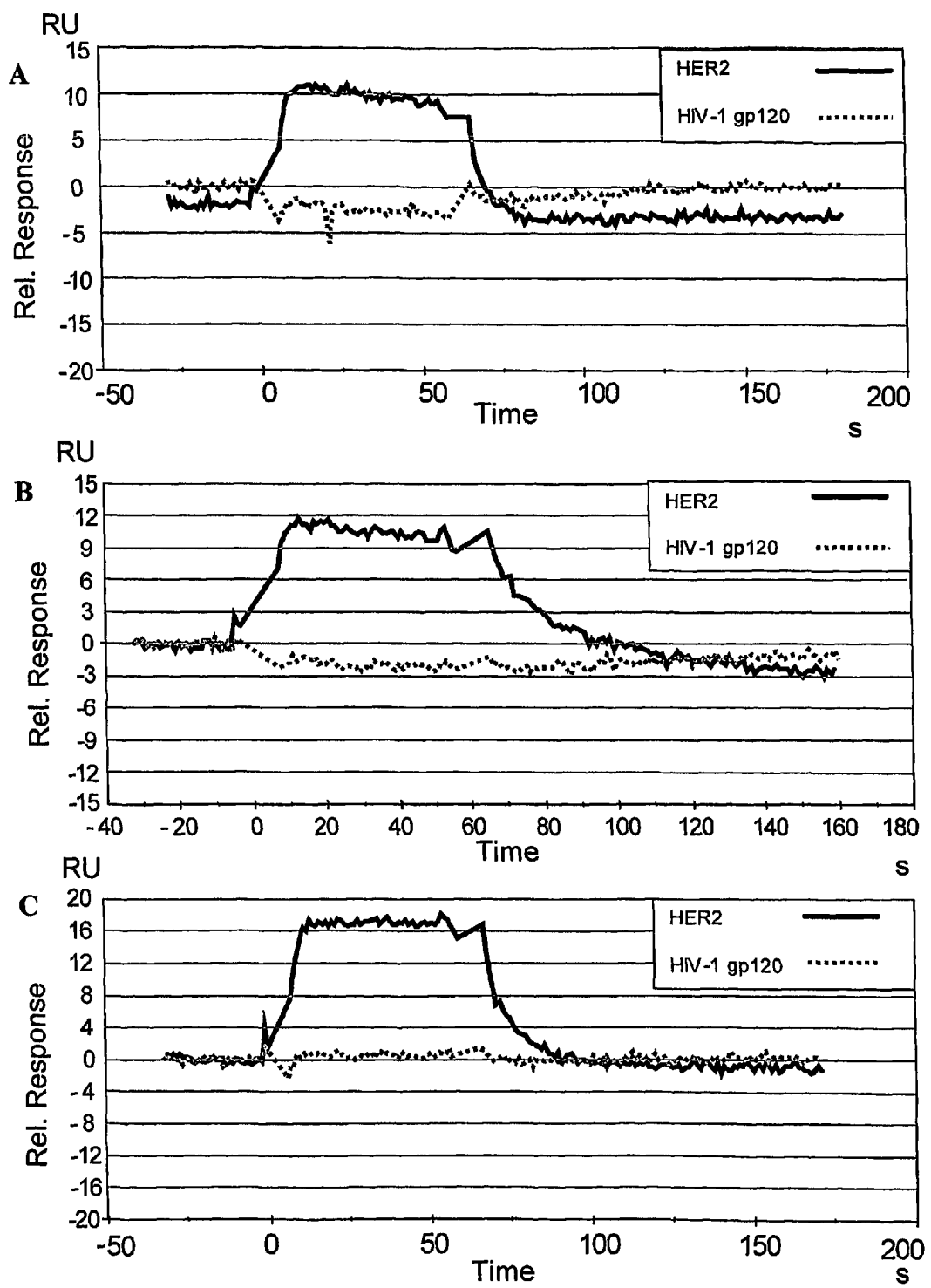
FIG. 32 shows binding analysis results of $Z_{HER2}$ variants, which possess specific HER2 binding activity. Resulting overlay sensograms from injections of (A) $Z_{HER2:3053}$ (B) $Z_{HER2:0434}$ (C) $Z_{HER2:0024*}$ over sensor chip surfaces containing either HER2 or HIV-1 gp120 as indicated.

The binding activity between the $His_6$-tagged $Z_{HER2}$ variants and HER2 was analyzed using a Biacore® 2000 (Biacore AB, Uppsala, Sweden). Human HER2 and HIV-1 gp120 (Protein Sciences Corporation, #2003-MN) were immobilized in different flow cells by amine coupling onto the carboxylated dextran layer on surfaces of CM-5 chips, according to the manufacturer's recommendations. Immobilization of human HER2 and HIV-1 gp120 resulted in 2631 and 3138 resonance units (RU), respectively. A third flow cell surface was activated and deactivated for use as blank during injections. The $Z_{HER2}$ variants were diluted in 1×HBS-EP (5 mM HEPES, 150 mM NaCl, 3.4 mM EDTA, 0.005% surfactant P-20, pH 7.4) to a final concentration of 1 µM, and injected at a constant flow rate of 10 µl/minute. The total injection time was 1 minute (association) followed by a wash during 3 minutes (dissociation). The surfaces were regenerated with an injection of 10 mM HCl during 30 seconds. The responses measured in reference cells (activated/deactivated surface) were subtracted from the response measured in the cells with immobilized HER2. Three of the purified proteins, $Z_{HER2:3053}$ $Z_{HER2:0434}$ and $Z_{HER2:0024*}$, bound specifically to HER2 as illustrated by the sensograms of FIG. 32. The sequences of these $Z_{HER2}$ variants are presented in FIG. 1, and identified in the sequence listing as SEQ ID NO:77-79.

The invention claimed is:

1. A polypeptide having a binding affinity for HER2, wherein the sequence of the polypeptide comprises the sequence of a protein Z, as set forth in SEQ ID NO:1, having from 4 to about 20 substitution mutations thereon, comprising at least four substitution mutations at the positions 13, 14, 28, 32 and 35 of SEQ ID NO:1, wherein the mutations comprise at least three of the following substitution mutations:
   (a) from phenylalanine to tyrosine at position 13 of SEQ ID NO:1,
   (b) from tyrosine to tryptophan at position 14 of SEQ ID NO:1,
   (c) from glutamine to arginine at position 32 of SEQ ID NO:1, and
   (d) from lysine to tyrosine at position 35 of SEQ ID NO:1.

2. A polypeptide according to claim 1, which has a binding affinity for HER2 such that the $K_D$ value of the interaction is at most $1 \times 10^{-6}$ M.

3. A polypeptide according to claim 2, which has a binding affinity for HER2 such that the $K_D$ value of the interaction is at most $1 \times 10^{-7}$ M.

4. A polypeptide according to claim 1, additionally comprising substitution mutations at one or more of the positions 9, 10, 11, 17, 18, 24, 25 and 27 of SEQ ID NO:1.

5. A polypeptide according to claim 1, comprising a substitution mutation at position 28 of SEQ ID NO:1 from asparagine to an amino acid residue selected from arginine and histidine.

6. A polypeptide according to claim 1, comprising a substitution mutation at position 28 of SEQ ID NO:1 from asparagine to arginine.

7. A polypeptide according to claim 1, comprising a substitution mutation at position 10 of SEQ ID NO:1 from glutamine to arginine.

8. A polypeptide according to claim 1, comprising a substitution mutation at position 11 of SEQ ID NO:1 from asparagine to threonine.

9. A polypeptide according to claim 1, comprising a substitution mutation at position 17 of SEQ ID NO:1 from leucine to valine.

10. A polypeptide according to claim 1, comprising a substitution mutation at position 27 of SEQ ID NO:1 from arginine to an amino acid residue selected from lysine and serine.

11. A polypeptide according to claim 1, the amino acid sequence of which is selected from the group consisting of SEQ ID NO: 2-4 and 6-79.

12. A polypeptide according to claim 11, the amino acid sequence of which is selected from the group consisting of SEQ ID NO:2-3.

13. A polypeptide according to claim 1, in which at least one of the asparagine residues present in the protein Z has been replaced with another amino acid residue.

14. A polypeptide according to claim 13, comprising substitution mutations at at least one position of SEQ ID NO:1 chosen from N3, N6, N11, N21, N23, N28, N43 and N52.

15. A polypeptide according to claim 14, comprising at least one of the following mutations of SEQ ID NO:1: N3A, N6A, N6D, N11S, N23T, N28A and N43E.

16. A polypeptide, which constitutes a fragment of a polypeptide according to claim 1, which fragment retains binding affinity for HER2.

17. A polypeptide according to claim 1, which comprises additional amino acid residues at either terminal.

18. A polypeptide according to claim 17, in which the additional amino acid residues comprise a cysteine residue at the N- or C-terminal of the polypeptide.

19. A polypeptide according to claim 17, in which the additional amino acid residues comprise a tag, preferably chosen from a hexahistidinyl tag, a myc tag and a flag tag.

20. A polypeptide according to claim 17, in which the additional amino acid residues comprise at least one functional polypeptide domain, so that the polypeptide is a fusion polypeptide between a first moiety, consisting of a polypeptide having a binding affinity for HER2, wherein the sequence of the polypeptide comprises the sequence of a protein Z, as set forth in SEQ ID NO:1, having from 4 to about 20 substitution mutations thereon and comprising at least four substitution mutations at the positions 13, 14, 28, 32 and 35 of SEQ ID NO:1, and at least one further moiety.

21. A polypeptide according to claim 20, in which the further moiety consists of one or more polypeptide(s) having a binding affinity for HER2, wherein the sequence of the polypeptide comprises the sequence of a protein Z, as set forth in SEQ ID NO:1, having from 4 to about 20 substitution mutations thereon and comprising at least four substitution mutations at the positions 13, 14, 28, 32, and 35 of SEQ ID NO:1, making the polypeptide a multimer of HER2 binding polypeptides, the sequences of which may be the same or different.

22. A polypeptide according to claim 20, in which the further moiety comprises at least one polypeptide domain capable of binding to a target molecule other than HER2.

23. A polypeptide according to claim 22, in which the further moiety comprises at least one polypeptide domain capable of binding to human serum albumin.

24. A polypeptide according to claim 23, in which the at least one polypeptide domain capable of binding to human serum albumin is the albumin binding domain of streptococcal protein G.

25. A polypeptide according to claim 22, in which the further moiety comprises a polypeptide wherein the sequence of the polypeptide comprises the sequence of a protein Z, as set forth in SEQ ID NO:1 having from 1 to about 20 substitution mutations.

26. A polypeptide according to claim 20, in which the further moiety is capable of enzymatic action.

27. A polypeptide according to claim 20, in which the further moiety is capable of fluorescent action.

28. A polypeptide according to claim 20, in which the further moiety is a phage coat protein.

29. A polypeptide according to claim 1, which further comprises a label group.

30. A polypeptide according to claim 29, in which the label group is selected from the group consisting of fluorescent labels, biotin and radioactive labels.

31. A polypeptide according to claim 1, coupled to a substance having an activity against cells overexpressing HER2.

32. A polypeptide according to claim 31, in which said substance having an activity against cells overexpressing HER2 is selected from the group consisting of cytotoxic agents, radioactive agents, enzymes for antibody-directed enzyme prodrug therapy applications (ADEPT), cytokines and procoagulant factors.

33. A method of treatment of at least one form of cancer characterized by overexpression of HER2, which method comprises administering to a subject in need of such treatment a therapeutically effective amount of a composition, which comprises a polypeptide according to claim 1 as an active substance.

34. A method of directing a substance having an anti-cancer activity to cells overexpressing HER2 in vivo, which method comprises administering a conjugate of said substance and a polypeptide according to claim 1 to a subject.

35. A method of detection of HER2 in a sample, comprising the steps: (i) providing a sample to be tested, (ii) applying a polypeptide according to claim 1 to the sample under conditions such that binding of the polypeptide to any HER2 present in the sample is enabled, (iii) removing non-bound polypeptide, and (iv) detecting bound polypeptide.

36. A method according to claim 35, in which the sample is a biological fluid sample, preferably a human blood plasma sample.

37. A method according to claim 35, in which the sample is a tissue sample.

38. A kit for in vivo diagnosis of HER2 overexpression, which kit comprises a polypeptide according to claim 1 labeled with a chelator, a diagnostic radioactive isotope, and reagents for the analysis of the incorporation efficiency.

39. The method according to claim 37, wherein the sample is a human tissue sample.

40. The method according to claim 37, wherein the sample is a biopsy sample from a human suffering from cancer.

41. A polypeptide according to claim 1, comprising all the substitution mutations (a)-(d).

42. A polypeptide according to claim 41, comprising at least the following mutations: F13Y, Y14W, N28R, Q32R and K35Y, wherein the amino acid positions are relative to SEQ ID NO:1.

* * * * *

SEQUENCE LISTING

```
<160> NUMBER OF SEQ ID NOS: 82

<210> SEQ ID NO 1
<211> LENGTH: 58
<212> TYPE: PRT
<213> ORGANISM: Artificial Sequence
<220> FEATURE:
<223> OTHER INFORMATION: Chemically Synthesized

<400> SEQUENCE: 1

Val Asp Asn Lys Phe Asn Lys Glu Gln Gln Asn Ala Phe Tyr Glu Ile
 1               5                  10                  15

Leu His Leu Pro Asn Leu Asn Glu Glu Gln Arg Asn Ala Phe Ile Gln
             20                  25                  30

Ser Leu Lys Asp Asp Pro Ser Gln Ser Ala Asn Leu Leu Ala Glu Ala
         35                  40                  45

Lys Lys Leu Asn Asp Ala Gln Ala Pro Lys
```

```
                50                  55

<210> SEQ ID NO 2
<211> LENGTH: 58
<212> TYPE: PRT
<213> ORGANISM: Artificial Sequence
<220> FEATURE:
<223> OTHER INFORMATION: Chemically Synthesized

<400> SEQUENCE: 2

Val Asp Asn Lys Phe Asn Lys Glu Leu Arg Gln Ala Tyr Trp Glu Ile
  1               5                  10                  15

Gln Ala Leu Pro Asn Leu Asn Trp Thr Gln Ser Arg Ala Phe Ile Arg
             20                  25                  30

Ser Leu Tyr Asp Asp Pro Ser Gln Ser Ala Asn Leu Leu Ala Glu Ala
         35                  40                  45

Lys Lys Leu Asn Asp Ala Gln Ala Pro Lys
        50                  55

<210> SEQ ID NO 3
<211> LENGTH: 58
<212> TYPE: PRT
<213> ORGANISM: Artificial Sequence
<220> FEATURE:
<223> OTHER INFORMATION: Chemically Synthesized

<400> SEQUENCE: 3

Val Asp Asn Lys Phe Asn Lys Glu Pro Lys Thr Ala Tyr Trp Glu Ile
  1               5                  10                  15

Val Lys Leu Pro Asn Leu Asn Pro Glu Gln Arg Arg Ala Phe Ile Arg
             20                  25                  30

Ser Leu Tyr Asp Asp Pro Ser Gln Ser Ala Asn Leu Leu Ala Glu Ala
         35                  40                  45

Lys Lys Leu Asn Asp Ala Gln Ala Pro Lys
        50                  55

<210> SEQ ID NO 4
<211> LENGTH: 58
<212> TYPE: PRT
<213> ORGANISM: Artificial Sequence
<220> FEATURE:
<223> OTHER INFORMATION: Chemically Synthesized

<400> SEQUENCE: 4

Val Asp Asn Lys Phe Asn Lys Glu Pro Arg Glu Ala Tyr Trp Glu Ile
  1               5                  10                  15

Gln Arg Leu Pro Asn Leu Asn Asn Lys Gln Lys Ala Ala Phe Ile Arg
             20                  25                  30

Ser Leu Tyr Asp Asp Pro Ser Gln Ser Ala Asn Leu Leu Ala Glu Ala
         35                  40                  45

Lys Lys Leu Asn Asp Ala Gln Ala Pro Lys
        50                  55

<210> SEQ ID NO 5
<211> LENGTH: 58
<212> TYPE: PRT
<213> ORGANISM: Artificial Sequence
<220> FEATURE:
<223> OTHER INFORMATION: Chemically Synthesized

<400> SEQUENCE: 5

Val Asp Asn Lys Phe Asn Lys Glu Trp Val Gln Ala Gly Ser Glu Ile
  1               5                  10                  15
```

```
Tyr Asn Leu Pro Asn Leu Asn Arg Ala Gln Met Arg Ala Phe Ile Arg
            20                  25                  30

Ser Leu Ser Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 6
<211> LENGTH: 58
<212> TYPE: PRT
<213> ORGANISM: Artificial Sequence
<220> FEATURE:
<223> OTHER INFORMATION: Chemically Synthesized

<400> SEQUENCE: 6

Val Asp Asn Lys Phe Asn Lys Glu Met Arg His Ala Tyr Trp Glu Ile
1               5                   10                  15

Val Lys Leu Pro Asn Leu Asn Pro Arg Gln Lys Arg Ala Phe Ile Arg
            20                  25                  30

Ser Leu Tyr Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 7
<211> LENGTH: 58
<212> TYPE: PRT
<213> ORGANISM: Artificial Sequence
<220> FEATURE:
<223> OTHER INFORMATION: Chemically Synthesized

<400> SEQUENCE: 7

Val Asp Asn Lys Phe Asn Lys Glu Met Arg Lys Ala Tyr Trp Glu Ile
1               5                   10                  15

Val Leu Leu Pro Asn Leu Asn Arg Arg Gln Ser Arg Ala Phe Ile Arg
            20                  25                  30

Ser Leu Tyr Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 8
<211> LENGTH: 58
<212> TYPE: PRT
<213> ORGANISM: Artificial Sequence
<220> FEATURE:
<223> OTHER INFORMATION: Chemically Synthesized

<400> SEQUENCE: 8

Val Asp Asn Lys Phe Asn Lys Glu Met Arg His Ala Tyr Trp Glu Ile
1               5                   10                  15

Ala Thr Leu Pro Asn Leu Asn Asn Val Gln Lys Arg Ala Phe Ile Arg
            20                  25                  30

Ser Leu Tyr Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 9
<211> LENGTH: 58
<212> TYPE: PRT
```

```
<213> ORGANISM: Artificial Sequence
<220> FEATURE:
<223> OTHER INFORMATION: Chemically Synthesized

<400> SEQUENCE: 9

Val Asp Asn Lys Phe Asn Lys Glu Phe Arg Thr Ala Tyr Trp Glu Ile
 1               5                  10                  15

Val Leu Leu Pro Asn Leu Asn Pro Gly Gln Ile Arg Ala Phe Ile Arg
            20                  25                  30

Ser Leu Tyr Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 10
<211> LENGTH: 58
<212> TYPE: PRT
<213> ORGANISM: Artificial Sequence
<220> FEATURE:
<223> OTHER INFORMATION: Chemically Synthesized

<400> SEQUENCE: 10

Val Asp Asn Lys Phe Asn Lys Glu Leu Arg Thr Ala Tyr Trp Glu Ile
 1               5                  10                  15

Val Leu Leu Pro Asn Leu Asn Thr Trp Gln Ile Arg Ala Phe Ile Arg
            20                  25                  30

Ser Leu Tyr Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 11
<211> LENGTH: 58
<212> TYPE: PRT
<213> ORGANISM: Artificial Sequence
<220> FEATURE:
<223> OTHER INFORMATION: Chemically Synthesized

<400> SEQUENCE: 11

Val Asp Asn Lys Phe Asn Lys Glu Pro Arg Lys Ala Tyr Trp Glu Ile
 1               5                  10                  15

Ala Val Leu Pro Asn Leu Asn Pro Ala Gln Lys Arg Ala Phe Ile Arg
            20                  25                  30

Ser Leu Tyr Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 12
<211> LENGTH: 58
<212> TYPE: PRT
<213> ORGANISM: Artificial Sequence
<220> FEATURE:
<223> OTHER INFORMATION: Chemically Synthesized

<400> SEQUENCE: 12

Val Asp Asn Lys Phe Asn Lys Glu Met Arg Asn Ala Tyr Trp Glu Ile
 1               5                  10                  15

Ala Leu Leu Pro Asn Leu Asn Asn Gln Gln Lys Arg Ala Phe Ile Arg
            20                  25                  30

Ser Leu Tyr Asp Asp Pro Ser Gln Ser Ala Asn Leu Leu Ala Glu Ala
        35                  40                  45
```

```
Lys Lys Leu Asn Asp Ala Gln Ala Pro Lys
    50                  55
```

<210> SEQ ID NO 13
<211> LENGTH: 58
<212> TYPE: PRT
<213> ORGANISM: Artificial Sequence
<220> FEATURE:
<223> OTHER INFORMATION: Chemically Synthesized

<400> SEQUENCE: 13

```
Val Asp Asn Lys Phe Asn Lys Glu Leu Arg Thr Ala Tyr Trp Glu Ile
 1               5                  10                  15

Val Gly Leu Pro Asn Leu Asn His Phe Gln Val Arg Ala Phe Ile Arg
            20                  25                  30

Ser Leu Tyr Asp Asp Pro Ser Gln Ser Ala Asn Leu Leu Ala Glu Ala
        35                  40                  45

Lys Lys Leu Asn Asp Ala Gln Ala Pro Lys
    50                  55
```

<210> SEQ ID NO 14
<211> LENGTH: 58
<212> TYPE: PRT
<213> ORGANISM: Artificial Sequence
<220> FEATURE:
<223> OTHER INFORMATION: Chemically Synthesized

<400> SEQUENCE: 14

```
Val Asp Asn Lys Phe Asn Lys Glu Leu Arg Thr Ala Tyr Trp Glu Ile
 1               5                  10                  15

Val Leu Leu Pro Asn Leu Asn Arg Trp Gln Ile Arg Ala Phe Ile Arg
            20                  25                  30

Ser Leu Tyr Asp Asp Pro Ser Gln Ser Ala Asn Leu Leu Ala Glu Ala
        35                  40                  45

Lys Lys Leu Asn Asp Ala Gln Ala Pro Lys
    50                  55
```

<210> SEQ ID NO 15
<211> LENGTH: 58
<212> TYPE: PRT
<213> ORGANISM: Artificial Sequence
<220> FEATURE:
<223> OTHER INFORMATION: Chemically Synthesized

<400> SEQUENCE: 15

```
Val Asp Asn Lys Phe Asn Lys Glu Ile Arg Asn Ala Tyr Trp Glu Ile
 1               5                  10                  15

Ala Leu Leu Pro Asn Leu Asn Asn Met Gln Lys Arg Ala Phe Ile Arg
            20                  25                  30

Ser Leu Tyr Asp Asp Pro Ser Gln Ser Ala Asn Leu Leu Ala Glu Ala
        35                  40                  45

Lys Lys Leu Asn Asp Ala Gln Ala Pro Lys
    50                  55
```

<210> SEQ ID NO 16
<211> LENGTH: 58
<212> TYPE: PRT
<213> ORGANISM: Artificial Sequence
<220> FEATURE:
<223> OTHER INFORMATION: Chemically Synthesized

<400> SEQUENCE: 16

Val Asp Asn Lys Phe Asn Lys Glu Phe Arg Lys Ala Tyr Trp Glu Ile
1               5                   10                  15

Val Val Leu Pro Asn Leu Asn Arg Met Gln Ile Arg Ala Phe Ile Arg
                20                  25                  30

Ser Leu Tyr Asp Asp Pro Ser Gln Ser Ala Asn Leu Leu Ala Glu Ala
            35                  40                  45

Lys Lys Leu Asn Asp Ala Gln Ala Pro Lys
        50                  55

<210> SEQ ID NO 17
<211> LENGTH: 58
<212> TYPE: PRT
<213> ORGANISM: Artificial Sequence
<220> FEATURE:
<223> OTHER INFORMATION: Chemically Synthesized

<400> SEQUENCE: 17

Val Asp Asn Lys Phe Asn Lys Glu Phe Arg Thr Ala Tyr Trp Glu Ile
1               5                   10                  15

Val Leu Leu Pro Asn Leu Asn Arg Glu Gln Gly Arg Ala Phe Ile Arg
                20                  25                  30

Ser Leu Tyr Asp Asp Pro Ser Gln Ser Ala Asn Leu Leu Ala Glu Ala
            35                  40                  45

Lys Lys Leu Asn Asp Ala Gln Ala Pro Lys
        50                  55

<210> SEQ ID NO 18
<211> LENGTH: 58
<212> TYPE: PRT
<213> ORGANISM: Artificial Sequence
<220> FEATURE:
<223> OTHER INFORMATION: Chemically Synthesized

<400> SEQUENCE: 18

Val Asp Asn Lys Phe Asn Lys Glu Met Arg Thr Ala Tyr Trp Glu Ile
1               5                   10                  15

Ala Thr Leu Pro Asn Leu Asn Asn Lys Gln Ile Arg Ala Phe Ile Arg
                20                  25                  30

Ser Leu Tyr Asp Asp Pro Ser Gln Ser Ala Asn Leu Leu Ala Glu Ala
            35                  40                  45

Lys Lys Leu Asn Asp Ala Gln Ala Pro Lys
        50                  55

<210> SEQ ID NO 19
<211> LENGTH: 58
<212> TYPE: PRT
<213> ORGANISM: Artificial Sequence
<220> FEATURE:
<223> OTHER INFORMATION: Chemically Synthesized

<400> SEQUENCE: 19

Val Asp Asn Lys Phe Asn Lys Glu Phe Arg Asn Ala Tyr Trp Glu Ile
1               5                   10                  15

Val Val Leu Pro Asn Leu Asn Asn Arg Gln Lys Arg Ala Phe Ile Arg
                20                  25                  30

Ser Leu Tyr Asp Asp Pro Ser Gln Ser Ala Asn Leu Leu Ala Glu Ala
            35                  40                  45

Lys Lys Leu Asn Asp Ala Gln Ala Pro Lys
        50                  55

<210> SEQ ID NO 20

```
<211> LENGTH: 58
<212> TYPE: PRT
<213> ORGANISM: Artificial Sequence
<220> FEATURE:
<223> OTHER INFORMATION: Chemically Synthesized

<400> SEQUENCE: 20

Val Asp Asn Lys Phe Asn Lys Glu Phe Arg Asn Ala Tyr Trp Glu Ile
 1               5                  10                  15

Ala Lys Leu Pro Asn Leu Asn Asn Gly Gln Lys Arg Ala Phe Ile Arg
            20                  25                  30

Ser Leu Tyr Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 21
<211> LENGTH: 58
<212> TYPE: PRT
<213> ORGANISM: Artificial Sequence
<220> FEATURE:
<223> OTHER INFORMATION: Chemically Synthesized

<400> SEQUENCE: 21

Val Asp Asn Lys Phe Asn Lys Glu Phe Arg Gln Ala Tyr Trp Glu Ile
 1               5                  10                  15

Ala Leu Leu Pro Asn Leu Asn His Ser Gln Thr Arg Ala Phe Ile Arg
            20                  25                  30

Ser Leu Tyr Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 22
<211> LENGTH: 58
<212> TYPE: PRT
<213> ORGANISM: Artificial Sequence
<220> FEATURE:
<223> OTHER INFORMATION: Chemically Synthesized

<400> SEQUENCE: 22

Val Asp Asn Lys Phe Asn Lys Glu Pro Arg His Ala Tyr Trp Glu Ile
 1               5                  10                  15

Val Lys Leu Pro Asn Leu Asn Ser Leu Gln Lys Arg Ala Phe Ile Arg
            20                  25                  30

Ser Leu Tyr Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 23
<211> LENGTH: 58
<212> TYPE: PRT
<213> ORGANISM: Artificial Sequence
<220> FEATURE:
<223> OTHER INFORMATION: Chemically Synthesized

<400> SEQUENCE: 23

Val Asp Asn Lys Phe Asn Lys Glu Leu Arg Thr Ala Tyr Trp Glu Ile
 1               5                  10                  15

Val Gly Leu Pro Asn Leu Asn Ser Arg Gln Ser Arg Ala Phe Ile Arg
            20                  25                  30
```

Ser Leu Tyr Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 24
<211> LENGTH: 58
<212> TYPE: PRT
<213> ORGANISM: Artificial Sequence
<220> FEATURE:
<223> OTHER INFORMATION: Chemically Synthesized

<400> SEQUENCE: 24

Val Asp Asn Lys Phe Asn Lys Glu Leu Arg Thr Ala Tyr Trp Glu Ile
1               5                   10                  15

Ala Gly Leu Pro Asn Leu Asn Pro Lys Gln Lys Arg Ala Phe Ile Arg
            20                  25                  30

Ser Leu Tyr Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 25
<211> LENGTH: 58
<212> TYPE: PRT
<213> ORGANISM: Artificial Sequence
<220> FEATURE:
<223> OTHER INFORMATION: Chemically Synthesized

<400> SEQUENCE: 25

Val Asp Asn Lys Phe Asn Lys Glu Met Arg Lys Ala Tyr Trp Glu Ile
1               5                   10                  15

Thr Gln Leu Pro Asn Leu Asn Thr Arg Gln Thr Arg Ala Phe Ile Arg
            20                  25                  30

Ser Leu Tyr Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 26
<211> LENGTH: 58
<212> TYPE: PRT
<213> ORGANISM: Artificial Sequence
<220> FEATURE:
<223> OTHER INFORMATION: Chemically Synthesized

<400> SEQUENCE: 26

Val Asp Asn Lys Phe Asn Lys Glu Phe Arg Lys Ala Tyr Trp Glu Ile
1               5                   10                  15

Val Leu Leu Pro Asn Leu Asn Trp Glu Gln Asn Arg Ala Phe Ile Arg
            20                  25                  30

Ser Leu Tyr Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 27
<211> LENGTH: 58
<212> TYPE: PRT
<213> ORGANISM: Artificial Sequence
<220> FEATURE:
<223> OTHER INFORMATION: Chemically Synthesized -continued

```
<400> SEQUENCE: 27

Val Asp Asn Lys Phe Asn Lys Glu Phe Arg Lys Ala Tyr Trp Glu Ile
1               5                   10                  15

Thr Gln Leu Pro Asn Leu Asn Arg Glu Gln Asn Arg Ala Phe Ile Arg
            20                  25                  30

Ser Leu Tyr Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 28
<211> LENGTH: 58
<212> TYPE: PRT
<213> ORGANISM: Artificial Sequence
<220> FEATURE:
<223> OTHER INFORMATION: Chemically Synthesized

<400> SEQUENCE: 28

Val Asp Asn Lys Phe Asn Lys Glu Met Arg His Ala Tyr Trp Glu Ile
1               5                   10                  15

Ala Thr Leu Pro Asn Leu Asn Thr Asn Gln Ser Arg Ala Phe Ile Arg
            20                  25                  30

Ser Leu Tyr Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 29
<211> LENGTH: 58
<212> TYPE: PRT
<213> ORGANISM: Artificial Sequence
<220> FEATURE:
<223> OTHER INFORMATION: Chemically Synthesized

<400> SEQUENCE: 29

Val Asp Asn Lys Phe Asn Lys Glu Met Arg Asn Ala Tyr Trp Glu Ile
1               5                   10                  15

Val Gly Leu Pro Asn Leu Asn Arg Trp Gln Ser Arg Ala Phe Ile Arg
            20                  25                  30

Ser Leu Tyr Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 30
<211> LENGTH: 58
<212> TYPE: PRT
<213> ORGANISM: Artificial Sequence
<220> FEATURE:
<223> OTHER INFORMATION: Chemically Synthesized

<400> SEQUENCE: 30

Val Asp Asn Lys Phe Asn Lys Glu Leu Arg Asn Ala Tyr Trp Glu Ile
1               5                   10                  15

Val Lys Leu Pro Asn Leu Asn Pro Trp Gln His Arg Ala Phe Ile Arg
            20                  25                  30

Ser Leu Tyr Asp Asp Pro Ser Gln Ser Ala Asn Leu Leu Ala Glu Ala
        35                  40                  45

Lys Lys Leu Asn Asp Ala Gln Ala Pro Lys
    50                  55
```

-continued

<210> SEQ ID NO 31
<211> LENGTH: 58
<212> TYPE: PRT
<213> ORGANISM: Artificial Sequence
<220> FEATURE:
<223> OTHER INFORMATION: Chemically Synthesized

<400> SEQUENCE: 31

Val Asp Asn Lys Phe Asn Lys Glu Phe Arg Thr Ala Tyr Trp Glu Ile
1               5                   10                  15

Val Lys Leu Pro Asn Leu Asn Val Arg Gln Ser Arg Ala Phe Ile Arg
            20                  25                  30

Ser Leu Tyr Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 32
<211> LENGTH: 58
<212> TYPE: PRT
<213> ORGANISM: Artificial Sequence
<220> FEATURE:
<223> OTHER INFORMATION: Chemically Synthesized

<400> SEQUENCE: 32

Val Asp Asn Lys Phe Asn Lys Glu Asn Arg Thr Ala Tyr Trp Glu Ile
1               5                   10                  15

Val Lys Leu Pro Asn Leu Asn Asp Tyr Gln Lys Arg Ala Phe Ile Arg
            20                  25                  30

Ser Leu Tyr Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 33
<211> LENGTH: 58
<212> TYPE: PRT
<213> ORGANISM: Artificial Sequence
<220> FEATURE:
<223> OTHER INFORMATION: Chemically Synthesized

<400> SEQUENCE: 33

Val Asp Asn Lys Phe Asn Lys Glu Phe Arg Thr Ala Tyr Trp Glu Ile
1               5                   10                  15

Thr Gln Leu Pro Asn Leu Asn Arg Leu Gln Ser Arg Ala Phe Ile Arg
            20                  25                  30

Ser Leu Tyr Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 34
<211> LENGTH: 58
<212> TYPE: PRT
<213> ORGANISM: Artificial Sequence
<220> FEATURE:
<223> OTHER INFORMATION: Chemically Synthesized

<400> SEQUENCE: 34

Val Asp Asn Lys Phe Asn Lys Glu Ile Arg Thr Ala Tyr Trp Glu Ile
1               5                   10                  15

Ala Gly Leu Pro Asn Leu Asn Ala Gln Gln Lys Arg Ala Phe Ile Arg

```
                 20                  25                  30

Ser Leu Tyr Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 35
<211> LENGTH: 58
<212> TYPE: PRT
<213> ORGANISM: Artificial Sequence
<220> FEATURE:
<223> OTHER INFORMATION: Chemically Synthesized

<400> SEQUENCE: 35

Val Asp Asn Lys Phe Asn Lys Glu Met Arg Gln Ala Tyr Trp Glu Ile
1               5                   10                  15

Val Arg Leu Pro Asn Leu Asn Ala Asp Gln Lys Arg Ala Phe Ile Arg
            20                  25                  30

Ser Leu Tyr Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 36
<211> LENGTH: 58
<212> TYPE: PRT
<213> ORGANISM: Artificial Sequence
<220> FEATURE:
<223> OTHER INFORMATION: Chemically Synthesized

<400> SEQUENCE: 36

Val Asp Asn Lys Phe Asn Lys Glu Met Arg Asn Ala Tyr Trp Glu Ile
1               5                   10                  15

Val Thr Leu Pro Asn Leu Asn Lys Thr Gln Ser Arg Ala Phe Ile Arg
            20                  25                  30

Ser Leu Tyr Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 37
<211> LENGTH: 58
<212> TYPE: PRT
<213> ORGANISM: Artificial Sequence
<220> FEATURE:
<223> OTHER INFORMATION: Chemically Synthesized

<400> SEQUENCE: 37

Val Asp Asn Lys Phe Asn Lys Glu Met Arg Gln Ala Tyr Trp Glu Ile
1               5                   10                  15

Val Lys Leu Pro Asn Leu Asn Pro Gly Gln Ser Arg Ala Phe Ile Arg
            20                  25                  30

Ser Leu Tyr Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 38
<211> LENGTH: 58
<212> TYPE: PRT
<213> ORGANISM: Artificial Sequence
<220> FEATURE:
```

<223> OTHER INFORMATION: Chemically Synthesized

<400> SEQUENCE: 38

Val Asp Asn Lys Phe Asn Lys Glu Met Arg Thr Ala Tyr Trp Glu Ile
1               5                   10                  15

Ala Leu Leu Pro Asn Leu Asn Asn Met Gln Lys Arg Ala Phe Ile Arg
            20                  25                  30

Ser Leu Tyr Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 39
<211> LENGTH: 58
<212> TYPE: PRT
<213> ORGANISM: Artificial Sequence
<220> FEATURE:
<223> OTHER INFORMATION: Chemically Synthesized

<400> SEQUENCE: 39

Val Asp Asn Lys Phe Asn Lys Glu Phe Arg Lys Ala Tyr Trp Glu Ile
1               5                   10                  15

Ala Leu Leu Pro Asn Leu Asn Lys Trp Gln Ser Arg Ala Phe Ile Arg
            20                  25                  30

Ser Leu Tyr Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 40
<211> LENGTH: 58
<212> TYPE: PRT
<213> ORGANISM: Artificial Sequence
<220> FEATURE:
<223> OTHER INFORMATION: Chemically Synthesized

<400> SEQUENCE: 40

Val Asp Asn Lys Phe Asn Lys Glu Met Arg Lys Ala Tyr Trp Glu Ile
1               5                   10                  15

Ala Leu Leu Pro Asn Leu Asn Arg Trp Gln Ile Arg Ala Phe Ile Arg
            20                  25                  30

Ser Leu Tyr Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 41
<211> LENGTH: 58
<212> TYPE: PRT
<213> ORGANISM: Artificial Sequence
<220> FEATURE:
<223> OTHER INFORMATION: Chemically Synthesized

<400> SEQUENCE: 41

Val Asp Asn Lys Phe Asn Lys Glu Met Arg Gln Ala Tyr Trp Glu Ile
1               5                   10                  15

Val Leu Leu Pro Asn Leu Asn Arg Trp Gln Thr Arg Ala Phe Ile Arg
            20                  25                  30

Ser Leu Tyr Asp Asp Pro Ser Gln Ser Ala Asn Leu Leu Ala Glu Ala
        35                  40                  45

Lys Lys Leu Asn Asp Ala Gln Ala Pro Lys

<210> SEQ ID NO 42
<211> LENGTH: 58
<212> TYPE: PRT
<213> ORGANISM: Artificial Sequence
<220> FEATURE:
<223> OTHER INFORMATION: Chemically Synthesized

<400> SEQUENCE: 42

Val Asp Asn Lys Phe Asn Lys Glu Leu Arg Lys Ala Tyr Trp Glu Ile
1               5                   10                  15

Val Gly Leu Pro Asn Leu Asn Arg Glu Gln Asn Arg Ala Phe Ile Arg
            20                  25                  30

Ser Leu Tyr Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 43
<211> LENGTH: 58
<212> TYPE: PRT
<213> ORGANISM: Artificial Sequence
<220> FEATURE:
<223> OTHER INFORMATION: Chemically Synthesized

<400> SEQUENCE: 43

Val Asp Asn Lys Phe Asn Lys Glu Met Arg Thr Ala Tyr Trp Glu Ile
1               5                   10                  15

Val Gly Leu Pro Asn Leu Asn Asn Gln Gln Lys Arg Ala Phe Ile Arg
            20                  25                  30

Ser Leu Tyr Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 44
<211> LENGTH: 58
<212> TYPE: PRT
<213> ORGANISM: Artificial Sequence
<220> FEATURE:
<223> OTHER INFORMATION: Chemically Synthesized

<400> SEQUENCE: 44

Val Asp Asn Lys Phe Asn Lys Glu Leu Arg Thr Ala Tyr Trp Glu Ile
1               5                   10                  15

Val Arg Leu Pro Asn Leu Asn Val Asn Gln Thr Arg Ala Phe Ile Arg
            20                  25                  30

Ser Leu Tyr Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 45
<211> LENGTH: 58
<212> TYPE: PRT
<213> ORGANISM: Artificial Sequence
<220> FEATURE:
<223> OTHER INFORMATION: Chemically Synthesized

<400> SEQUENCE: 45

Val Asp Asn Lys Phe Asn Lys Glu Phe Arg His Ala Tyr Trp Glu Ile
1               5                   10                  15

Val Arg Leu Pro Asn Leu Asn Ala Gly Gln His Arg Ala Phe Ile Arg
            20                  25                  30

Ser Leu Tyr Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 46
<211> LENGTH: 58
<212> TYPE: PRT
<213> ORGANISM: Artificial Sequence
<220> FEATURE:
<223> OTHER INFORMATION: Chemically Synthesized

<400> SEQUENCE: 46

Val Asp Asn Lys Phe Asn Lys Glu Leu Arg Lys Ala Tyr Trp Glu Ile
1               5                   10                  15

Val Thr Leu Pro Asn Leu Asn Pro Ser Gln His Arg Ala Phe Ile Arg
            20                  25                  30

Ser Leu Tyr Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 47
<211> LENGTH: 58
<212> TYPE: PRT
<213> ORGANISM: Artificial Sequence
<220> FEATURE:
<223> OTHER INFORMATION: Chemically Synthesized

<400> SEQUENCE: 47

Val Asp Asn Lys Phe Asn Lys Glu Met Arg Thr Ala Tyr Trp Glu Ile
1               5                   10                  15

Ala Lys Leu Pro Asn Leu Asn Pro Pro Gln Lys Arg Ala Phe Ile Arg
            20                  25                  30

Ser Leu Tyr Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 48
<211> LENGTH: 58
<212> TYPE: PRT
<213> ORGANISM: Artificial Sequence
<220> FEATURE:
<223> OTHER INFORMATION: Chemically Synthesized

<400> SEQUENCE: 48

Val Asp Asn Lys Phe Asn Lys Glu Leu Arg Thr Ala Tyr Trp Glu Ile
1               5                   10                  15

Val Thr Leu Pro Asn Leu Asn Thr Ser Gln Thr Arg Ala Phe Ile Arg
            20                  25                  30

Ser Leu Tyr Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 49
<211> LENGTH: 58
<212> TYPE: PRT

<213> ORGANISM: Artificial Sequence
<220> FEATURE:
<223> OTHER INFORMATION: Chemically Synthesized

<400> SEQUENCE: 49

Val Asp Asn Lys Phe Asn Lys Glu Leu Arg Lys Ala Tyr Trp Glu Ile
1               5                   10                  15

Gln Val Leu Pro Asn Leu Asn Val Arg Gln Lys Arg Ala Phe Ile Arg
            20                  25                  30

Ser Leu Tyr Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 50
<211> LENGTH: 58
<212> TYPE: PRT
<213> ORGANISM: Artificial Sequence
<220> FEATURE:
<223> OTHER INFORMATION: Chemically Synthesized

<400> SEQUENCE: 50

Val Asp Asn Lys Phe Asn Lys Glu Pro Arg Gln Ala Tyr Trp Glu Ile
1               5                   10                  15

Val Leu Leu Pro Asn Leu Asn Arg Phe Gln Lys Arg Ala Phe Ile Arg
            20                  25                  30

Ser Leu Tyr Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 51
<211> LENGTH: 58
<212> TYPE: PRT
<213> ORGANISM: Artificial Sequence
<220> FEATURE:
<223> OTHER INFORMATION: Chemically Synthesized

<400> SEQUENCE: 51

Val Asp Asn Lys Phe Asn Lys Glu Met Arg Asn Ala Tyr Trp Glu Ile
1               5                   10                  15

Val Gly Leu Pro Asn Leu Asn Gln Gly Gln Lys Arg Ala Phe Ile Arg
            20                  25                  30

Ser Leu Tyr Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 52
<211> LENGTH: 58
<212> TYPE: PRT
<213> ORGANISM: Artificial Sequence
<220> FEATURE:
<223> OTHER INFORMATION: Chemically Synthesized

<400> SEQUENCE: 52

Val Asp Asn Lys Phe Asn Lys Glu Pro Arg Gln Ala Tyr Trp Glu Ile
1               5                   10                  15

Val Lys Leu Pro Asn Leu Asn Asn Ser Gln Arg Arg Ala Phe Ile Arg
            20                  25                  30

Ser Leu Tyr Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 53
<211> LENGTH: 58
<212> TYPE: PRT
<213> ORGANISM: Artificial Sequence
<220> FEATURE:
<223> OTHER INFORMATION: Chemically Synthesized

<400> SEQUENCE: 53

Val Asp Asn Lys Phe Asn Lys Glu Asn Arg Thr Ala Tyr Trp Glu Ile
1               5                   10                  15

Val Arg Leu Pro Asn Leu Asn Ser Ala Gln Lys Arg Ala Phe Ile Arg
            20                  25                  30

Ser Leu Tyr Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 54
<211> LENGTH: 58
<212> TYPE: PRT
<213> ORGANISM: Artificial Sequence
<220> FEATURE:
<223> OTHER INFORMATION: Chemically Synthesized

<400> SEQUENCE: 54

Val Asp Asn Lys Phe Asn Lys Glu Met Arg Asn Ala Tyr Trp Glu Ile
1               5                   10                  15

Val Leu Leu Pro Asn Leu Asn Arg Trp Gln Ser Arg Ala Phe Ile Arg
            20                  25                  30

Ser Leu Tyr Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 55
<211> LENGTH: 58
<212> TYPE: PRT
<213> ORGANISM: Artificial Sequence
<220> FEATURE:
<223> OTHER INFORMATION: Chemically Synthesized

<400> SEQUENCE: 55

Val Asp Asn Lys Phe Asn Lys Glu Met Arg Thr Ala Tyr Trp Glu Ile
1               5                   10                  15

Val Ile Leu Pro Asn Leu Asn Lys Trp Gln Ile Arg Ala Phe Ile Arg
            20                  25                  30

Ser Leu Tyr Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 56
<211> LENGTH: 58
<212> TYPE: PRT
<213> ORGANISM: Artificial Sequence
<220> FEATURE:
<223> OTHER INFORMATION: Chemically Synthesized

<400> SEQUENCE: 56

Val Asp Asn Lys Phe Asn Lys Glu Met Arg Asn Ala Tyr Trp Glu Ile
1               5                   10                  15

Ala Leu Leu Pro Asn Leu Asn Val Ala Gln Lys Arg Ala Phe Ile Arg
            20                  25                  30

Ser Leu Tyr Asp Asp Pro Ser Gln Ser Ala Asn Leu Leu Ala Glu Ala
            35                  40                  45

Lys Lys Leu Asn Asp Ala Gln Ala Pro Lys
            50                  55

<210> SEQ ID NO 57
<211> LENGTH: 58
<212> TYPE: PRT
<213> ORGANISM: Artificial Sequence
<220> FEATURE:
<223> OTHER INFORMATION: Chemically Synthesized

<400> SEQUENCE: 57

Val Asp Asn Lys Phe Asn Lys Glu Phe Arg Gln Ala Tyr Trp Glu Ile
1               5                   10                  15

Val Lys Leu Pro Asn Leu Asn Ser Gly Gln His Arg Ala Phe Ile Arg
            20                  25                  30

Ser Leu Tyr Asp Asp Pro Ser Gln Ser Ala Asn Leu Leu Ala Glu Ala
            35                  40                  45

Lys Lys Leu Asn Asp Ala Gln Ala Pro Lys
            50                  55

<210> SEQ ID NO 58
<211> LENGTH: 58
<212> TYPE: PRT
<213> ORGANISM: Artificial Sequence
<220> FEATURE:
<223> OTHER INFORMATION: Chemically Synthesized

<400> SEQUENCE: 58

Val Asp Asn Lys Phe Asn Lys Glu Met Arg Thr Ala Tyr Trp Glu Ile
1               5                   10                  15

Val Lys Leu Pro Asn Leu Asn Ile Ala Gln Asn Arg Ala Phe Ile Arg
            20                  25                  30

Ser Leu Tyr Asp Asp Pro Ser Gln Ser Ala Asn Leu Leu Ala Glu Ala
            35                  40                  45

Lys Lys Leu Asn Asp Ala Gln Ala Pro Lys
            50                  55

<210> SEQ ID NO 59
<211> LENGTH: 58
<212> TYPE: PRT
<213> ORGANISM: Artificial Sequence
<220> FEATURE:
<223> OTHER INFORMATION: Chemically Synthesized

<400> SEQUENCE: 59

Val Asp Asn Lys Phe Asn Lys Glu Leu Arg Thr Ala Tyr Trp Glu Ile
1               5                   10                  15

Val Ser Leu Pro Asn Leu Asn Arg Asn Gln Ser Arg Ala Phe Ile Arg
            20                  25                  30

Ser Leu Tyr Asp Asp Pro Ser Gln Ser Ala Asn Leu Leu Ala Glu Ala
            35                  40                  45

Lys Lys Leu Asn Asp Ala Gln Ala Pro Lys
            50                  55

<210> SEQ ID NO 60

```
<211> LENGTH: 58
<212> TYPE: PRT
<213> ORGANISM: Artificial Sequence
<220> FEATURE:
<223> OTHER INFORMATION: Chemically Synthesized

<400> SEQUENCE: 60

Val Asp Asn Lys Phe Asn Lys Glu Met Arg Asn Ala Tyr Trp Glu Ile
 1               5                  10                  15

Val Lys Leu Pro Asn Leu Asn Pro Gly Gln Ser Arg Ala Phe Ile Arg
            20                  25                  30

Ser Leu Tyr Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 61
<211> LENGTH: 58
<212> TYPE: PRT
<213> ORGANISM: Artificial Sequence
<220> FEATURE:
<223> OTHER INFORMATION: Chemically Synthesized

<400> SEQUENCE: 61

Val Asp Asn Lys Phe Asn Lys Glu Met Arg Gln Ala Tyr Trp Glu Ile
 1               5                  10                  15

Ala Leu Leu Pro Asn Leu Asn Arg Trp Gln Ile Arg Ala Phe Ile Arg
            20                  25                  30

Ser Leu Tyr Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 62
<211> LENGTH: 58
<212> TYPE: PRT
<213> ORGANISM: Artificial Sequence
<220> FEATURE:
<223> OTHER INFORMATION: Chemically Synthesized

<400> SEQUENCE: 62

Val Asp Asn Lys Phe Asn Lys Glu Phe Arg Thr Ala Tyr Trp Glu Ile
 1               5                  10                  15

Ala Val Leu Pro Asn Leu Asn Asn Gln Gln Lys Arg Ala Phe Ile Arg
            20                  25                  30

Ser Leu Tyr Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 63
<211> LENGTH: 58
<212> TYPE: PRT
<213> ORGANISM: Artificial Sequence
<220> FEATURE:
<223> OTHER INFORMATION: Chemically Synthesized

<400> SEQUENCE: 63

Val Asp Asn Lys Phe Asn Lys Glu Cys Arg Thr Ala Tyr Trp Glu Ile
 1               5                  10                  15

Val Lys Leu Pro Asn Leu Asn Asn Ala Gln Lys Arg Ala Phe Ile Arg
            20                  25                  30
```

Ser Leu Tyr Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 64
<211> LENGTH: 58
<212> TYPE: PRT
<213> ORGANISM: Artificial Sequence
<220> FEATURE:
<223> OTHER INFORMATION: Chemically Synthesized

<400> SEQUENCE: 64

Val Asp Asn Lys Phe Asn Lys Glu Pro Lys Thr Ala Tyr Trp Glu Ile
1               5                   10                  15

Val Val Leu Pro Asn Leu Asn Ser Lys Gln Lys Arg Ala Phe Ile Arg
            20                  25                  30

Ser Leu Tyr Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 65
<211> LENGTH: 58
<212> TYPE: PRT
<213> ORGANISM: Artificial Sequence
<220> FEATURE:
<223> OTHER INFORMATION: Chemically Synthesized

<400> SEQUENCE: 65

Val Asp Asn Lys Phe Asn Lys Glu Met Arg Asn Ala Tyr Trp Glu Ile
1               5                   10                  15

Val Thr Leu Pro Asn Leu Asn Lys Trp Gln Ile Arg Ala Phe Ile Arg
            20                  25                  30

Ser Leu Tyr Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 66
<211> LENGTH: 58
<212> TYPE: PRT
<213> ORGANISM: Artificial Sequence
<220> FEATURE:
<223> OTHER INFORMATION: Chemically Synthesized

<400> SEQUENCE: 66

Val Asp Asn Lys Phe Asn Lys Glu Met Arg Lys Ala Tyr Trp Glu Ile
1               5                   10                  15

Ala Thr Leu Pro Asn Leu Asn Lys Ser Gln Ser Arg Ala Phe Ile Arg
            20                  25                  30

Ser Leu Tyr Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 67
<211> LENGTH: 58
<212> TYPE: PRT
<213> ORGANISM: Artificial Sequence
<220> FEATURE:
<223> OTHER INFORMATION: Chemically Synthesized -continued

```
<400> SEQUENCE: 67

Val Asp Asn Lys Phe Asn Lys Glu Phe Arg Thr Ala Tyr Trp Glu Ile
1               5                   10                  15

Val Thr Leu Pro Asn Leu Asn Val Gly Gln Thr Arg Ala Phe Ile Arg
            20                  25                  30

Ser Leu Tyr Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 68
<211> LENGTH: 58
<212> TYPE: PRT
<213> ORGANISM: Artificial Sequence
<220> FEATURE:
<223> OTHER INFORMATION: Chemically Synthesized

<400> SEQUENCE: 68

Val Asp Asn Lys Phe Asn Lys Glu Leu Arg Thr Ala Tyr Trp Glu Ile
1               5                   10                  15

Val Gly Leu Pro Asn Leu Asn Thr Arg Gln Ser Arg Ala Phe Ile Arg
            20                  25                  30

Ser Leu Tyr Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 69
<211> LENGTH: 58
<212> TYPE: PRT
<213> ORGANISM: Artificial Sequence
<220> FEATURE:
<223> OTHER INFORMATION: Chemically Synthesized

<400> SEQUENCE: 69

Val Asp Asn Lys Phe Asn Lys Glu Leu Arg His Ala Tyr Trp Glu Ile
1               5                   10                  15

Val Gln Leu Pro Asn Leu Asn Arg Glu Gln Gly Arg Ala Phe Ile Arg
            20                  25                  30

Ser Leu Tyr Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 70
<211> LENGTH: 58
<212> TYPE: PRT
<213> ORGANISM: Artificial Sequence
<220> FEATURE:
<223> OTHER INFORMATION: Chemically Synthesized

<400> SEQUENCE: 70

Val Asp Asn Lys Phe Asn Lys Glu Phe Arg His Ala Tyr Trp Glu Ile
1               5                   10                  15

Ile Lys Leu Pro Asn Leu Asn Gly Lys Gln His Arg Ala Phe Ile Arg
            20                  25                  30

Ser Leu Tyr Asp Asp Pro Ser Gln Ser Ala Asn Leu Leu Ala Glu Ala
        35                  40                  45

Lys Lys Leu Asn Asp Ala Gln Ala Pro Lys
    50                  55
```

<210> SEQ ID NO 71
<211> LENGTH: 58
<212> TYPE: PRT
<213> ORGANISM: Artificial Sequence
<220> FEATURE:
<223> OTHER INFORMATION: Chemically Synthesized

<400> SEQUENCE: 71

Val Asp Asn Lys Phe Asn Lys Glu Met Arg Thr Ala Tyr Trp Glu Ile
1               5                   10                  15

Val Ser Leu Pro Asn Leu Asn Thr Leu Gln Ser Arg Ala Phe Ile Arg
            20                  25                  30

Ser Leu Tyr Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 72
<211> LENGTH: 58
<212> TYPE: PRT
<213> ORGANISM: Artificial Sequence
<220> FEATURE:
<223> OTHER INFORMATION: Chemically Synthesized

<400> SEQUENCE: 72

Val Asp Asn Lys Phe Asn Lys Glu Met Arg Lys Ala Tyr Trp Glu Ile
1               5                   10                  15

Gln Gly Leu Pro Asn Leu Asn Asn Arg Gln Lys Arg Ala Phe Ile Arg
            20                  25                  30

Ser Leu Tyr Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 73
<211> LENGTH: 58
<212> TYPE: PRT
<213> ORGANISM: Artificial Sequence
<220> FEATURE:
<223> OTHER INFORMATION: Chemically Synthesized

<400> SEQUENCE: 73

Val Asp Asn Lys Phe Asn Lys Glu Met Arg Asn Ala Tyr Trp Glu Ile
1               5                   10                  15

Ala Lys Leu Pro Asn Leu Asn Arg Glu Gln Lys Arg Ala Phe Ile Arg
            20                  25                  30

Ser Leu Tyr Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 74
<211> LENGTH: 58
<212> TYPE: PRT
<213> ORGANISM: Artificial Sequence
<220> FEATURE:
<223> OTHER INFORMATION: Chemically Synthesized

<400> SEQUENCE: 74

Val Asp Asn Lys Phe Asn Lys Glu Met Arg His Ala Tyr Trp Glu Ile
1               5                   10                  15

Val Gly Leu Pro Asn Leu Asn Met Ile Gln Gln Arg Ala Phe Ile Arg

```
                  20                  25                  30

Ser Leu Tyr Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 75
<211> LENGTH: 58
<212> TYPE: PRT
<213> ORGANISM: Artificial Sequence
<220> FEATURE:
<223> OTHER INFORMATION: Chemically Synthesized

<400> SEQUENCE: 75

Val Asp Asn Lys Phe Asn Lys Glu Leu Arg Asn Ala Tyr Trp Glu Ile
1               5                   10                  15

Val Lys Leu Pro Asn Leu Asn Arg Ala Gln Asn Arg Ala Phe Ile Arg
            20                  25                  30

Ser Leu Tyr Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 76
<211> LENGTH: 58
<212> TYPE: PRT
<213> ORGANISM: Artificial Sequence
<220> FEATURE:
<223> OTHER INFORMATION: Chemically Synthesized

<400> SEQUENCE: 76

Val Asp Asn Lys Phe Asn Lys Glu Leu Arg Thr Ala Tyr Trp Glu Ile
1               5                   10                  15

Ile Lys Leu Pro Asn Leu Asn Asn Tyr Gln Arg Arg Ala Phe Ile Arg
            20                  25                  30

Ser Leu Tyr Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 77
<211> LENGTH: 58
<212> TYPE: PRT
<213> ORGANISM: Artificial Sequence
<220> FEATURE:
<223> OTHER INFORMATION: Chemically Synthesized

<400> SEQUENCE: 77

Val Asp Asn Lys Phe Asn Lys Glu Pro Arg Glu Ala Tyr Trp Glu Ile
1               5                   10                  15

Gln Arg Leu Pro Asn Leu Asn Asn Lys Gln Lys Thr Ala Phe Ile Arg
            20                  25                  30

Ser Leu Tyr Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 78
<211> LENGTH: 58
<212> TYPE: PRT
<213> ORGANISM: Artificial Sequence
<220> FEATURE:
```

<223> OTHER INFORMATION: Chemically Synthesized

<400> SEQUENCE: 78

Val Asp Asn Lys Phe Asn Lys Glu Met Tyr Ala Ala Tyr Trp Glu Ile
1               5                   10                  15

Ile Asp Leu Pro Asn Leu Asn Thr Pro Gln Ile His Ala Phe Ile Arg
            20                  25                  30

Ser Leu Tyr Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 79
<211> LENGTH: 58
<212> TYPE: PRT
<213> ORGANISM: Artificial Sequence
<220> FEATURE:
<223> OTHER INFORMATION: Chemically Synthesized

<400> SEQUENCE: 79

Val Asp Asn Lys Phe Asn Lys Glu Thr Arg Ser Ala Tyr Trp Glu Ile
1               5                   10                  15

Val Asn Leu Pro Asn Leu Asn Gln Gly Gln Arg His Ala Phe Ile Lys
            20                  25                  30

Ser Leu Tyr Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 80
<211> LENGTH: 23
<212> TYPE: DNA
<213> ORGANISM: Artificial Sequence
<220> FEATURE:
<223> OTHER INFORMATION: Primer Sequence

<400> SEQUENCE: 80
gcttccggct cgtatgttgt gtg                                        23

<210> SEQ ID NO 81
<211> LENGTH: 21
<212> TYPE: DNA
<213> ORGANISM: Artificial Sequence
<220> FEATURE:
<223> OTHER INFORMATION: Primer Sequence
<220> FEATURE:
<221> NAME/KEY: misc_feature
<222> LOCATION: (1)...(1)
<223> OTHER INFORMATION: 5'-biotinylation

<400> SEQUENCE: 81
cggaaccaga gccaccaccg g                                          21

<210> SEQ ID NO 82
<211> LENGTH: 21
<212> TYPE: DNA
<213> ORGANISM: Artificial Sequence
<220> FEATURE:
<223> OTHER INFORMATION: Primer Sequence
<220> FEATURE:
<221> NAME/KEY: misc_feature

```
<222> LOCATION: (1)...(1)
<223> OTHER INFORMATION: 5'-biotinylation

<400> SEQUENCE: 82
cggaaccaga gccaccaccg g                                             21
```